United States Patent
Hartman et al.

(10) Patent No.: US 9,884,831 B2
(45) Date of Patent: Feb. 6, 2018

(54) AZOCANE AND AZONANE DERIVATIVES AND METHODS OF TREATING HEPATITIS B INFECTIONS

(71) Applicant: Novira Therapeutics, Inc., Doylestown, PA (US)

(72) Inventors: George D. Hartman, Lansdale, PA (US); Scott Kuduk, Harleysville, PA (US)

(73) Assignee: NOVIRA THERAPEUTICS, INC., Doylestown, PA (US)

( * ) Notice: Subject to any disclaimer, the term of this patent is extended or adjusted under 35 U.S.C. 154(b) by 0 days.

(21) Appl. No.: 15/073,965

(22) Filed: Mar. 18, 2016

(65) Prior Publication Data

US 2016/0272599 A1  Sep. 22, 2016

Related U.S. Application Data

(60) Provisional application No. 62/135,243, filed on Mar. 19, 2015.

(51) Int. Cl.
| | | |
|---|---|---|
| C07D 267/22 | (2006.01) | |
| C07D 225/02 | (2006.01) | |
| A61K 31/395 | (2006.01) | |
| A61K 38/21 | (2006.01) | |
| A61K 45/06 | (2006.01) | |

(52) U.S. Cl.
CPC .......... *C07D 267/22* (2013.01); *A61K 31/395* (2013.01); *A61K 38/212* (2013.01); *A61K 45/06* (2013.01); *C07D 225/02* (2013.01)

(58) Field of Classification Search
None
See application file for complete search history.

(56) References Cited

U.S. PATENT DOCUMENTS

| | | |
|---|---|---|
| 4,569,940 A | 2/1986 | Watts |
| 5,272,167 A | 12/1993 | Girijavallabhan et al. |
| 5,607,929 A | 3/1997 | Nicol |
| 5,919,970 A | 7/1999 | Song et al. |
| 5,939,423 A | 8/1999 | Karlin |
| 6,650,463 B2 | 11/2003 | Obikawa et al. |
| 7,186,735 B2 | 3/2007 | Strobel et al. |
| 7,338,956 B2 | 3/2008 | Strobel et al. |
| 7,595,322 B2 | 9/2009 | Morgan et al. |
| 7,750,158 B2 | 7/2010 | Shankar et al. |
| 7,888,373 B2 | 2/2011 | Morgan et al. |
| 8,084,457 B2 | 12/2011 | Choidas et al. |
| 8,097,728 B2 | 1/2012 | Gu et al. |
| 8,101,620 B2 | 1/2012 | Morgan et al. |
| 8,153,803 B2 | 4/2012 | Kazantsev |
| 8,404,747 B2 | 3/2013 | Kazantsev et al. |
| 8,609,668 B2 | 12/2013 | Cuconati et al. |
| 8,629,274 B2 | 1/2014 | Hartman et al. |
| 8,993,771 B2 | 3/2015 | Hartman et al. |
| 9,061,008 B2 | 6/2015 | Hartman et al. |
| 9,066,932 B2 | 6/2015 | Hartman et al. |
| 9,169,212 B2 | 10/2015 | Hartman et al. |
| 9,181,288 B2 | 11/2015 | Hartman et al. |
| 9,205,079 B2 | 12/2015 | Hartman et al. |
| 9,339,510 B2 | 5/2016 | Hartman et al. |
| 2004/0039009 A1 | 2/2004 | Prakash et al. |
| 2005/0009871 A1 | 1/2005 | Ramesh et al. |
| 2005/0054850 A1 | 3/2005 | Wu et al. |
| 2005/0239833 A1 | 10/2005 | Kazantsev |
| 2006/0100228 A1 | 5/2006 | Shankar et al. |
| 2007/0142440 A1 | 6/2007 | Burgdorf et al. |
| 2009/0036420 A1 | 2/2009 | Galley et al. |
| 2009/0105218 A1 | 4/2009 | Ulven et al. |
| 2009/0163545 A1 | 6/2009 | Goldfarb |
| 2009/0259044 A1 | 10/2009 | Kazantsev |
| 2011/0009622 A1 | 1/2011 | Jitsuoka et al. |
| 2011/0184019 A1 | 7/2011 | Zitzmann et al. |
| 2011/0189771 A1 | 8/2011 | Block et al. |
| 2011/0275630 A1 | 11/2011 | Matulenko et al. |
| 2013/0142827 A1 | 6/2013 | Block et al. |
| 2013/0203733 A1 | 8/2013 | Kazantsev et al. |
| 2013/0267517 A1 | 10/2013 | Guo et al. |
| 2013/0303552 A1 | 11/2013 | Xu et al. |
| 2015/0152073 A1 | 6/2015 | Hartman et al. |
| 2015/0174115 A1 | 6/2015 | Hartman et al. |
| 2015/0197533 A1 | 7/2015 | Hartman et al. |
| 2015/0216938 A1 | 8/2015 | Hartman |
| 2015/0225355 A1 | 8/2015 | Hartman |
| 2015/0259324 A1 | 9/2015 | Hartman et al. |
| 2015/0274652 A1 | 10/2015 | Hartman |

FOREIGN PATENT DOCUMENTS

| | | |
|---|---|---|
| CN | 102093320 A | 6/2011 |
| EP | 0 742 200 B1 | 7/1999 |
| EP | 2 280 001 A1 | 2/2011 |
| WO | 1984/003281 A1 | 8/1984 |
| WO | 1998/023285 A1 | 6/1998 |
| WO | 1999/038845 A1 | 8/1999 |
| WO | 1999/048492 A1 | 9/1999 |
| WO | 1999/065906 A1 | 12/1999 |
| WO | 2001/005390 A2 | 1/2001 |
| WO | 2001/019788 A2 | 3/2001 |

(Continued)

OTHER PUBLICATIONS

Fila-Hromadko. Croatia Chemica Acta, 1967, 39, 207-13, STN summary thereof.*
U.S. Appl. No. 13/723,869, filed Dec. 21, 2012, 2013/0251673, Sep. 26, 2013, U.S. Pat. No. 8,629,274, Jan. 14, 2014, George D. Hartman.
U.S. Appl. No. 14/100,219, filed Dec. 9, 2013, 2014/0179665, Jun. 26, 2014, U.S. Pat. No. 9,061,008, Jun. 23, 2015, George D. Hartman.
U.S. Appl. No. 14/517,606, filed Oct. 17, 2014, 2015/0152073, Jun. 4, 2015, George D. Hartman.

(Continued)

*Primary Examiner* — Noble E Jarrell
(74) *Attorney, Agent, or Firm* — Brian C. Trinque; Lathrop Gage LLP

(57) ABSTRACT

Provided herein are compounds useful for the treatment of HBV infection in a subject in need thereof, pharmaceutical compositions thereof, and methods of inhibiting, suppressing, or preventing HBV infection in the subject.

24 Claims, No Drawings

(56) References Cited

FOREIGN PATENT DOCUMENTS

| | | |
|---|---|---|
| WO | 2001/055121 A1 | 8/2001 |
| WO | 2001/085694 A2 | 11/2001 |
| WO | 2002/051410 A2 | 7/2002 |
| WO | 2003/007955 A2 | 1/2003 |
| WO | 2003/044016 A1 | 5/2003 |
| WO | 2004/022060 A2 | 3/2004 |
| WO | 2004/058709 A1 | 7/2004 |
| WO | 2004/086865 A1 | 10/2004 |
| WO | 2004/099192 A2 | 11/2004 |
| WO | 2004/100947 A2 | 11/2004 |
| WO | 2005/016922 A2 | 2/2005 |
| WO | 2005/044797 A1 | 5/2005 |
| WO | 2005/087217 A1 | 9/2005 |
| WO | 2005/105785 A2 | 11/2005 |
| WO | 2005/115374 A1 | 12/2005 |
| WO | 2006/002133 A1 | 1/2006 |
| WO | 2006/024834 A1 | 3/2006 |
| WO | 2006/053109 A1 | 5/2006 |
| WO | 2006/067445 A2 | 6/2006 |
| WO | 2006/067446 A1 | 6/2006 |
| WO | 2006/123257 A2 | 11/2006 |
| WO | 2006/128129 A2 | 11/2006 |
| WO | 2006/128172 A2 | 11/2006 |
| WO | 2007/031791 A1 | 3/2007 |
| WO | 2008/011476 A1 | 1/2008 |
| WO | 2008/022171 A1 | 2/2008 |
| WO | 2008/093614 A1 | 8/2008 |
| WO | 2008/137794 A1 | 11/2008 |
| WO | 2009/016088 A1 | 2/2009 |
| WO | 2009/062402 A1 | 7/2009 |
| WO | 2009/086303 A2 | 7/2009 |
| WO | 2009/131065 A1 | 10/2009 |
| WO | 2010/018113 A2 | 2/2010 |
| WO | 2010/043592 A1 | 4/2010 |
| WO | 2010/088000 A2 | 8/2010 |
| WO | 2010/123139 A1 | 10/2010 |
| WO | 2011/002635 A1 | 1/2011 |
| WO | 2011/088015 A1 | 7/2011 |
| WO | 2011/088561 A1 | 7/2011 |
| WO | 2011/109237 A2 | 9/2011 |
| WO | 2011/112191 A1 | 9/2011 |
| WO | 2011/123609 A1 | 10/2011 |
| WO | 2011/155898 A1 | 12/2011 |
| WO | 2012/016133 A2 | 2/2012 |
| WO | 2012/018635 A2 | 2/2012 |
| WO | 2012/075235 A1 | 6/2012 |
| WO | 2012/080050 A1 | 6/2012 |
| WO | 2012/136834 A1 | 10/2012 |
| WO | 2013/006394 A1 | 1/2013 |
| WO | 2013/096744 A1 | 6/2013 |
| WO | 2013/102655 A1 | 7/2013 |
| WO | 2013/130703 A2 | 9/2013 |
| WO | 2013/181584 A2 | 12/2013 |
| WO | 2014/033167 A1 | 3/2014 |
| WO | 2014/033170 A1 | 3/2014 |
| WO | 2014/033176 A1 | 3/2014 |
| WO | 2014/037480 A1 | 3/2014 |
| WO | 2014/106019 A2 | 7/2014 |

OTHER PUBLICATIONS

U.S. Appl. No. 14/134,113, filed Dec. 19, 2013, 2014/0178337, Jun. 26, 2014, U.S. Pat. No. 9,066,932, Jun. 30, 2015, George D. Hartman.
U.S. Appl. No. 14/728,126, filed Jun. 2, 2015, 2015/0259324, Sep. 17, 2015, George D. Hartman.
U.S. Appl. No. 14/206,496, filed Mar. 12, 2014, 2014/0275167, Sep. 18, 2014, U.S. Pat. No. 8,993,771, Mar. 31, 2015, George D. Hartman.
U.S. Appl. No. 14/642,393, filed Mar. 9, 2015, 2015/0174115, Jun. 25, 2015, U.S. Pat. No. 9,205,079, Dec. 8, 2015, George D. Hartman.
U.S. Appl. No. 14/931,173, filed Nov. 3, 2015, 2016-0158214, Jun. 9, 2016, George D. Hartman.
U.S. Appl. No. 14/511,964, filed Oct. 10, 2014, 2015/0197493, Jul. 16, 2015, U.S. Pat. No. 9,169,212, Oct. 27, 2015, George D. Hartman.
U.S. Appl. No. 14/694,147, filed Apr. 23, 2015, 2015/0225355, Aug. 13, 2015, George D. Hartman.
U.S. Appl. No. 14/597,814, filed Jan. 15, 2015, 2015/0197533, Jul. 16, 2015, U.S. Pat. No. 9,181,288, Nov. 10, 2015, George D. Hartman.
U.S. Appl. No. 14/856,761, filed Sep. 17, 2015, 2016/0000812, Jan. 7, 2016, U.S. Pat. No. 9,339,510, May 17, 2016, George D. Hartman.
U.S. Appl. No. 14/670,001, filed Mar. 26, 2015, 2015/0274652, Oct. 1, 2015, U.S. Pat. No. 9,400,280, Jul. 26, 2016, George D. Hartman.
U.S. Appl. No. 14/615,292, filed Feb. 5, 2015, 2015/0216938, Aug. 6, 2015, George D. Hartman.
[Online] CAS (STN), 148:183450, Jan. 24, 2008, RN 296790-26-6.
[Online] Registry via STN, May 6, 2011, RN 1291044-81-9.
[Online] Registry via STN, Oct. 7, 2008, RN 1057788-44-9.
[Online] Registry via STN, Oct. 7, 2008, RN 1057871-39-2.
[Online] Registry via STN, Aug. 15, 2011, RN 1317923-24-2.
[Online] Registry via STN, Aug. 15, 2011, RN 1318022-74-0.
[Online] Registry via STN, May 18, 2011, RN 1296380-95-4.
[Online] Registry via STN, Oct. 18, 2000, RN 296894-70-7.
[Online] Registry via STN, Sep. 20, 2013, RN 1452780-00-5.
Campagna et al. (Apr. 10, 2013) "Sulfamoylbenzamide Derivatives Inhibit the Assembly of Hepatitis B Virus Nucleocapsids," Journal of Virology. 87(12):6931-6942.
Duan et al. (2009) "2-Phenylquinazolin-4(3H)-one, a class of potent PDE5 inhibitors with high selectivity versus PDE6," Bioorganic and Medicinal Chemistry. 19(10):2777-2779.
El-Sharief et al. (1987) "Synthesis of different types of chlorinated sulfonamides with expected insecticidal and bactericidal activities," Proceedings of the Indian National Science Academy, Part A: Physical Sciences. 53(1):179-188.
Ermann et al. (2008) "Arylsulfonamide CB2 receptor agonists: SAR and optimization of CB2 selectivity," Bioorganic & Medicinal Chemistry Letters. 18(5):1725-1729.
Kim et al. (Apr. 9, 2011) "Discovery of novel HCV polymerase inhibitors using pharmacophore-based virtual screening," Bioorganic and Medicinal Chemistry. 21(11):3329-3334.
Lambeng et al. (2007) "Arylsulfonamides as a new class of cannabinoid CB1 receptor ligands: Identification of a lead and initial SAR studies," Bioorganic & Medicinal Chemistry Letters. 17(1):272-277.
Lau et al. (2005) "Peginterferon Alfa-2a, Lamivudine, and the Combination for HBeAg-Positive Chronic Hepatitis B," The New England Journal of Medicine. 352(26):2682-2695.
Liaw et al. (2009) "Hepatitis B virus infection," Lancet. 373:582-592.
Mohamed et al. (1986) "Synthesis of different types of chlorinated sulfonamides with expected insecticidal and antimicrobial activities," Acta Pharmaceutica Jugoslavica. 36(3):301-310.
Patani et al. (1996) "Bioisosterism: A Rational Approach in Drug Design," Chem. Rev. 96:3147-3176.
Taylor et al. (Mar. 3, 2011) "A Brain-Permeable Small Molecule Reduces Neuronal Cholesterol by Inhibiting Activity of Sirtuin 2 Deacetylase," ACS Chemical Biology. 6(6):540-546.
Thompson et al. (2007) "Toll-like receptors, RIG-I-like RNA helicases and the antiviral innate immune response," Immunology and Cell Biology. 85:435-445.
International Search Report with Written Opinion corresponding to International Patent Application No. PCT/US2012/071195, dated Dec. 21, 2012.
International Search Report with Written Opinion corresponding to International Patent Application No. PCT/US2015/011663, dated Apr. 29, 2015.
International Search Report with Written Opinion corresponding to International Patent Application No. PCT/US2015/014663, dated Apr. 29, 2015.

(56) References Cited

OTHER PUBLICATIONS

International Search Report with Written Opinion corresponding to International Patent Application No. PCT/US2016/023066, dated May 11, 2016.
Search Report with Written Opinion corresponding to Singapore Patent Application No. 11201402660Y, completed May 22, 2015.
Supplementary European Search Report corresponding to European Patent Application No. 12859684, dated May 27, 2015.

* cited by examiner

AZOCANE AND AZONANE DERIVATIVES AND METHODS OF TREATING HEPATITIS B INFECTIONS

RELATED APPLICATIONS

This application claims priority to U.S. Provisional Patent Application No. 62/135,243, filed on Mar. 19, 2015. The entire content of this application is herein incorporated by reference.

BACKGROUND

Chronic hepatitis B virus (HBV) infection is a significant global health problem, affecting over 5% of the world population (over 350 million people worldwide and 1.25 million individuals in the U.S.).

Despite the availability of a prophylactic HBV vaccine, the burden of chronic HBV infection continues to be a significant unmet worldwide medical problem, due to suboptimal treatment options and sustained rates of new infections in most parts of the developing world.

Current treatments do not provide a cure and are limited to only two classes of agents (interferon and nucleoside analogues/inhibitors of the viral polymerase); drug resistance, low efficacy, and tolerability issues limit their impact. The low cure rates of HBV are attributed, at least in part, to the presence and persistence of covalently closed circular DNA (cccDNA) in the nucleus of infected hepatocytes. However, persistent suppression of HBV DNA slows liver disease progression and helps prevent hepatocellular carcinoma. Current therapy goals for HBV-infected patients are directed to reducing serum HBV DNA to low or undetectable levels, and reducing or preventing the development of cirrhosis and hepatocellular carcinoma.

There is a need in the art for therapeutic agents that treat, ameliorate or prevent HBV infection. Administration of these therapeutic agents to an HBV infected patient, either as monotherapy or in combination with other HBV treatments or ancillary treatments, will lead to significantly improved prognosis, diminished progression of the disease, and enhanced seroconversion rates.

SUMMARY OF THE INVENTION

Provided herein are compounds useful for the treatment of HBV infection in a subject in need thereof.

In one aspect, provided herein are compounds having the Formula I:

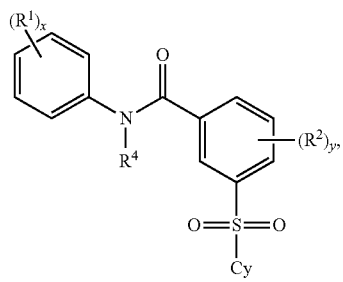

or a pharmaceutically acceptable salt thereof, wherein Cy is

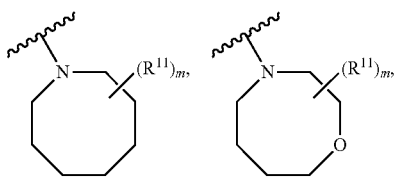

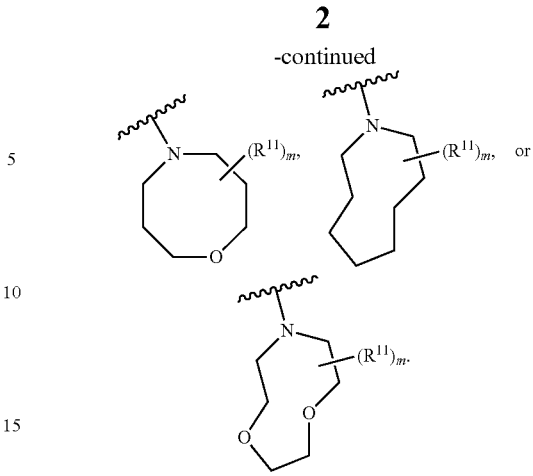

In another aspect, provided herein is a composition comprising a compound of Formula I, or a pharmaceutically acceptable salt thereof.

In an embodiment, the composition is a pharmaceutical composition and further comprises at least one pharmaceutically acceptable carrier.

In another aspect, provided herein is a method of treating an HBV infection in an individual in need thereof, comprising administering to the individual a therapeutically effective amount of a compound of Formula I.

In yet another aspect, provided herein is a method of reducing the viral load associated with an HBV infection in an individual in need thereof, comprising administering to the individual a therapeutically effective amount of a compound of Formula I.

In still another aspect, provided herein is a method of reducing reoccurrence of an HBV infection in an individual in need thereof, comprising administering to the individual a therapeutically effective amount of a compound according to of Formula I.

Also provided herein is a method of reducing an adverse physiological impact of an HBV infection in an individual in need thereof, comprising administering to the individual a therapeutically effective amount of a compound of Formula I.

In another aspect, provided herein is a method of inducing remission of hepatic injury from an HBV infection in an individual in need thereof, comprising administering to the individual a therapeutically effective amount of a compound of Formula I.

In yet another aspect, provided herein is a method of reducing the physiological impact of long-term antiviral therapy for HBV infection in an individual in need thereof, comprising administering to the individual a therapeutically effective amount of a compound of Formula I.

In still another aspect, provided herein is a method of prophylactically treating an HBV infection in an individual in need thereof, wherein the individual is afflicted with a latent HBV infection, comprising administering to the individual a therapeutically effective amount of a compound of Formula I.

Any of the above methods may further comprise administration to the individual at least one additional therapeutic agent. In an embodiment, the additional therapeutic agent is selected from the group consisting of a HBV polymerase inhibitor, immunomodulatory agents, pegylated interferon, viral entry inhibitor, viral maturation inhibitor, capsid assembly modulator, reverse transcriptase inhibitor, a cyclophilin/TNF inhibitor, a TLR-agonist, and an HBV vaccine, and a combination thereof.

In another embodiment, the therapeutic agent is a reverse transcriptase inhibitor, and is at least one of Zidovudine, Didanosine, Zalcitabine, 2',3'-dideoxyadenosine, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, and Etravirine.

In another embodiment, the additional therapeutic agent is a TLR-agonist. In a preferred embodiment, the TLR-agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl]acetate).

In a further embodiment of the combination therapy, the additional therapeutic agent is an interferon, wherein the interferon is any interferon, which may be optionally pegylated. In yet a further embodiment, the therapeutic agent is an interferon selected from the group consisting of interferon alpha (IFN-α), interferon beta (IFN-β), interferon lambda (IFN-λ), and interferon gamma (IFN-γ). In a preferred embodiment, the interferon is interferon-alpha-2a, interferon-alpha-2b, interferon-alpha-n1, pegylated interferon-alpha-2a, or pegylated interferon-alpha-2b. In another preferred embodiment, the interferon is interferon-alpha-2a, interferon-alpha-2b, or interferon-alpha-n1. In a yet another preferred embodiment, the interferon-alpha-2a or interferon-alpha-2b is pegylated. In still another preferred embodiment, the interferon-alpha-2a is pegylated interferon-alpha-2a (PEGASYS).

In another embodiment of the methods provided herein, administering the compound of Formula I allows for administering of the at least one additional therapeutic agent at a lower dose or frequency as compared to the administering of the at least one additional therapeutic agent alone that is required to achieve similar results in prophylactically treating an HBV infection in an individual in need thereof.

In yet another embodiment of the methods provided herein, administering the compound of Formula I reduces the viral load in the individual to a greater extent or at a faster rate compared to the administering of a compound selected from the group consisting of a HBV polymerase inhibitor, interferon, viral entry inhibitor, viral maturation inhibitor, distinct capsid assembly modulator, antiviral compounds, and any combination thereof.

In still another embodiment of the methods provided herein, administering the compound of Formula I causes a lower incidence of viral mutation or viral resistance than the administering of a compound selected from the group consisting of a HBV polymerase inhibitor, an interferon, a viral entry inhibitor, a viral maturation inhibitor, a capsid assembly modulator, an antiviral compound, and combinations thereof.

In any of the methods provided herein, the method may further comprise administering to the individual at least one HBV vaccine, a nucleoside HBV inhibitor, an interferon or any combination thereof. In an embodiment, the HBV vaccine is selected from the group consisting of RECOMBIVAX HB, ENGERIX-B, ELOVAC B, GENEVAC-B, and SHANVAC B.

In another aspect, provided herein is a method of treating an HBV infection in an individual in need thereof, comprising reducing the HBV viral load by administering to the individual a therapeutically effective amount of a compound of Formula I alone or in combination with a reverse transcriptase inhibitor; and further administering to the individual a therapeutically effective amount of HBV vaccine. In an embodiment, the reverse transcriptase inhibitor is at least one of Zidovudine, Didanosine, Zalcitabine, 2',3'-dideoxyadenosine, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, and Etravirine.

In another embodiment of the methods provided herein, the method further comprises monitoring the HBV viral load of the subject, and wherein the method is carried out for a period of time such that the HBV virus is undetectable.

DETAILED DESCRIPTION OF THE INVENTION

Provided herein are compounds that are useful in the treatment and prevention of HBV infection in man. In a non-limiting aspect, these compounds may modulate or disrupt HBV assembly and other HBV core protein functions necessary for the generation of infectious particles by interacting with HBV capsid to afford defective viral particles with greatly reduced virulence. The compounds of the invention have potent antiviral activity, exhibit favorable metabolic, tissue distribution, safety and pharmaceutical profiles, and are suitable for use in man.

The HBV capsid protein plays essential functions during the viral life cycle. HBV capsid/core proteins form metastable viral particles or protein shells that protect the viral genome during intercellular passage, and also play a central role in viral replication processes, including genome encapsidation, genome replication, and virion morphogenesis and egress. Capsid structures also respond to environmental cues to allow un-coating after viral entry. Consistently, proper capsid assembly and function of core protein have been found to be critical for viral infectivity.

The crucial function of HBV capsid proteins imposes stringent evolutionary constraints on the viral capsid protein sequence, leading to the observed low sequence variability and high conservation. Consistently, mutations in HBV capsid that disrupt its assembly are lethal, and mutations that perturb capsid stability severely attenuate viral replication. The more conserved a drug target is, the fewer replication-competent resistance mutations are acquired by patients. Indeed, natural mutations in HBV capsid for chronically infected patients accumulate in only four out of 183 residues in the full length protein. Thus, HBV capsid assembly and function inhibitors may elicit lower drug resistance emergence rates relative to existing HBV antivirals. Further, drug therapies that target HBV capsid could be less prone to drug-resistant mutations when compared to drugs that target traditional neuraminidase enzyme active sites. Reports describing compounds that bind viral capsids and inhibit replication of HIV, rhinovirus and HBV provide strong pharmacological proof of concept for viral capsid proteins as antiviral drug targets.

In one aspect, the compounds of the invention are useful in HBV treatment by disrupting, accelerating, reducing, delaying and/or inhibiting normal viral capsid assembly and/or disassembly of immature or mature particles, thereby inducing aberrant capsid morphology and leading to antiviral effects such as disruption of virion assembly and/or disassembly, virion maturation, and/or virus egress. In one embodiment, a disruptor of capsid assembly interacts with mature or immature viral capsid to perturb the stability of the capsid, thus affecting assembly and/or disassembly. In another embodiment, a disruptor of capsid assembly perturbs protein folding and/or salt bridges required for stability, function and/or normal morphology of the viral capsid, thereby disrupting and/or accelerating capsid assembly and/or disassembly. In yet another embodiment, the compounds of the invention bind capsid and alter metabolism of cellular polyproteins and precursors, leading to abnormal accumulation of protein monomers and/or oligomers and/or abnormal particles, which causes cellular toxicity and death of infected cells. In another embodiment, the compounds of the invention cause failure of the formation of capsid of optimal stability, affecting efficient uncoating and/or disassembly of viruses (e.g., during infectivity).

In one embodiment, the compounds of the invention disrupt and/or accelerate capsid assembly and/or disassembly when the capsid protein is immature. In another embodiment, the compounds of the invention disrupt and/or accelerate capsid assembly and/or disassembly when the capsid protein is mature. In yet another embodiment, the compounds of the invention disrupt and/or accelerate capsid assembly and/or disassembly during viral infectivity. In yet another embodiment, the disruption and/or acceleration of capsid assembly and/or disassembly attenuates HBV viral infectivity and/or reduces viral load. In yet another embodiment, disruption, acceleration, inhibition, delay and/or reduction of capsid assembly and/or disassembly eradicates the virus from the host organism. In yet another embodiment, eradication of the HBV from a host advantageously obviates the need for chronic long-term therapy and/or reduces the duration of long-term therapy.

In one embodiment, the compounds described herein are suitable for monotherapy and are effective against natural or native HBV strains and against HBV strains resistant to currently known drugs. In another embodiment, the compounds described herein are suitable for use in combination therapy.

In another embodiment, the compounds of the invention can be used in methods of modulating (e.g., inhibit or disrupt) the activity, stability, function, and viral replication properties of HBV cccDNA. In yet another embodiment, the compounds of the invention can be used in methods of diminishing or preventing the formation of HBV cccDNA.

In another embodiment, the compounds of the invention can be used in methods of modulating (e.g., inhibit or disrupt) the activity of HBV cccDNA. In yet another embodiment, the compounds of the invention can be used in methods of diminishing or preventing the formation of HBV cccDNA.

Definitions

Listed below are definitions of various terms used to describe this invention. These definitions apply to the terms as they are used throughout this specification and claims, unless otherwise limited in specific instances, either individually or as part of a larger group.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, organic chemistry, and peptide chemistry are those well-known and commonly employed in the art.

As used herein, the articles "a" and "an" refer to one or to more than one (i.e. to at least one) of the grammatical object of the article. By way of example, "an element" means one element or more than one element. Furthermore, use of the term "including" as well as other forms, such as "include", "includes," and "included," is not limiting.

As used herein, the term "about" will be understood by persons of ordinary skill in the art and will vary to some extent on the context in which it is used. As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "capsid assembly modulator" refers to a compound that disrupts or accelerates or inhibits or hinders or delays or reduces or modifies normal capsid assembly (e.g., during maturation) or normal capsid disassembly (e.g., during infectivity) or perturbs capsid stability, thereby inducing aberrant capsid morphology and function. In one embodiment, a capsid assembly modulator accelerates capsid assembly or disassembly, thereby inducing aberrant capsid morphology. In another embodiment, a capsid assembly modulator interacts (e.g. binds at an active site, binds at an allosteric site, modifies and/or hinders folding and the like) with the major capsid assembly protein (CA), thereby disrupting capsid assembly or disassembly. In yet another embodiment, a capsid assembly modulator causes a perturbation in structure or function of CA (e.g., ability of CA to assemble, disassemble, bind to a substrate, fold into a suitable conformation, or the like), which attenuates viral infectivity and/or is lethal to the virus.

As used herein, the term "treatment" or "treating," is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has HBV infection, a symptom of HBV infection or the potential to develop HBV infection, with the purpose to cure, heal, alleviate, relieve, alter, remedy, ameliorate, improve or affect HBV infection, the symptoms of HBV infection or the potential to develop HBV infection. Such treatments may be specifically tailored or modified, based on knowledge obtained from the field of pharmacogenomics.

As used herein, the term "prevent" or "prevention" means no disorder or disease development if none had occurred, or no further disorder or disease development if there had already been development of the disorder or disease. Also considered is the ability of one to prevent some or all of the symptoms associated with the disorder or disease.

As used herein, the term "patient," "individual" or "subject" refers to a human or a non-human mammal. Non-human mammals include, for example, livestock and pets, such as ovine, bovine, porcine, canine, feline and murine mammals. Preferably, the patient, subject or individual is human.

As used herein, the terms "effective amount," "pharmaceutically effective amount" and "therapeutically effective amount" refer to a nontoxic but sufficient amount of an agent to provide the desired biological result. That result may be reduction and/or alleviation of the signs, symptoms, or causes of a disease, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing undesirable biological effects or interacting in a deleterious manner with any of the components of the composition in which it is contained.

As used herein, the term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

As used herein, the term "composition" or "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the term "alkyl," by itself or as part of another substituent means, unless otherwise stated, a straight or branched chain hydrocarbon having the number of carbon atoms designated (i.e., $C_{1-6}$ means one to six carbon atoms) and includes straight, branched chain, or cyclic substituent groups. Examples include methyl, ethyl, propyl, isopropyl, butyl, isobutyl, tert-butyl, pentyl, neopentyl, hexyl, and cyclopropylmethyl. Most preferred is ($C_{1-6}$)alkyl, particularly ethyl, methyl, isopropyl, isobutyl, n-pentyl, n-hexyl and cyclopropylmethyl.

As used herein, the term "halo" or "halogen" alone or as part of another substituent means, unless otherwise stated, a fluorine, chlorine, bromine, or iodine atom, preferably, fluorine, chlorine, or bromine, more preferably, fluorine or chlorine.

As used herein, the term "cycloalkyl" refers to a mono cyclic or polycyclic non-aromatic radical, wherein each of the atoms forming the ring (i.e., skeletal atoms) is a carbon atom. In one embodiment, the cycloalkyl group is saturated or partially unsaturated. In another embodiment, the cycloalkyl group is fused with an aromatic ring. Cycloalkyl groups include groups having 3 to 10 ring atoms ($C_{3-10}$ cycloalkyl), or groups having 3 to 7 ring atoms ($C_{3-7}$ cycloalkyl).

The term cycloalkyl includes "unsaturated nonaromatic carbocyclyl" or "nonaromatic unsaturated carbocyclyl" groups, both of which refer to a nonaromatic carbocycle as defined herein, which contains at least one carbon carbon double bond or one carbon carbon triple bond.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, and —CH$_2$—S—CH$_2$—CH$_3$. Up to two heteroatoms may be consecutive, such as, for example, —CH$_2$—NH—OCH$_3$, or —CH$_2$—CH$_2$—S—S—CH$_3$. Preferred heteroalkyl groups have 1-10 carbons.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

As used herein, the term "aromatic" refers to a carbocycle or heterocycle with one or more polyunsaturated rings and having aromatic character, i.e., having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl. Preferred examples are phenyl and naphthyl, most preferred is phenyl. In some embodiments, aryl groups have six carbon atoms. In some embodiments, aryl groups have from six to ten carbon atoms. In some embodiments, aryl groups have from six to sixteen carbon atoms.

As used herein, the term "heteroaryl" or "heteroaromatic" refers to a heterocycle having aromatic character. In some embodiments, heteroaryl or heteroaromatic groups have two to five carbon atoms. In some embodiments, heteroaryl or heteroaromatic groups have from two to ten carbon atoms. In some embodiments, heteroaryl or heteroaromatic groups have from two to sixteen carbon atoms. A polycyclic heteroaryl may include one or more rings that are partially saturated. In some embodiments, polycyclic heteroaryl groups have two to five carbon atoms. In some embodiments, polycyclic heteroaryl groups have from two to ten carbon atoms. In some embodiments, polycyclic heteroaryl groups have from two to sixteen carbon atoms.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

Compounds of the Invention

The present invention relates to the discovery of compounds that are useful in the treatment and prevention of HBV infection in man. In one aspect, the compounds of the invention are useful in HBV treatment by disrupting, accelerating, reducing delaying or inhibiting normal viral capsid assembly or disassembly of immature or mature particles, thereby inducing aberrant capsid morphology and leading to antiviral effects such as disruption of virion assembly or disassembly or virion maturation, or virus egress.

In another aspect, compounds of the invention bind to core protein thereby inducing aberrant virion and leading to antiviral effects such as disruption of virion assembly, disassembly, maturation, or virus egress.

The capsid assembly disruptors disclosed herein may be used as monotherapy or in cross-class combination regimens for treating HBV infection in man. Combination therapy with drugs exhibiting different mechanism of action (MOA) that act at different steps in the virus life cycle may deliver greater efficacy due to additive or synergistic antiviral effects. Clinically evaluated HIV treatment regimens have shown that combination therapy improves the efficacy of viral load reduction, and dramatically reduces emergence of antiviral resistance. Combination therapy for the treatment of Hepatitis C (HCV) virus infection has also resulted in significant improvement in sustained antiviral response and eradication rates. Thus, use of the HBV capsid assembly inhibitors of the present invention in combination with, for example, neuraminidase drugs, is likely to deliver a more profound antiviral effect and greater disease eradication rates than current standards of care.

Capsid assembly plays a central role in HBV genome replication. HBV polymerase binds pre-genomic HBV RNA (pgRNA), and pgRNA encapsidation must occur prior to HBV DNA synthesis. Moreover, it is well established that nuclear accumulation of the cccDNA replication intermediate, which is responsible for maintenance of chronic HBV replication in the presence of nucleoside suppressive therapy, requires the capsid for shuttling HBV DNA to the nuclei. Therefore, the HBV capsid assembly disruptors of the invention have the potential to increase HBV eradication rates through synergistic or additive suppression of viral genome replication and to further reduce accumulation of cccDNA when used alone or in combination with existing nucleoside drugs. The capsid assembly disruptors of the present invention may also alter normal core protein function or degradation, potentially leading to altered MHC-1 antigen presentation, which may in turn increase seroconversion/eradication rates through immuno-stimulatory activity, more effectively clearing infected cells.

In one aspect, drug resistance poses a major threat to current therapies for chronic HBV infection, and cross-class combination therapy is a proven strategy for delaying emergence of drug resistance strains. The capsid assembly disruptors of the present invention can, when administered alone or in combination with other HBV therapy, offer enhanced drug resistant profiles and improved management of chronic HBV.

The compounds useful within the invention can be synthesized using techniques well-known in the art of organic synthesis. The starting materials and intermediates required for the synthesis may be obtained from commercial sources or synthesized according to methods known to those skilled in the art.

In one aspect, the compound of the invention is a compound of Formula I:

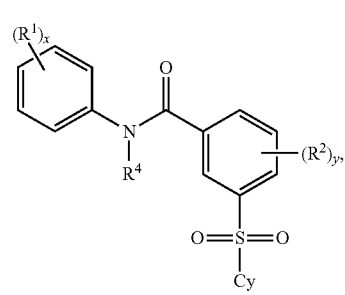

or a pharmaceutically acceptable salt thereof;
wherein
$R^4$ is H or $C_1$-$C_3$ alkyl;
$R^1$ is, independently at each occurrence, —OH, halo, —CN, —$NO_2$, —$H_2PO_4$, —$C_1$-$C_6$ alkyl, —O—$C_1$-$C_6$ alkyl, —$C_1$-$C_6$ heteroalkyl, —O—$C_1$-$C_6$ heteroalkyl, —$C_3$-$C_{10}$ cycloalkyl, —$C_3$-$C_{10}$ heterocycloalkyl, $C_6$-$C_{10}$ aryl, $C_5$-$C_9$ heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(C$_6$-C$_{10}$ aryl), or —C$_1$-C$_4$ alkyl-(C$_5$-C$_9$ heteroaryl), wherein the alkyl, heteroalkyl, cycloalkyl, heterocycloalkyl, aryl and heteroaryl groups are optionally substituted 1-5 times with halo, —OH, —CN, or —NO$_2$;

R$^2$ is, independently at each occurrence, —OH, halo, —CN, —NO$_2$, R$^6$, or OR$^6$, wherein R$^6$ is, independently at each occurrence, —C$_1$-C$_6$ alkyl, —C$_1$-C$_6$ heteroalkyl, —C$_3$-C$_{10}$ cycloalkyl, —C$_3$-C$_{10}$ heterocycloalkyl, C$_6$-C$_{10}$ aryl, C$_5$-C$_{10}$ heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(C$_6$-C$_{10}$ aryl), or —C$_1$-C$_4$ alkyl-(C$_5$-C$_{10}$ heteroaryl), wherein the alkyl, heteroalkyl, cycloalkyl, heterocycloalkyl, aryl and heteroaryl groups are optionally substituted 1-5 times with halo, —OH, —CN, or —NO$_2$;

Cy is

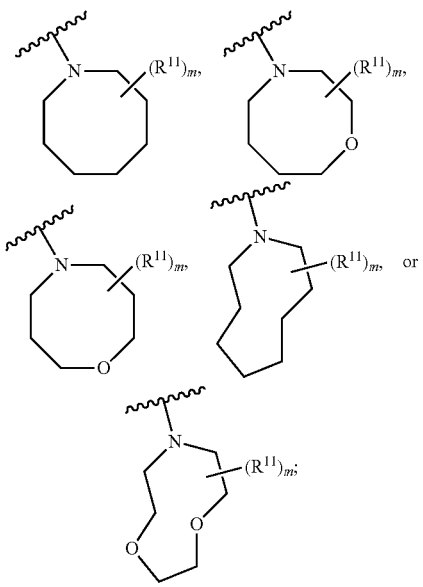

wherein

R$^{11}$ is, independently at each occurrence, —OH, halo, —CN, —NO$_2$, —C$_1$-C$_6$ alkyl, —O—C$_1$-C$_6$ alkyl, —C$_1$-C$_6$ hetero alkyl, —O—C$_1$-C$_6$ hetero alkyl, —C$_3$-C$_{10}$ cycloalkyl, —C$_3$-C$_{10}$ heterocycloalkyl, C$_6$-C$_{10}$ aryl, C$_5$-C$_9$ heteroaryl, —C$_1$-C$_4$ alkyl-(C$_3$-C$_{10}$ cycloalkyl), —C$_1$-C$_4$ alkyl-(C$_3$-C$_{10}$ heterocycloalkyl), —C$_1$-C$_4$ alkyl-(C$_6$-C$_{10}$ aryl), or —C$_1$-C$_4$ alkyl-(C$_5$-C$_9$ heteroaryl), wherein the alkyl, heteroalkyl, cycloalkyl, heterocycloalkyl, aryl and heteroaryl groups are optionally substituted 1-5 times with halo, —OH, —CN, or —NO$_2$, or two R$^{11}$ groups, together with the carbons to which they are attached, join to form a cyclic phosphate ring;

m is 0, 1, 2, 3, or 4;

x is 0, 1, 2, 3, 4, or 5; and y is 0, 1, 2, 3, or 4. In one embodiment, y is 0, 1, or 2.

In an embodiment of Formula I provided herein, or a pharmaceutically acceptable salt thereof, R$^4$ is H;

m is 0, 1, 2, or 3;

x is 0, 1, 2, or 3; and y is 0, 1, 2, or 3. In a further embodiment, y is 0, 1, or 2. In yet another embodiment, y is 1.

In another embodiment of Formula I provided herein, or a pharmaceutically acceptable salt thereof, R$^1$ is, independently at each occurrence, —OH, halo, —CN, —NO$_2$, —C$_1$-C$_6$ alkyl, —O—C$_1$-C$_6$ alkyl, —C$_1$-C$_6$ heteroalkyl, —O—C$_1$-C$_6$ heteroalkyl, —C$_3$-C$_{10}$ cycloalkyl, —C$_3$-C$_{10}$ heterocycloalkyl, —C$_1$-C$_4$ alkyl-(C$_3$-C$_{10}$ cycloalkyl), or —C$_1$-C$_4$ alkyl-(C$_3$-C$_{10}$ heterocycloalkyl), wherein the alkyl group is optionally substituted 1-5 times with halo or —OH.

In yet another embodiment of Formula I provided herein, or a pharmaceutically acceptable salt thereof, R$^2$ is, independently at each occurrence, —OH, halo, —CN, —NO$_2$, R$^6$, or OR$^6$, wherein R$^6$ is, independently at each occurrence, —C$_1$-C$_6$ alkyl, —C$_1$-C$_6$ heteroalkyl, —C$_3$-C$_{10}$ cycloalkyl, —C$_3$-C$_{10}$ heterocycloalkyl, —C$_1$-C$_4$ alkyl-(C$_3$-C$_{10}$ cycloalkyl), or —C$_1$-C$_4$ alkyl-(C$_3$-C$_{10}$ heterocycloalkyl), wherein the alkyl group is optionally substituted 1-5 times with halo or —OH.

In still another embodiment of Formula I provided herein, or a pharmaceutically acceptable salt thereof, R$^{11}$ is, independently at each occurrence, —OH, halo, —CN, —NO$_2$, —C$_1$-C$_6$ alkyl, —O—C$_1$-C$_6$ alkyl, —C$_1$-C$_6$ heteroalkyl, —O—C$_1$-C$_6$ heteroalkyl, —C$_3$-C$_{10}$ cycloalkyl, —C$_3$-C$_{10}$ heterocycloalkyl, —C$_1$-C$_4$ alkyl-(C$_3$-C$_{10}$ cycloalkyl), or —C$_1$-C$_4$ alkyl-(C$_3$-C$_{10}$ heterocycloalkyl), wherein the alkyl group is optionally substituted 1-5 times with halo or —OH.

In another embodiment of Formula I provided herein, or a pharmaceutically acceptable salt thereof, R$^{11}$ is, independently at each occurrence, —OH, halo, —C$_1$-C$_6$ alkyl, —C$_1$-C$_6$ heteroalkyl, —C$_3$-C$_{10}$ cycloalkyl, or —C$_3$-C$_{10}$ heterocycloalkyl.

In yet another embodiment of Formula I provided herein, or a pharmaceutically acceptable salt thereof, R$^4$ is H;

each R$^1$ is, independently at each occurrence, —OH, halo, —CN, —NO$_2$, or —C$_1$-C$_6$ alkyl;

R$^2$ is selected from —OH, halo, —C$_1$-C$_6$ alkyl, —C$_1$-C$_6$ heteroalkyl, —C$_3$-C$_{10}$ cycloalkyl, and —C$_3$-C$_{10}$ heterocycloalkyl, wherein the alkyl and cycloalkyl groups are optionally substituted 1-5 times with halo;

Cy is

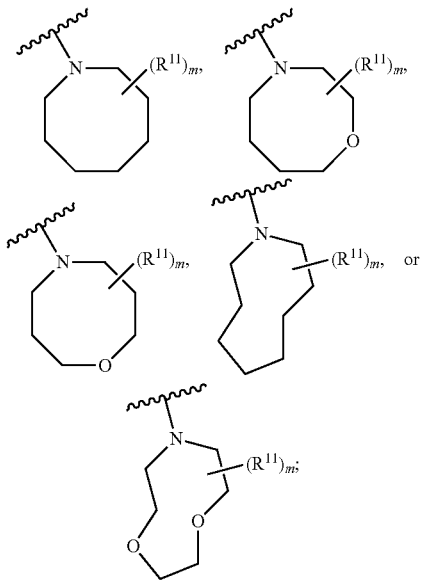

wherein

R$^{11}$ is, independently at each occurrence, —OH or halo;

m is 0, 1 or 2; and x is 0, 1, 2, or 3.

In still another embodiment of Formula I provided herein, or a pharmaceutically acceptable salt thereof, R⁴ is H;

each R¹ is, independently at each occurrence, —OH or halo;

R² is selected from —OH, halo, and —C₁-C₆ alkyl, wherein the alkyl group is optionally substituted 1-5 times with halo;

Cy is

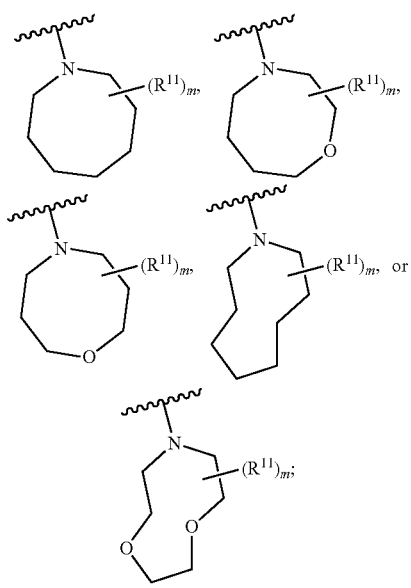

wherein

R¹¹ is, independently at each occurrence, —OH, halo, —C₁-C₆ alkyl, —C₁-C₆ heteroalkyl, —C₃-C₁₀ cycloalkyl, or —C₃-C₁₀ heterocycloalkyl;

m is 0, 1 or 2; and x is 0, 1, 2, or 3.

In another embodiment of Formula I provided herein, or a pharmaceutically acceptable salt thereof, R⁴ is H;

each R¹ is, independently at each occurrence, —OH or halo;

R² is selected from halo and —C₁-C₃ alkyl, wherein the alkyl group is optionally substituted 1-3 times with halo;

Cy is

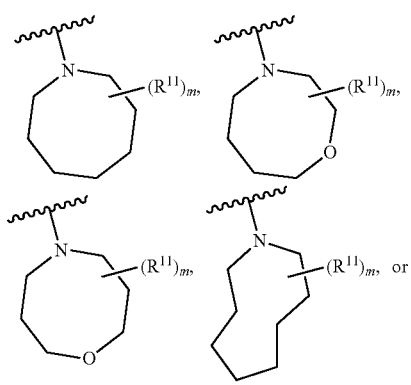

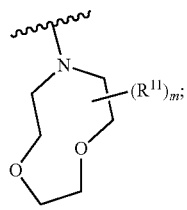

wherein

R¹¹ is, independently at each occurrence, —OH, halo, —C₁-C₃ alkyl, —C₁-C₄ heteroalkyl, —C₃-C₇ cycloalkyl, or —C₃-C₇ heterocycloalkyl;

m is 0, 1 or 2; and x is 0, 1, 2, or 3.

In yet another embodiment of Formula I provided herein, or a pharmaceutically acceptable salt thereof, R⁴ is H;

each R¹ is, independently at each occurrence, halo;

R² is selected from halo and —C₁ alkyl, wherein the alkyl group is optionally substituted 1-3 times with halo;

Cy is

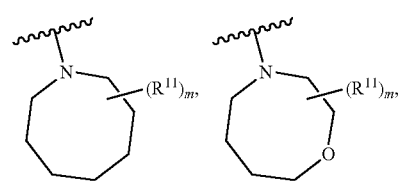

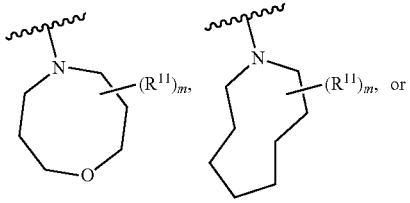

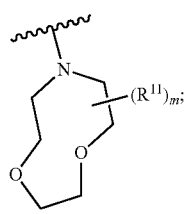

wherein

R¹¹ is, independently at each occurrence, —OH, halo, —C₁-C₃ alkyl, or —C₃-C₇ cycloalkyl;

m is 0, 1 or 2; and x is 2 or 3.

In still another embodiment of Formula I provided herein, or a pharmaceutically acceptable salt thereof, R⁴ is H;

each R¹ is, independently at each occurrence, halo;

R² is selected from halo and —C₁ alkyl, wherein the alkyl group is optionally substituted 1-3 times with halo;

Cy is

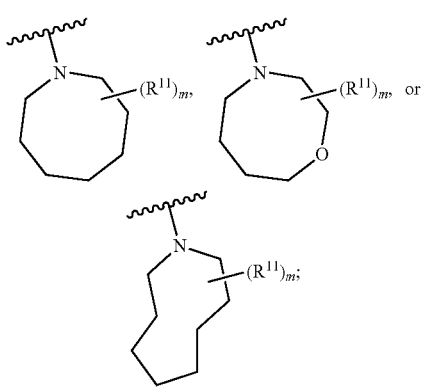

wherein
R[11] is, independently at each occurrence, —OH, halo, —C$_1$-C$_3$ alkyl, or —C$_3$-C$_7$ cycloalkyl;
m is 0, 1 or 2; and
x is 2 or 3.

In another embodiment of Formula I provided herein, the compound is selected from:

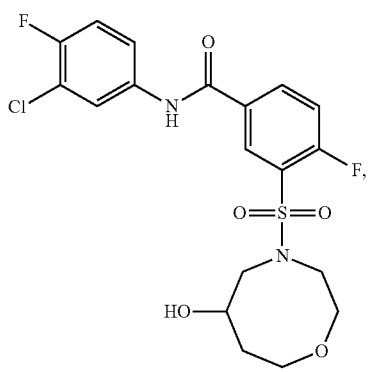

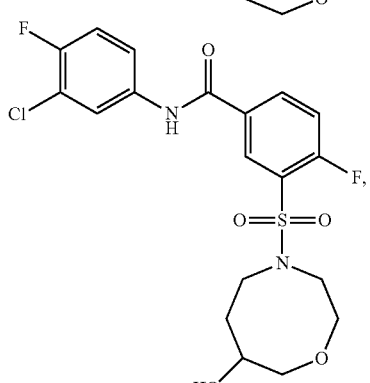

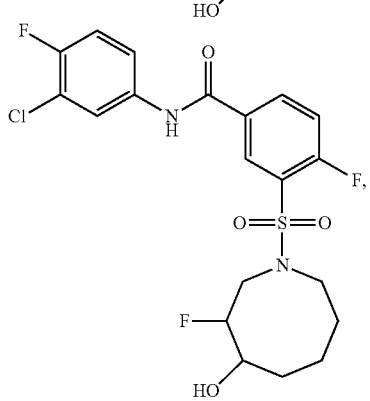

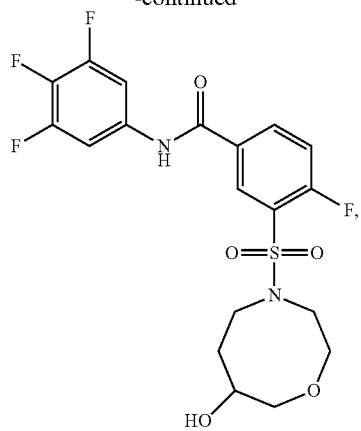

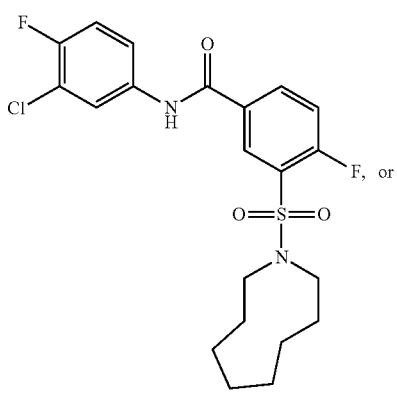

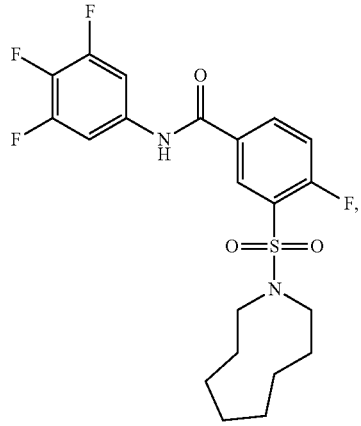

or a pharmaceutically acceptable salt thereof.

Certain preferred embodiments of Formula I, including pharmaceutically acceptable salts thereof, are shown below in Table 1. All compounds of Formula I, as well as pharmaceutically acceptable salts thereof, and the compounds of Table 1, as well as pharmaceutically acceptable salts thereof, are considered to be "compounds of the invention."

Synthetic method codes refer to the synthesis methodologies provided in the experimental section. For example, "A01B01C01" refers the use of intermediate A01 for region A, intermediate B01 for region B, and intermediate C01 for region C.

TABLE 1

| Structure | Compound ID | ¹H NMR | MS (M + H)⁺ | Synthetic method |
|---|---|---|---|---|
| 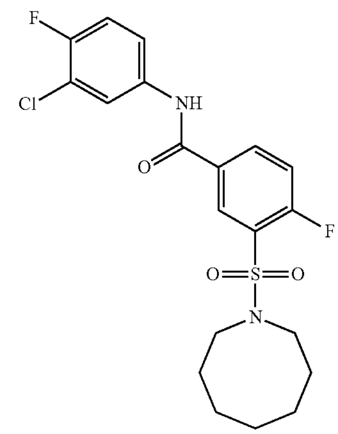 [SMILES: O=C(Nc1ccc(F)c(Cl)c1)c1ccc(F)c(S(=O)(=O)N2CCCCCCC2)c1] | 2037 | | 443/445 | A01B01C01 |
| 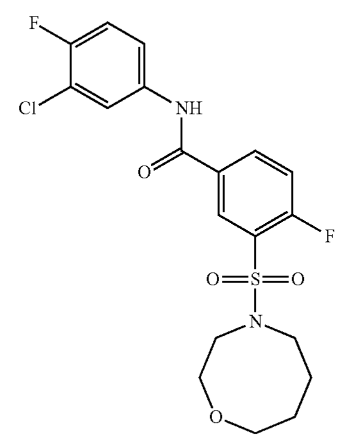 [SMILES: O=C(Nc1ccc(F)c(Cl)c1)c1ccc(F)c(S(=O)(=O)N2CCCCOCC2)c1] | 2038 | | 445/447 | A16B01C01 |
| 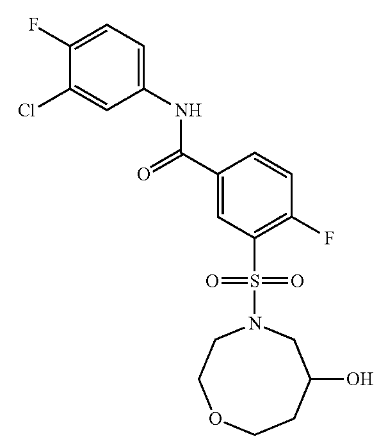 [SMILES: O=C(Nc1ccc(F)c(Cl)c1)c1ccc(F)c(S(=O)(=O)N2CCOCCC(O)C2)c1] | 2039 | ¹H NMR (400 MHz, MeOD) δ 8.46 (dd, J = 2.3, 6.5 Hz, 1H), 8.24 (m, 1H), 7.95 (dd, J = 2.5, 6.5 Hz, 1H), 7.66-7.57 (m, 1H), 7.50 (t, J = 9.3 Hz, 1H), 7.24 (t, J = 9.0 Hz, 1H), 4.01-4.17 (m, 2H), 3.79-3.87 (m, 1H), 3.56-3.77 (m, 4H), 3.10-3.23 (m, 2H), 2.18-2.29 (m, 1H), 1.68-1.79 (m, 1H). | 461/463 | A17B01C01 |

TABLE 1-continued

| Structure | Compound ID | ¹H NMR | MS (M + H)⁺ | Synthetic method |
|---|---|---|---|---|
| 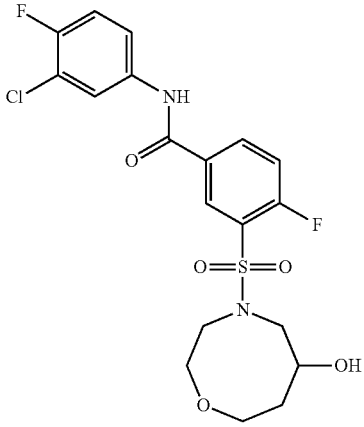 [SMILES: O=C(Nc1ccc(F)c(Cl)c1)c1ccc(F)c(S(=O)(=O)N2CCOCCC(O)C2)c1] | 2039_E1 | ¹H NMR (400 MHz, MeOD) δ 8.46 (d, J = 5.3 Hz, 1H), 8.24 (brs, 1H), 7.96 (d, J = 5.3 Hz, 1H), 7.61 (brs, 1H), 7.51 (t, J = 8.8 Hz, 1H), 7.25 (t, J = 8.3 Hz, 1H), 3.97-4.22 (m, 2H), 3.51-3.92 (m, 5H), 3.06-3.25 (m, 2H), 2.23 (brs, 1H), 1.75 (brs, 1H). | 461/463 | A17B01C01 Enantiomers were separated by SUPER-CRITICAL FLUID CHOMATO-GRAPHY: AD-3S_2_5_40_3 ML_T35.M |
| 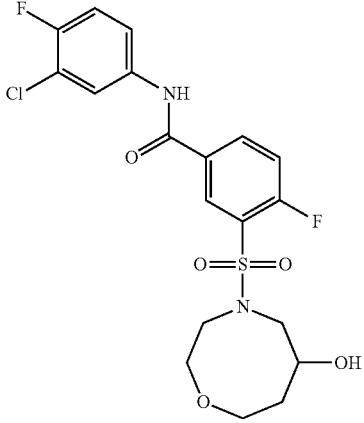 [SMILES: O=C(Nc1ccc(F)c(Cl)c1)c1ccc(F)c(S(=O)(=O)N2CCOCCC(O)C2)c1] | 2039_E2 | ¹H NMR (400 MHz, MeOD) δ 8.46 (dd, J = 2.3, 6.5 Hz, 1H), 8.20-8.30 (m, 1H), 7.96 (dd, J = 2.4, 6.7 Hz, 1H), 7.59-7.65 (m, 1H), 7.51 (t, J = 9.4 Hz, 1H), 7.25 (t, J = 8.9 Hz, 1H), 4.02-4.19 (m, 2H), 3.80-3.87 (m, 1H), 3.55-3.78 (m, 4H), 3.09-3.22 (m, 2H), 2.17-2.30 (m, 1H), 1.67-1.79 (m, 1H). | 461/463 | A17B01C01 Enantiomers were separated by SUPER-CRITICAL FLUID CHOMATO-GRAPHY: AD-3S_2_5_40_3 ML_T35.M |
| 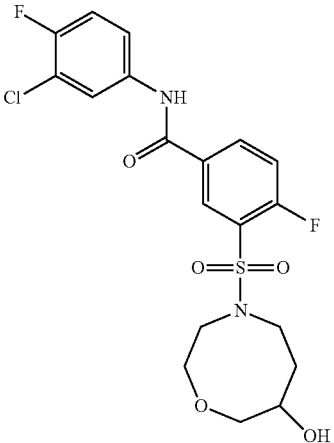 [SMILES: O=C(Nc1ccc(F)c(Cl)c1)c1ccc(F)c(S(=O)(=O)N2CCOCC(O)CC2)c1] | 2040 | ¹H NMR (400 MHz, MeOD) δ 8.44 (dd, J = 2.0, 6.5 Hz, 1H), 8.24 (m, 1H), 7.96 (dd, J = 2.5, 6.5 Hz, 1H), 7.56-7.66 (m, 1H), 7.49 (t, J = 9.3 Hz, 1H), 7.25 (t, J = 8.9 Hz, 1H), 3.71-3.98 (m, 5H), 3.39-3.54 (m, 3H), 3.32-3.37 (m, 1H), 1.95-2.15 (m, 2H). | 461/463 | A18B01C01 |

TABLE 1-continued

| Structure | Compound ID | ¹H NMR | MS (M + H)+ | Synthetic method |
|---|---|---|---|---|
| | 2040_E1 | ¹H NMR (400 MHz, MeOD) δ 8.44 (dd, J = 2.0, 6.5 Hz, 1H), 8.18-8.28 (m, 1H), 7.96 (dd, J = 2.5, 6.5 Hz, 1H), 7.57-7.67 (m, 1H), 7.50 (t, J = 9.3 Hz, 1H), 7.25 (t, J = 8.9 Hz, 1H), 3.71-3.99 (m, 5H), 3.39-3.54 (m, 3H), 3.35 (brs, 1H), 1.90-2.17 (m, 2H). | 461/463 | A18B01C01 Enantiomers were separated by SUPER-CRITICAL FLUID CHOMATO-GRAPHY: AD-3S_2_5_40_3 ML_T35.M |
| | 2040_E1 | ¹H NMR (400 MHz, MeOD) δ 8.44 (dd, J = 2.0, 6.5 Hz, 1H), 8.19-8.29 (m, 1H), 7.96 (dd, J = 2.5, 6.8 Hz, 1H), 7.57-7.66 (m, 1H), 7.50 (t, J = 9.3 Hz, 1H), 7.25 (t, J = 9.0 Hz, 1H), 3.71-3.98 (m, 5H), 3.42-3.54 (m, 3H), 3.35 (brs, 1H), 1.94-2.15 (m, 2H). | 461/463 | A18B01C01 Enantiomers were separated by SUPER-CRITICAL FLUID CHOMATO-GRAPHY: AD-3S_2_5_40_3 ML_T35.M |
| 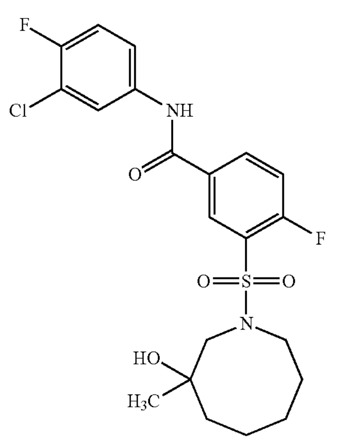 [SMILES: CC1(O)CCCCCN(S(=O)(=O)c2cc(C(=O)Nc3ccc(F)c(Cl)c3)ccc2F)C1] | 2060 | | 473/475 | A03B01C01 |

TABLE 1-continued

| Structure | Compound ID | $^1$H NMR | MS (M + H)$^+$ | Synthetic method |
|---|---|---|---|---|
| 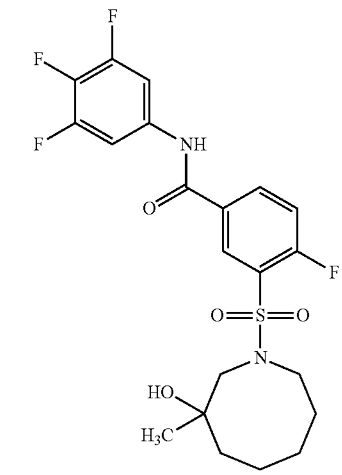 [SMILES: CC1(O)CCCCCN(S(=O)(=O)c2cc(C(=O)Nc3cc(F)c(F)c(F)c3)ccc2F)C1] | 2070 | $^1$H NMR (400 MHz, MeOD) δ 8.46 (d, J = 6.5 Hz, 1H), 8.22-8.30 (m, 1H), 7.47-7.67 (m, 3H), 3.35-3.43 (m, 3H), 3.06-3.19 (m, 1H), 1.50-1.93 (m, 8H), 1.26 (s, 3H). | 475 | A03B01C02 |
| 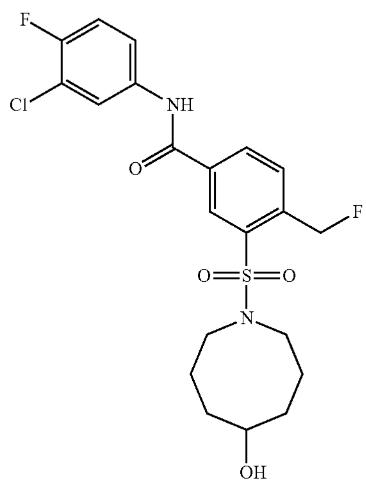 [SMILES: O=C(Nc1ccc(F)c(Cl)c1)c1ccc(CF)c(S(=O)(=O)N2CCCC(O)CCC2)c1] | 2227 | | 455/457 (m − 18)$^+$ | A15B02C01 |
| 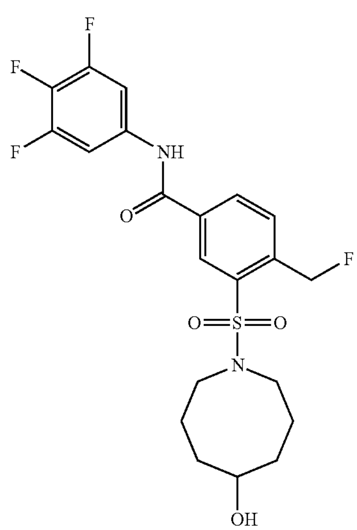 [SMILES: O=C(Nc1cc(F)c(F)c(F)c1)c1ccc(CF)c(S(=O)(=O)N2CCCC(O)CCC2)c1] | 2228 | $^1$H NMR (400 MHz, MeOD) δ 8.19-8.30 (m, 2H), 7.91 (d, J = 8.0 Hz, 1H), 7.57-7.68 (m, 2H), 5.78-5.98 (m, 2H), 3.98-4.11 (m, 1H), 3.39-3.49 (m, 2H), 3.21-3.30 (m, 2H), 1.66-2.03 (m, 8H). | 475 | A15B02C02 |

TABLE 1-continued

| Structure | Compound ID | ¹H NMR | MS (M + H)⁺ | Synthetic method |
|---|---|---|---|---|
| 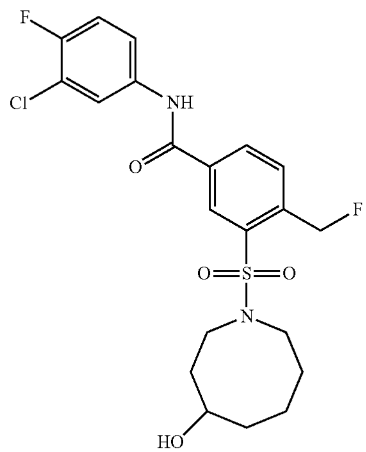 [SMILES: O=C(Nc1ccc(F)c(Cl)c1)c1ccc(CF)c(S(=O)(=O)N2CCCCC(O)CC2)c1] | 2229 | ¹H NMR (400 MHz, MeOD) δ 8.22-8.30 (m, 2H), 7.90-8.01 (m, 2H), 7.63-7.65 (m, 1H), 7.24-7.31 (m, 1H), 5.97 (s, 1H), 5.81 (s, 1H), 3.85-3.95 (m, 1H), 3.40-3.50 (m, 4H), 1.78-2.00 (m, 8H). | 473/475 | A04B02C01 |
| 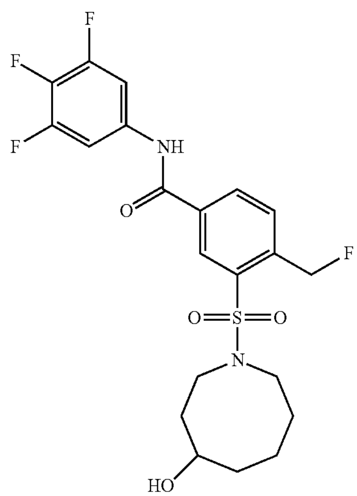 [SMILES: O=C(Nc1cc(F)c(F)c(F)c1)c1ccc(CF)c(S(=O)(=O)N2CCCCC(O)CC2)c1] | 2230 | | 475 | A15B02C02 |
| 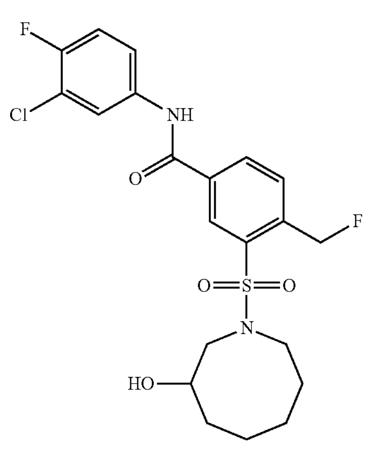 [SMILES: O=C(Nc1ccc(F)c(Cl)c1)c1ccc(CF)c(S(=O)(=O)N2CCCCCC(O)C2)c1] | 2231 | | 473/475 | A02B02C01 |

TABLE 1-continued

| Structure | Compound ID | ¹H NMR | MS (M + H)⁺ | Synthetic method |
|---|---|---|---|---|
| 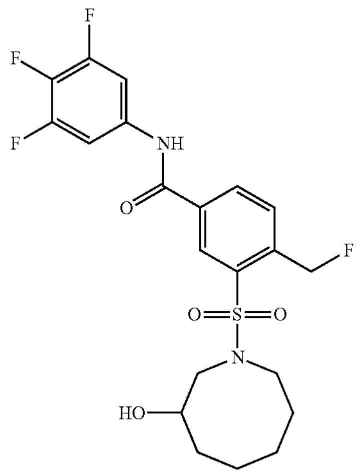 [SMILES: O=C(Nc1cc(F)c(F)c(F)c1)c1ccc(CF)c(S(=O)(=O)N2CCCCCC(O)C2)c1] | 2232 | | 475 | A02B02C02 |
| 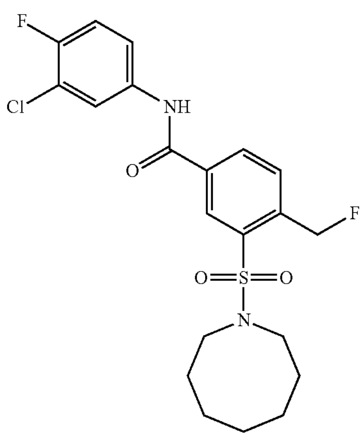 [SMILES: O=C(Nc1ccc(F)c(Cl)c1)c1ccc(CF)c(S(=O)(=O)N2CCCCCCC2)c1] | 2233 | | 457/459 | A01B02C01 |
| 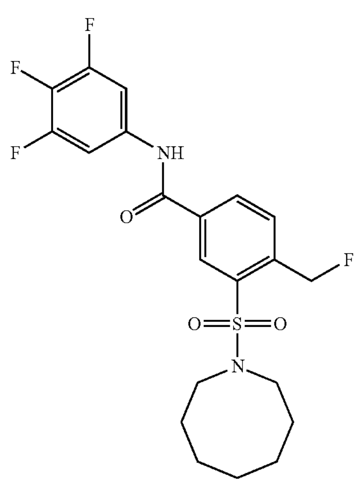 [SMILES: O=C(Nc1cc(F)c(F)c(F)c1)c1ccc(CF)c(S(=O)(=O)N2CCCCCCC2)c1] | 2234 | | 459 | A02B02C02 |

TABLE 1-continued
| Structure | Compound ID | ¹H NMR | MS (M + H)⁺ | Synthetic method |
|---|---|---|---|---|
| 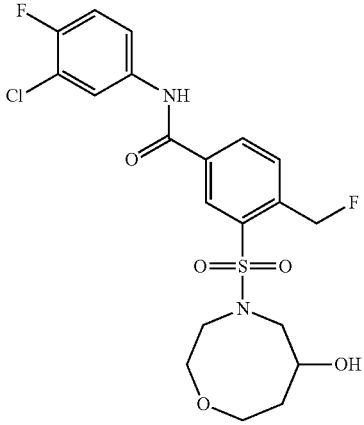 [SMILES: O=C(Nc1ccc(F)c(Cl)c1)c1ccc(CF)c(S(=O)(=O)N2CCOCCC(O)C2)c1] | 2237 | | 475/477 | A17B02C01 |
| 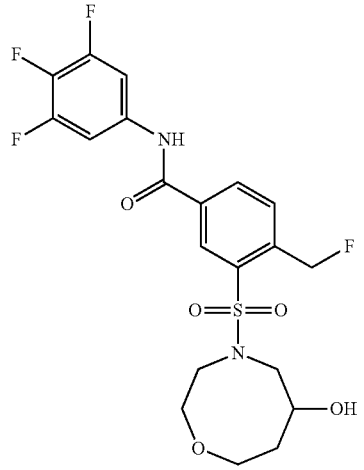 | 2238 | | 477 | A17B02C02 |
| 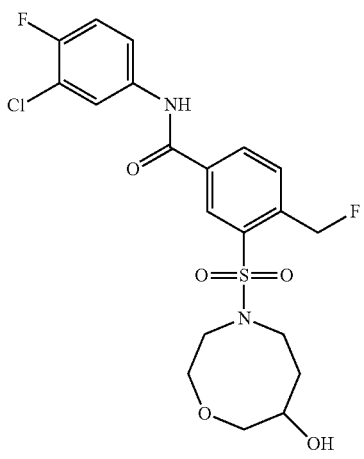 [SMILES: O=C(Nc1ccc(F)c(Cl)c1)c1ccc(CF)c(S(=O)(=O)N2CCOCC(O)CC2)c1] | 2239 | | 475/477 | A18B02C01 |

TABLE 1-continued

| Structure | Compound ID | $^1$H NMR | MS (M + H)$^+$ | Synthetic method |
|---|---|---|---|---|
| 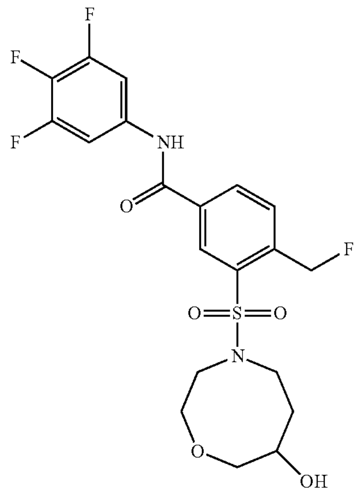 [SMILES: O=C(Nc1cc(F)c(F)c(F)c1)c1ccc(CF)c(S(=O)(=O)N2CCOCC(O)CC2)c1] | 2240 |  | 477 | A18B02C02 |
| 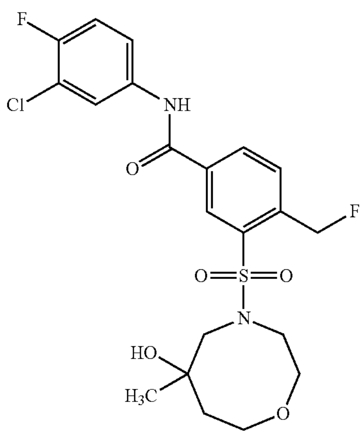 [SMILES: CC1(O)CCOCCN(S(=O)(=O)c2cc(C(=O)Nc3ccc(F)c(Cl)c3)ccc2CF)C1] | 2241 |  | 471/473 (M − 18)$^+$ | A19B02C01 |
| 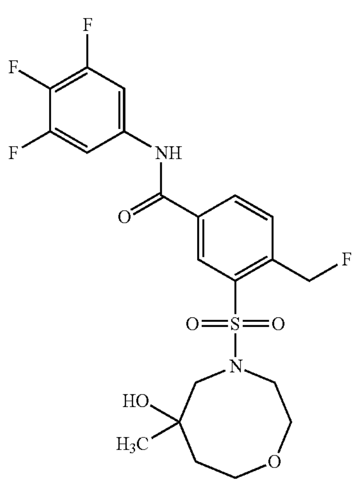 [SMILES: CC1(O)CCOCCN(S(=O)(=O)c2cc(C(=O)Nc3cc(F)c(F)c(F)c3)ccc2CF)C1] | 2242 | $^1$H NMR (400 MHz, MeOD) δ 8.32-8.37 (m, 1 H), 8.20-8.27 (m, 1 H), 7.89-7.94 (m, 1 H), 7.56-7.66 (m, 2 H), 5.94-5.98 (m, 1 H), 5.82-5.86 (m, 1 H), 3.64-3.85 (m, 4 H), 3.54-3.61 (m, 1 H), 3.37-3.51 (m, 2 H), 3.16-3.25 (m, 1 H), 2.07-2.17 (m, 1 H), 1.67-1.77 (m, 1 H), 1.26 (s, 3 H). | 473/513 (M − 18)$^+$/ (M + 23)$^+$ | A19B02C02 |

TABLE 1-continued

| Structure | Compound ID | ¹H NMR | MS (M + H)⁺ | Synthetic method |
|---|---|---|---|---|
| 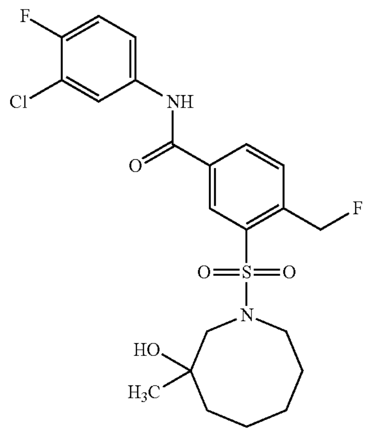 [SMILES: CC1(O)CCCCCN(S(=O)(=O)c2cc(C(=O)Nc3ccc(F)c(Cl)c3)ccc2CF)C1] | 2249 | | 469/471 (M − 18)⁺ | A03B02C01 |
| 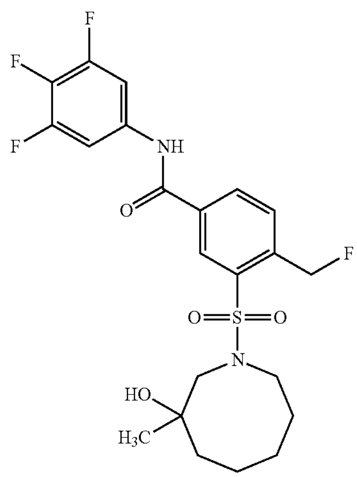 [SMILES: CC1(O)CCCCCN(S(=O)(=O)c2cc(C(=O)Nc3cc(F)c(F)c(F)c3)ccc2CF)C1] | 2250 | | 471 (M − 18)⁺ | A03B02C02 |
| 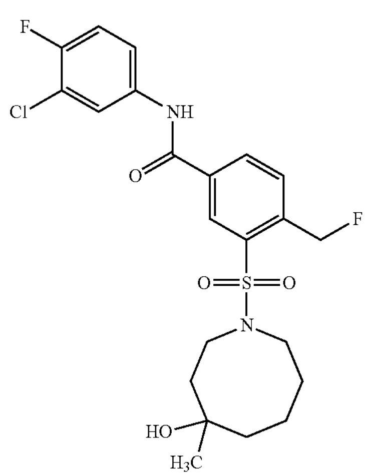 [SMILES: CC1(O)CCCCN(S(=O)(=O)c2cc(C(=O)Nc3ccc(F)c(Cl)c3)ccc2CF)CC1] | 2253 | | 469/471 (M − 18)⁺ | A05B02C01 |

TABLE 1-continued

| Structure | Compound ID | ¹H NMR | MS (M + H)⁺ | Synthetic method |
|---|---|---|---|---|
| 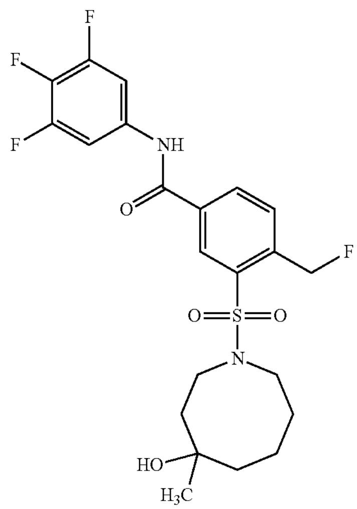 [SMILES: CC1(O)CCCCN(S(=O)(=O)c2cc(C(=O)Nc3cc(F)c(F)c(F)c3)ccc2CF)CC1] | 2254 | | 471 (M − 18)⁺ | A05B02C02 |
| 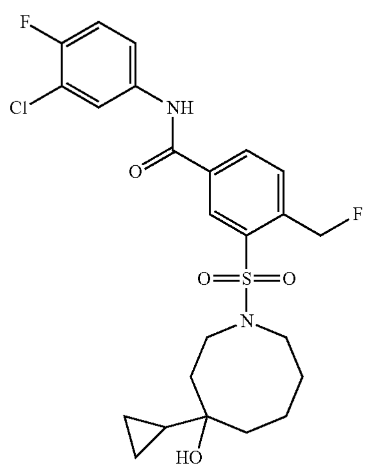 [SMILES: O=C(Nc1ccc(F)c(Cl)c1)c1ccc(CF)c(S(=O)(=O)N2CCCCC(O)(C3CC3)CC2)c1] | 2255 | | 495/497 (M − 18)⁺ | A06B02C01 |
| 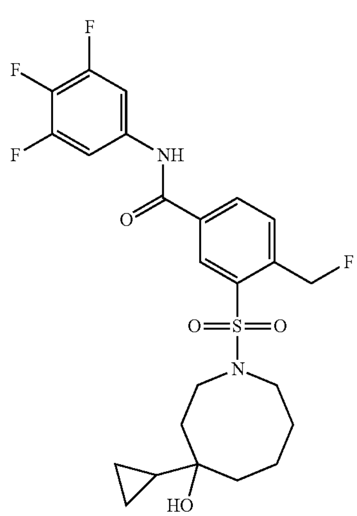 [SMILES: O=C(Nc1cc(F)c(F)c(F)c1)c1ccc(CF)c(S(=O)(=O)N2CCCCC(O)(C3CC3)CC2)c1] | 2256 | | 497 (M − 18)⁺ | A06B02C02 |

TABLE 1-continued

| Structure | Compound ID | ¹H NMR | MS (M + H)⁺ | Synthetic method |
|---|---|---|---|---|
| 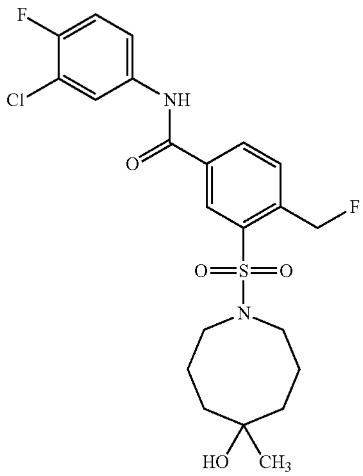 [SMILES: CC1(O)CCCN(S(=O)(=O)c2cc(C(=O)Nc3ccc(F)c(Cl)c3)ccc2CF)CCC1] | 2257 | | 469/471 (M − 18)⁺ | A08B02C01 |
| 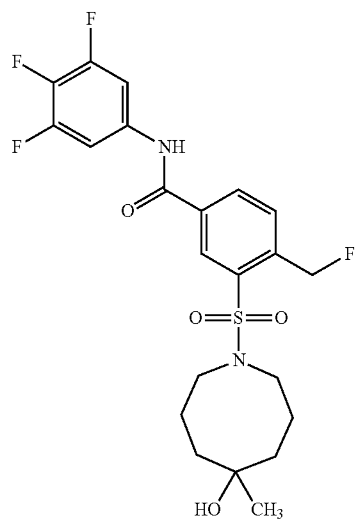 [SMILES: CC1(O)CCCN(S(=O)(=O)c2cc(C(=O)Nc3cc(F)c(F)c(F)c3)ccc2CF)CCC1] | 2258 | | 471 (M − 18)⁺ | A08B02C02 |
| 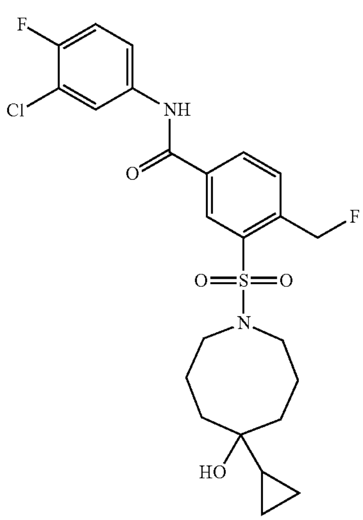 [SMILES: O=C(Nc1ccc(F)c(Cl)c1)c1ccc(CF)c(S(=O)(=O)N2CCCC(O)(C3CC3)CCC2)c1] | 2259 | | 495/497 (M − 18)⁺ | A09B02C01 |

TABLE 1-continued

| Structure | Compound ID | ¹H NMR | MS (M + H)⁺ | Synthetic method |
|---|---|---|---|---|
| 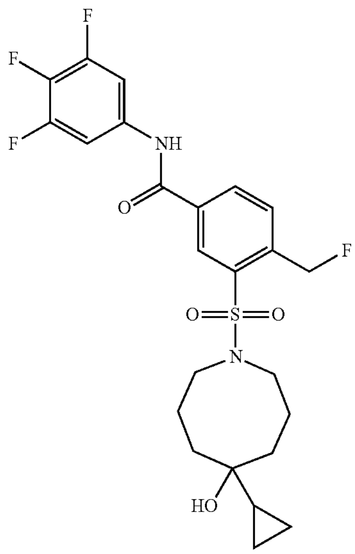 [SMILES: O=C(Nc1cc(F)c(F)c(F)c1)c1ccc(CF)c(S(=O)(=O)N2CCCC(O)(C3CC3)CCC2)c1] | 2260 | ¹H NMR (400 MHz, MeOD) δ 8.29 (s, 1 H), 8.22 (dd, J = 8.1, 1.6 Hz, 1 H), 7.91 (d, J = 8.0 Hz, 1 H), 7.56-7.66 (m, 2 H), 5.77-5.98 (m, 2 H), 3.34-3.52 (m, 4 H), 1.64-2.06 (m, 8 H), 0.92-1.10 (m, 1 H), 0.26-0.46 (m, 4 H). | 497 (M − 18)⁺ | A09B02C02 |
| 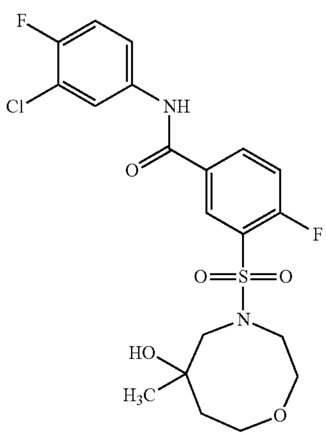 [SMILES: CC1(O)CCOCCN(S(=O)(=O)c2cc(C(=O)Nc3ccc(F)c(Cl)c3)ccc2F)C1] | 2261 |  | 457/459 (M − 18)⁺ | A19B01C01 |
| 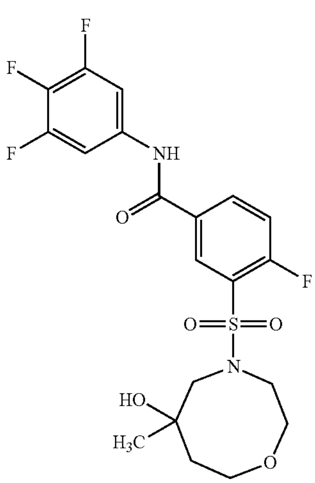 [SMILES: CC1(O)CCOCCN(S(=O)(=O)c2cc(C(=O)Nc3cc(F)c(F)c(F)c3)ccc2F)C1] | 2262 |  | 459/499 (M − 18)⁺/ (M + 23)⁺ | A19B01C02 |

TABLE 1-continued

| Structure | Compound ID | ¹H NMR | MS (M + H)⁺ | Synthetic method |
|---|---|---|---|---|
| 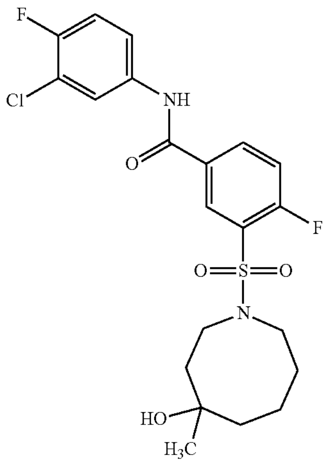 [SMILES: CC1(O)CCCCN(S(=O)(=O)c2cc(C(=O)Nc3ccc(F)c(Cl)c3)ccc2F)CC1] | 2273 | ¹H NMR (400 MHz, MeOD) δ 8.39-8.48 (m, 1 H), 8.18-8.27 (m, 1 H), 7.93-8.01 (m, 1 H), 7.57-7.67 (m, 1 H), 7.45-7.52 (m, 1 H), 7.20-7.31 (m, 1 H), 3.41-3.63 (m, 2 H), 3.03-3.15 (m, 2 H), 1.98-2.13 (m, 1 H), 1.87-1.97 (m, 2 H), 1.48-1.86 (m, 5 H), 1.27 (s, 3 H). | 455/457 (M − 18)⁺ | A05B01C01 |
| 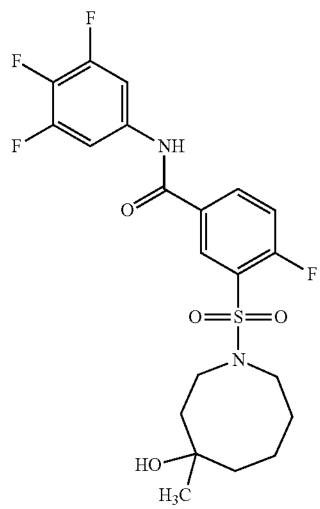 [SMILES: CC1(O)CCCCN(S(=O)(=O)c2cc(C(=O)Nc3cc(F)c(F)c(F)c3)ccc2F)CC1] | 2274 | | 457 (M − 18)⁺ | A05B01C02 |
| 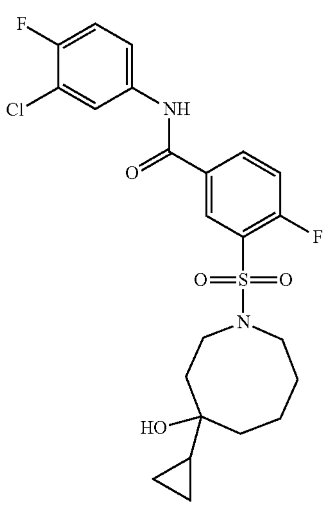 [SMILES: O=C(Nc1ccc(F)c(Cl)c1)c1ccc(F)c(S(=O)(=O)N2CCCCC(O)(C3CC3)CC2)c1] | 2275 | | 481/483 (M − 18)⁻ | A06B01C01 |

TABLE 1-continued

| Structure | Compound ID | ¹H NMR | MS (M + H)⁺ | Synthetic method |
|---|---|---|---|---|
| 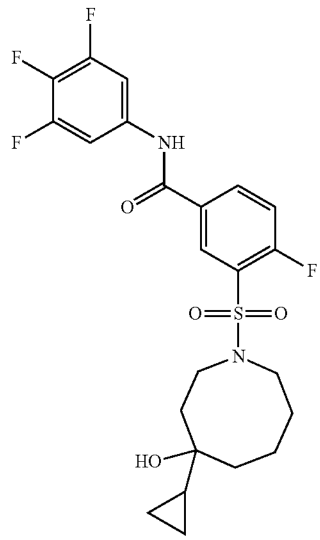 [SMILES: O=C(Nc1cc(F)c(F)c(F)c1)c1ccc(F)c(S(=O)(=O)N2CCCCC(O)(C3CC3)CC2)c1] | 2276 | ¹H NMR (400 MHz, MeOD) δ 8.38-8.50 (m, 1 H), 8.20-8.27 (m, 1 H), 7.55-7.65 (m, 2 H), 7.45-7.54 (m, 1 H), 3.50-3.73 (m, 2 H), 3.00-3.19 (m, 2 H), 1.96-2.13 (m, 2 H), 1.59-1.94 (m, 6 H), 1.04-1.19 (m, 1 H), 0.41-0.51 (m, 1H), 0.26-0.40 (m, 3 H). | 483 (M − 18)⁺ | A06B01C02 |
| 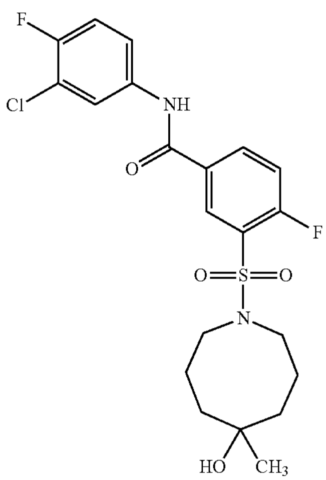 [SMILES: CC1(O)CCCN(S(=O)(=O)c2cc(C(=O)Nc3ccc(F)c(Cl)c3)ccc2F)CCC1] | 2277 | ¹H NMR (400 MHz, MeOD) δ 10.68 (s, 1 H), 8.39-8.40 (m, 1 H), 8.35-8.37 (m, 1 H), 8.03-8.06 (m, 1 H), 7.68-7.71 (m, 2 H), 7.43-7.48 (m, 1 H), 4.21 (s, 1 H), 3.18-3.34 (m, 4 H), 1.53-1.79 (m, 8 H), 1.10 (s, 3 H). | 455/457 (M − 18)⁺ | A08B01C01 |
| 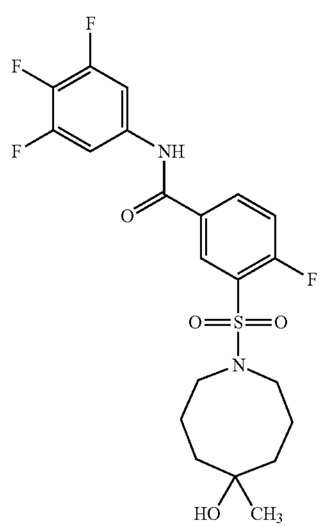 [SMILES: CC1(O)CCCN(S(=O)(=O)c2cc(C(=O)Nc3cc(F)c(F)c(F)c3)ccc2F)CCC1] | 2278 | | 457 (M − 18)⁺ | A08B01C02 |

TABLE 1-continued
| Structure | Compound ID | ¹H NMR | MS (M + H)⁺ | Synthetic method |
|---|---|---|---|---|
| 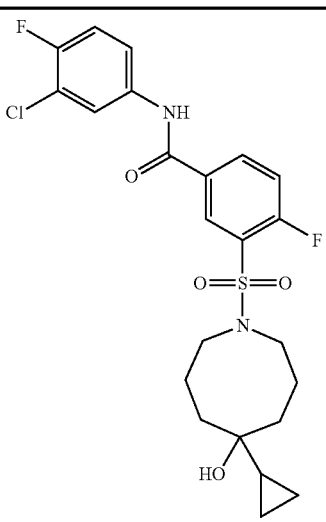 | 2279 | ¹H NMR (400 MHz, MeOD) δ 8.44-8.47 (m, 1 H), 8.23-8.29 (m, 1 H), 7.97-7.99 (m, 1 H), 7.55-7.65 (m, 1 H), 7.48-7.53 (m, 1 H), 7.25-7.29 (m, 1 H), 3.25-3.50 (m, 4 H), 1.76-1.96 (m, 8 H), 0.98-1.02 (m, 1 H), 0.33-0.41 (m, 4 H). | 481/483 (M − 18)⁺ | A09B01C01 |
| 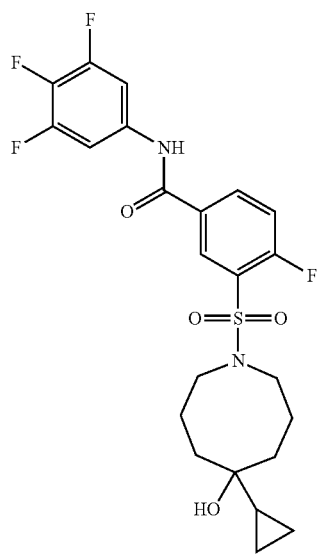 [SMILES: O=C(Nc1cc(F)c(F)c(F)c1)c1ccc(F)c(S(=O)(=O)N2CCCC(O)(C3CC3)CCC2)c1] | 2280 | | 483 (M − 18)⁺ | A09B01C02 |
| 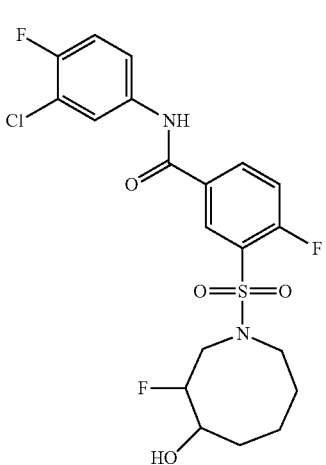 [SMILES: O=C(Nc1ccc(F)c(Cl)c1)c1ccc(F)c(S(=O)(=O)N2CCCCC(O)C(F)C2)c1] | 2285_D1 | ¹H NMR (400 MHz, MeOD) δ 8.46-8.52 (m, 1 H), 8.23-8.32 (m, 1 H), 7.95-8.02 (m, 1 H), 7.61-7.68 (m, 1 H), 7.49-7.59 (m, 1 H), 7.21-7.32 (m, 1 H), 4.39-4.65 (m, 1 H) 3.71-3.89 (m, 2 H), 3.49-3.61 (m, 1 H), 3.34-3.42 (m, 2 H), 3.10 (d, J = 13.6 Hz, 1 H), 1.69-2.06 (m, 6 H). | 477/479 | A14B01C01 |

TABLE 1-continued

| Structure | Compound ID | ¹H NMR | MS (M + H)⁺ | Synthetic method |
|---|---|---|---|---|
| 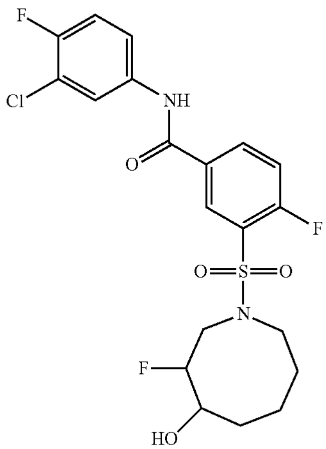 [SMILES: O=C(Nc1ccc(F)c(Cl)c1)c1ccc(F)c(S(=O)(=O)N2CCCCC(O)C(F)C2)c1] | 2285_D2 | ¹H NMR (400 MHz, MeOD) δ 8.45-8.53 (m, 1 H), 8.23-8.32 (m, 1 H), 7.94-8.01 (m, 1 H), 7.61-7.69 (m, 1 H), 7.48-7.59 (m, 1 H), 7.22-7.31 (m, 1 H), 4.93-4.95 (m, 1 H), 4.75-4.86 (m, 1 H), 4.10-4.28 (m, 1 H), 3.68-3.82 (m, 1 H), 3.39-3.62 (m, 2 H), 2.98-3.13 (m, 1 H), 2.06 (s, 6 H). | 477/479 | A14B01C01 |
| 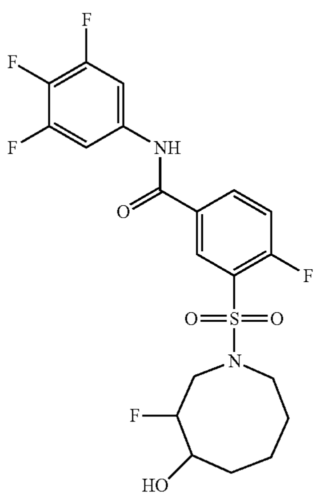 [SMILES: O=C(Nc1cc(F)c(F)c(F)c1)c1ccc(F)c(S(=O)(=O)N2CCCCC(O)C(F)C2)c1] | 2286_D1 | ¹H NMR (400 MHz, MeOD) δ 8.43-8.53 (m, 1 H), 8.23-8.34 (m, 1 H), 7.45-7.68 (m, 3 H), 4.41-4.65 (m, 1 H), 3.67-3.88 (m, 2 H), 3.50-3.59 (m, 1 H), 3.34-3.43 (m, 1 H), 3.04-3.17 (m, 1 H), 1.67-2.06 (m, 6 H). | 479 | A14B01C02 |
| 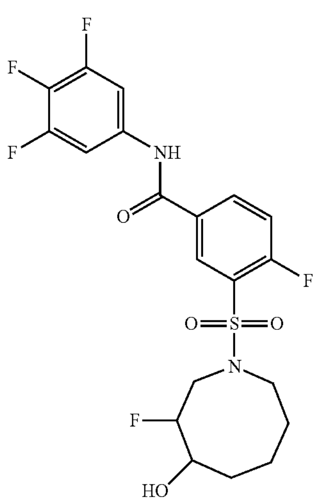 [SMILES: O=C(Nc1cc(F)c(F)c(F)c1)c1ccc(F)c(S(=O)(=O)N2CCCCC(O)C(F)C2)c1] | 2286_D2 | ¹H NMR (400 MHz, MeOD) δ 8.45-8.50 (m, 1 H), 8.24-8.31 (m, 1 H), 7.49-7.66 (m, 3 H), 4.78-4.83 (m, 1 H), 4.11-4.26 (m, 1 H), 3.67-3.78 (m, 1 H), 3.42-3.62 (m, 2 H), 3.03-3.13 (m, 1 H), 1.63-2.07 (m, 6 H). | 479 | A14B01C02 |

TABLE 1-continued

| Structure | Compound ID | ¹H NMR | MS (M + H)⁺ | Synthetic method |
|---|---|---|---|---|
| 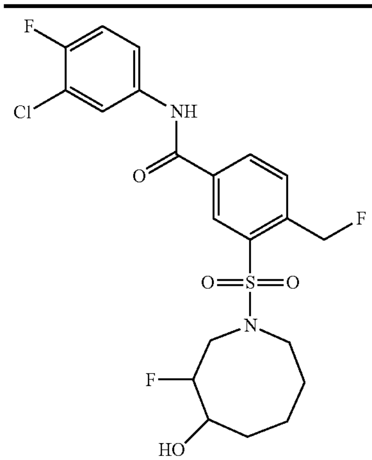 | 2287_D1 | | 491/493 | A14B02C01 |
| 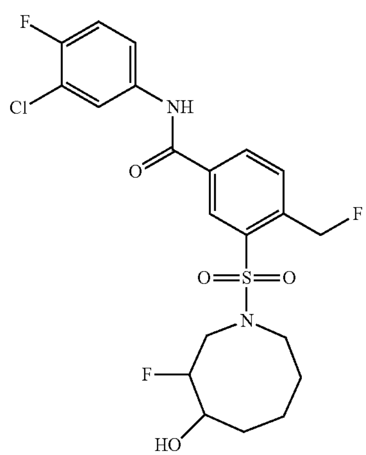 [SMILES: O=C(Nc1ccc(F)c(Cl)c1)c1ccc(CF)c(S(=O)(=O)N2CCCCC(O)C(F)C2)c1] | 2287_D2 | | 491/493 | A14B02C01 |
| 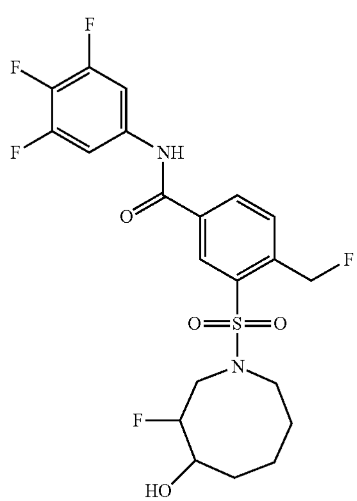 [SMILES: O=C(Nc1cc(F)c(F)c(F)c1)c1ccc(CF)c(S(=O)(=O)N2CCCCC(O)C(F)C2)c1] | 2288_D1 | | 493 | A14B02C02 |

TABLE 1-continued

| Structure | Compound ID | ¹H NMR | MS (M + H)⁺ | Synthetic method |
|---|---|---|---|---|
| (structure) | 2288_D2 | | 493 | A14B02C02 |
| (structure) | 2293_D1 | | 477/479 | A12B01C01 |
| (structure) | 2293_D2 | | 477/479 | A12B01C01 |

TABLE 1-continued
| Structure | Compound ID | ¹H NMR | MS (M + H)⁺ | Synthetic method |
|---|---|---|---|---|
| 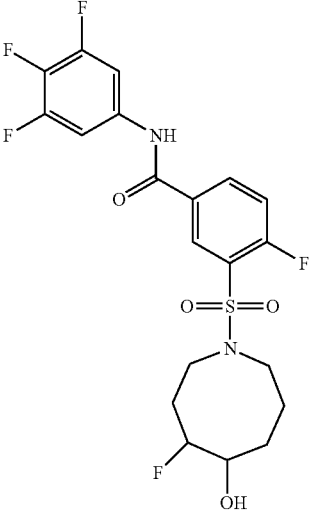 [SMILES: O=C(Nc1cc(F)c(F)c(F)c1)c1ccc(F)c(S(=O)(=O)N2CCCC(O)C(F)CC2)c1] | 2294_D1 | ¹H NMR (400 MHz, MeOD) δ 8.45-8.47 (m, 1 H), 8.24-8.26 (m, 1 H), 7.49-7.63 (m, 3 H), 4.53-4.65 (m, 1 H), 4.19-4.24 (m, 1 H), 3.74-3.76 (m, 1 H), 3.52-3.56 (m, 1 H), 3.03-3.09 (m, 2 H), 1.82-2.13 (m, 6 H). | 479 | A12B01C02 |
| 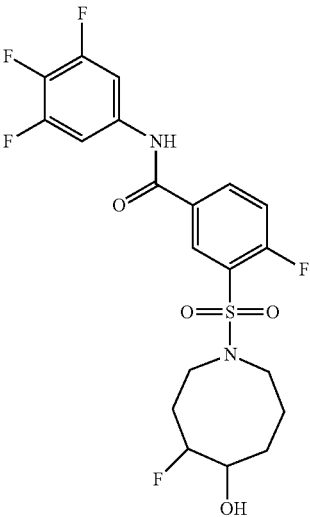 [SMILES: O=C(Nc1cc(F)c(F)c(F)c1)c1ccc(F)c(S(=O)(=O)N2CCCC(O)C(F)CC2)c1] | 2294_D2 | ¹H NMR (400 MHz, MeOD) δ 8.44-8.46 (m, 1 H), 8.23-8.26 (m, 1 H), 7.51-7.63 (m, 3 H), 4.79-4.92 (m, 1 H), 4.26-4.32 (m, 1 H), 3.57-3.66 (m, 2 H), 3.10-3.20 (m, 1 H), 2.99-3.04 (m, 1 H), 1.75-2.30 (m, 6 H). | 479 | A12B01C02 |
| 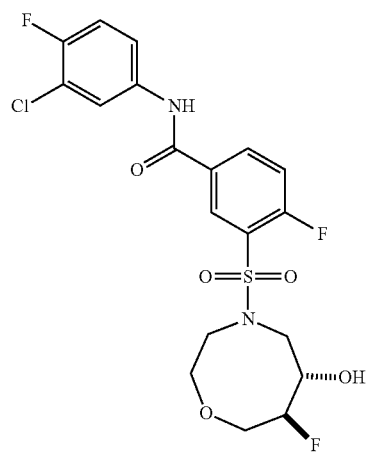 [SMILES: O=C(Nc1ccc(F)c(Cl)c1)c1ccc(F)c(S(=O)(=O)N2CCOC[C@H](F)[C@@H](O)C2)c1] | 2297_Trans1 | ¹H NMR (400 MHz, MeOD) δ 8.47 (dd, J = 2.0, 6.5 Hz, 1 H), 8.22-8.32 (m, 1 H), 7.97 (dd, J = 2.5, 6.5 Hz, 1 H), 7.67-7.58 (m, 1 H), 7.53 (t, J = 9.3 Hz, 1 H), 7.25 (t, J = 8.9 Hz, 1 H), 4.28-4.48 (m, 1 H), 4.08-4.26 (m, 2 H), 4.01 (dt, J = 5.8, 12.3 Hz, 1 H), 3.70-3.90 (m, 2 H), 3.44-3.59 (m, 2 H), 3.33-3.37 (m, 1 H), 3.27 (brs, 1 H). | 479/481 | A21B01C01 Regiomers were separated by SUPER-CRITICAL FLUID CHOMATO-GRAPHY: AD-3S_5_5_40_3 ML_T35.M |

TABLE 1-continued

| Structure | Compound ID | ¹H NMR | MS (M + H)+ | Synthetic method |
|---|---|---|---|---|
| 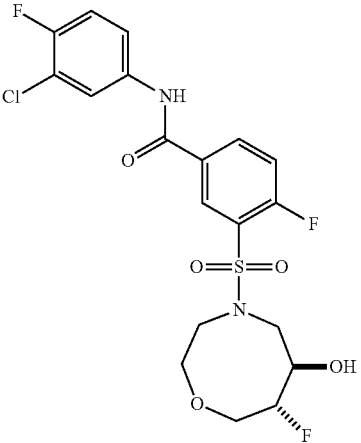 [SMILES: O=C(Nc1ccc(F)c(Cl)c1)c1ccc(F)c(S(=O)(=O)N2CCOC[C@@H](F)[C@H](O)C2)c1] | 2297_Trans2 | ¹H NMR (400 MHz, MeOD) δ 8.47 (dd, J = 2.0, 6.5 Hz, 1 H), 8.26 (dt, J = 2.3, 5.4 Hz, 1 H), 7.96 (dd, J = 2.5, 6.5 Hz, 1 H), 7.62 (td, J = 3.3, 8.9 Hz, 1 H), 7.52 (t, J = 9.4 Hz, 1 H), 7.25 (t, J = 9.0 Hz, 1 H), 4.28-4.48 (m, 1 H), 4.10-4.27 (m, 2 H), 4.01 (dt, J = 5.6, 12.4 Hz, 1 H), 3.71-3.89 (m, 2 H), 3.44-3.58 (m, 2 H), 3.33-3.37 (m, 1 H), 3.26-3.30 (m, 1 H). | 479/481 | A21B01C01 Regiomers were separated by SUPER-CRITICAL FLUID CHOMATO-GRAPHY: AD-3S_5_5_40_3 ML_T35.M |
| 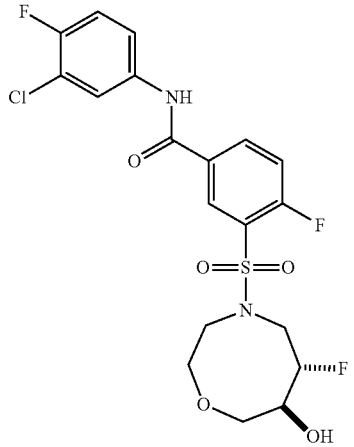 [SMILES: O=C(Nc1ccc(F)c(Cl)c1)c1ccc(F)c(S(=O)(=O)N2CCOC[C@H](O)[C@@H](F)C2)c1] | 2301_Trans1 | ¹H NMR (400 MHz, MeOD) δ 8.48 (dd, J = 2.3, 6.8 Hz, 1 H), 8.27 (ddd, J = 2.3, 4.7, 8.6 Hz, 1 H), 7.97 (dd, J = 2.5, 6.5 Hz, 1 H), 7.59-7.65 (m, 1 H), 7.49-7.57 (m, 1 H), 7.25 (t, J = 8.9 Hz, 1 H), 4.69 (d, J = 3.0 Hz, 1 H), 4.57 (d, J = 3.3 Hz, 1 H), 3.95-4.03 (m, 1 H), 3.81-3.93 (m, 2 H), 3.68-3.80 (m, 2 H), 3.55-3.67 (m, 2 H), 3.49 (d, J = 14.3 Hz, 1 H), 3.27 (brs, 1 H). | 479/481 | A22B01C01 Regiomers were separated by SUPER-CRITICAL FLUID CHOMATO-GRAPHY: AD-3S_5_5_40_3 ML_T35.M |
| 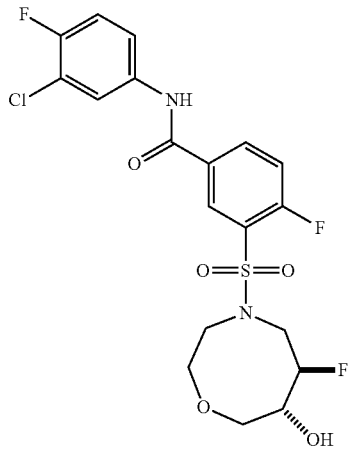 [SMILES: O=C(Nc1ccc(F)c(Cl)c1)c1ccc(F)c(S(=O)(=O)N2CCOC[C@@H](O)[C@H](F)C2)c1] | 2301_Trans2 | ¹H NMR (400 MHz, MeOD) δ 8.48 (dd, J = 2.3, 6.8 Hz, 1 H), 8.27 (m, 1 H), 7.97 (dd, J = 2.5, 6.5 Hz, 1 H), 7.58-7.67 (m, 1 H), 7.53 (dd, J = 8.9, 9.9 Hz, 1 H), 7.25 (t, J = 8.9 Hz, 1 H), 4.69 (dt, J = 2.9, 8.3 Hz, 1 H), 4.57 (d, J = 3.0 Hz, 1 H), 3.99 (m, 1 H), 3.81-3.93 (m, 2 H), 3.68-3.80 (m, 2 H), 3.55-3.67 (m, 2 H), 3.49 (d, J = 14.3 Hz, 1 H), 3.25-3.29 (m, 1 H). | 479/481 | A22B01C01 Regiomers were separated by SUPER-CRITICAL FLUID CHOMATO-GRAPHY: AD-3S_5_5_40_3 ML_T35.M |

TABLE 1-continued

| Structure | Compound ID | ¹H NMR | MS (M + H)⁺ | Synthetic method |
|---|---|---|---|---|
| 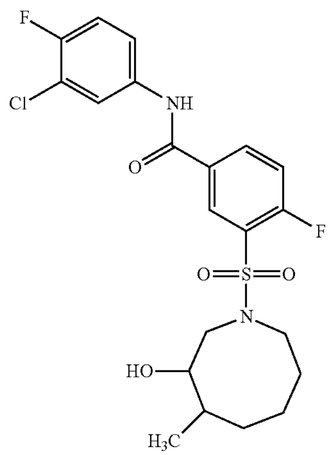 [SMILES: CC1CCCCN(S(=O)(=O)c2cc(C(=O)Nc3ccc(F)c(Cl)c3)ccc2F)CC1O] | 2309_D1 | | 473/475 | A10B01C01 |
| 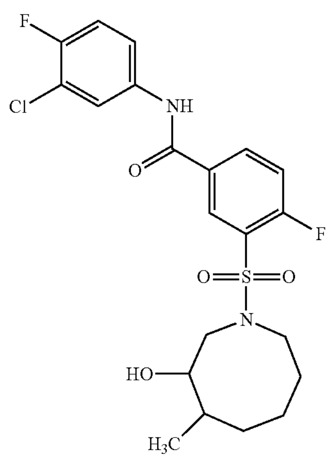 [SMILES: CC1CCCCN(S(=O)(=O)c2cc(C(=O)Nc3ccc(F)c(Cl)c3)ccc2F)CC1O] | 2309_D2 | | 473/475 | A10B01C01 |
| 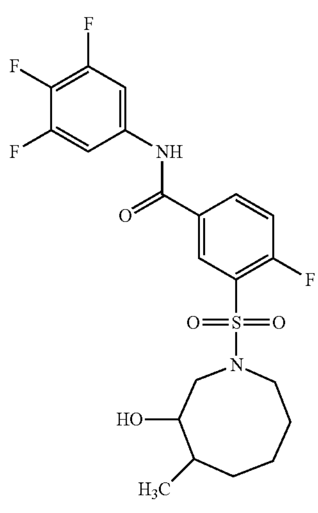 [SMILES: CC1CCCCN(S(=O)(=O)c2cc(C(=O)Nc3cc(F)c(F)c(F)c3)ccc2F)CC1O] | 2310_D1 | ¹H NMR (400 MHz, MeOD) δ 8.44-8.47 (m, 1 H), 8.24-8.26 (m, 1 H), 7.52-7.63 (m, 3 H), 4.01-4.03 (m, 1 H), 3.44-3.54 (m, 2 H), 3.09-3.15 (m, 2 H), 2.10-2.13 (m, 1 H), 1.69-1.79 (m, 5 H), 1.47-1.63 (m, 1 H), 1.04-1.06 (m, 3 H). | 475 | A10B01C02 |

TABLE 1-continued

| Structure | Compound ID | ¹H NMR | MS (M + H)⁺ | Synthetic method |
|---|---|---|---|---|
| 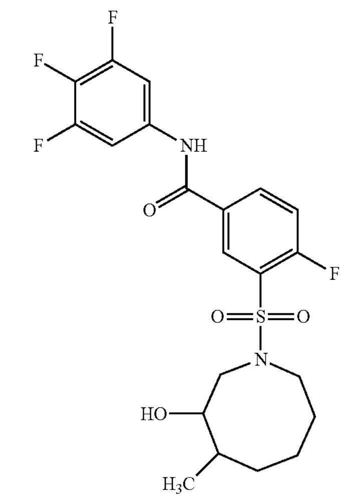 [SMILES: CC1CCCCN(S(=O)(=O)c2cc(C(=O)Nc3cc(F)c(F)c(F)c3)ccc2F)CC1O] | 2310_D2 | ¹H NMR (400 MHz, MeOD) δ 8.45-8.47 (m, 1 H), 8.23-8.26 (m, 1 H), 7.50-7.64 (m, 3 H), 3.48-3.63 (m, 3 H), 2.96-3.03 (m, 2 H), 1.56-2.06 (m, 7 H), 1.09-1.11 (m, 3 H). | 475 | A10B01C02 |
| 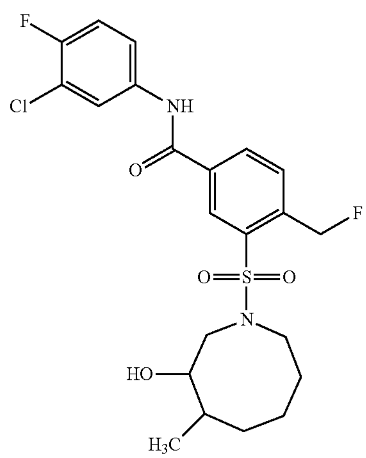 [SMILES: CC1CCCCN(S(=O)(=O)c2cc(C(=O)Nc3ccc(F)c(Cl)c3)ccc2CF)CC1O] | 2311_D1 | | 487/479 | A10B02C01 |
| 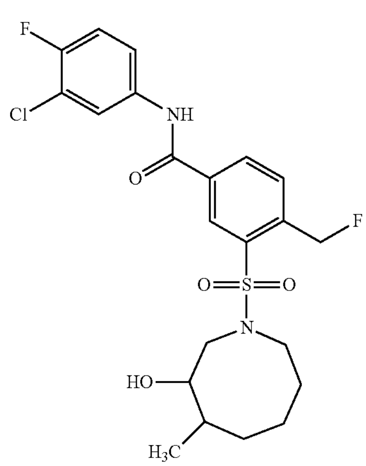 [SMILES: CC1CCCCN(S(=O)(=O)c2cc(C(=O)Nc3ccc(F)c(Cl)c3)ccc2CF)CC1O] | 2311_D2 | | 487/489 | A10B02C01 |

TABLE 1-continued

| Structure | Compound ID | ¹H NMR | MS (M + H)⁺ | Synthetic method |
|---|---|---|---|---|
| 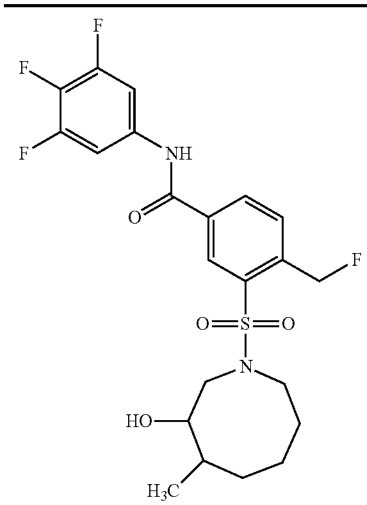 | 2312_D1 | ¹H NMR (400 MHz, MeOD) δ 8.32 (s, 1 H), 8.23-8.26 (m, 1 H), 7.92-7.94 (m, 1 H), 7.61-7.65 (m, 2 H), 5.95 (s, 1 H), 5.83 (s, 1 H), 3.96-4.00 (m, 1 H), 3.47-3.54 (m, 2 H), 3.15-3.21 (m, 2 H), 2.06-2.12 (m, 1 H), 1.69-1.81 (m, 5 H), 1.45-1.47 (m, 1 H), 1.03-1.05 (m, 3 H). | 489 | A10B02C02 |
| 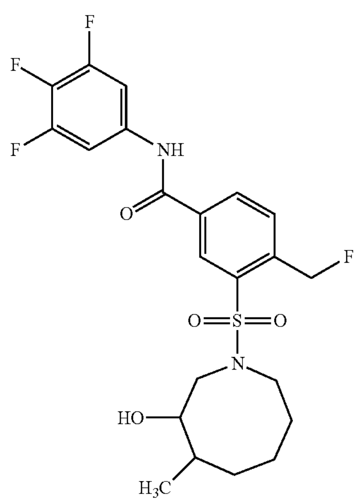 [SMILES: CC1CCCCN(S(=O)(=O)c2cc(C(=O)Nc3cc(F)c(F)c(F)c3)ccc2CF)CC1O] | 2312_D2 | ¹H NMR (400 MHz, MeOD) δ 8.32 (s, 1 H), 8.22-8.25 (m, 1 H), 7.92-7.94 (m, 1 H), 7.61-7.65 (m, 2 H), 5.96 (s, 1 H), 5.84 (s, 1 H), 3.48-3.60 (m, 3 H), 3.07-3.12 (m, 2 H), 1.59-1.92 (m, 7 H), 1.08-1.10 (m, 3 H). | 489 | A10B02C02 |
| 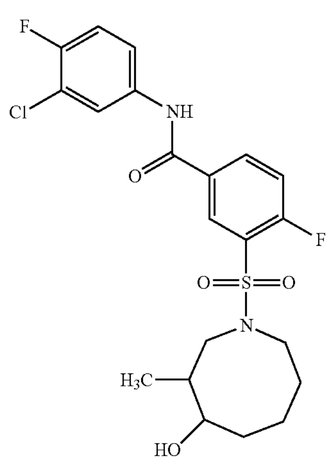 [SMILES: CC1CN(S(=O)(=O)c2cc(C(=O)Nc3ccc(F)c(Cl)c3)ccc2F)CCCCC1O] | 2313_D1 | ¹H NMR (400 MHz, MeOD) δ 8.43-8.46 (m, 1 H), 8.20-8.25 (m, 1 H), 7.80-7.97 (m, 1 H), 7.62-7.65 (m, 1 H), 7.49-7.53 (m, 1 H), 7.25-7.29 (m, 1 H), 3.25-3.40 (m, 3 H), 3.10-3.13 (m, 2 H), 2.04-2.14 (m, 3 H), 1.70-1.81 (m, 4 H), 1.01-1.03 (m, 3 H). | 473/475 | A11B01C01 |

TABLE 1-continued

| Structure | Compound ID | ¹H NMR | MS (M + H)⁺ | Synthetic method |
|---|---|---|---|---|
| 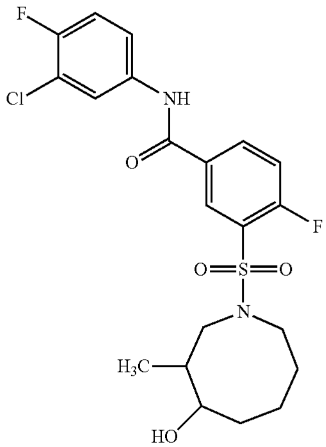 [SMILES: CC1CN(S(=O)(=O)c2cc(C(=O)Nc3ccc(F)c(Cl)c3)ccc2F)CCCCC1O] | 2313_D2 | ¹H NMR (400 MHz, MeOD) δ 8.44-8.47 (m, 1 H), 8.20-8.25 (m, 1 H), 7.80-7.97 (m, 1 H), 7.60-7.65 (m, 1 H), 7.48-7.53 (m, 1 H), 7.24-7.29 (m, 1 H), 3.94-3.97 (m, 1 H), 3.26-3.40 (m, 3 H), 3.08-3.11 (m, 1 H), 2.30-2.35 (m, 1 H), 1.60-2.06 (m, 6 H), 0.96-0.98 (m, 3 H). | 473/475 | A11B01C01 |
| 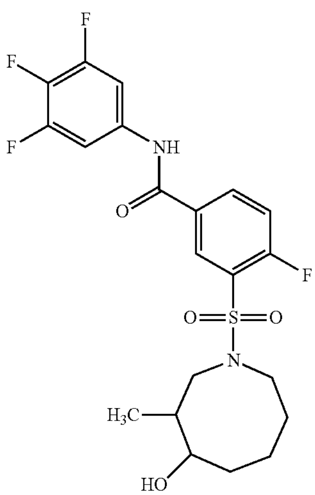 [SMILES: CC1CN(S(=O)(=O)c2cc(C(=O)Nc3cc(F)c(F)c(F)c3)ccc2F)CCCCC1O] | 2314_D1 | | 475 | A11B01C02 |
| 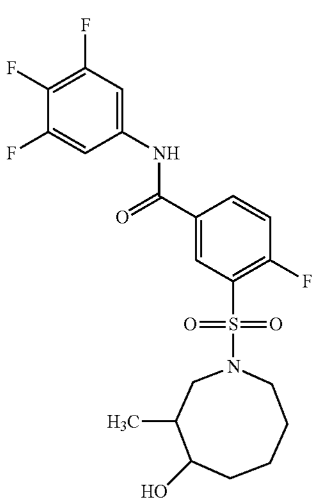 [SMILES: CC1CN(S(=O)(=O)c2cc(C(=O)Nc3cc(F)c(F)c(F)c3)ccc2F)CCCCC1O] | 2314_D2 | | 475 | A11B01C02 |

TABLE 1-continued

| Structure | Compound ID | ¹H NMR | MS (M + H)⁺ | Synthetic method |
|---|---|---|---|---|
| 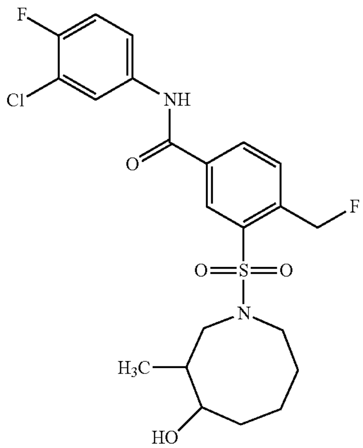 | 2315_D1 | | 487/489 | A11B02C01 |
| 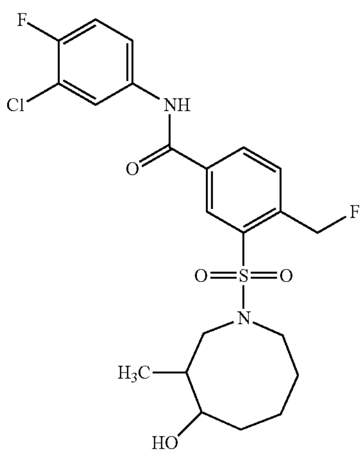 | 2315_D2 | | 487/489 | A11B02C01 |
| 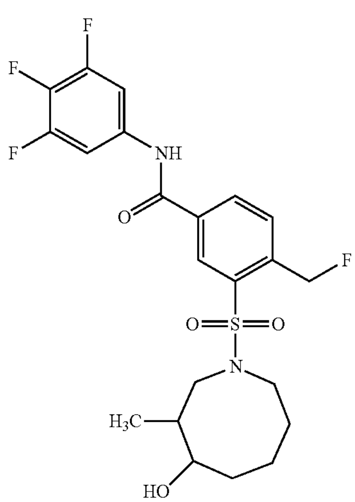 [SMILES: CC1CN(S(=O)(=O)c2cc(C(=O)Nc3cc(F)c(F)c(F)c3)ccc2CF)CCCCC1O] | 2316_D1 | | 489 | A11B02C02 |

TABLE 1-continued
| Structure | Compound ID | ¹H NMR | MS (M + H)⁺ | Synthetic method |
|---|---|---|---|---|
| 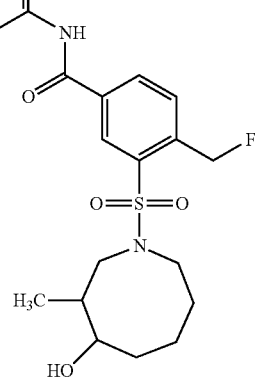 | 2316_D2 | ¹H NMR (400 MHz, MeOD) δ 8.29 (s, 1 H), 8.21-8.24 (m, 1 H), 7.91-7.93 (m, 1 H), 7.61-7.65 (m, 2 H), 5.94 (s, 1 H), 5.83 (s, 1 H), 3.95-3.97 (m, 1 H), 3.32-3.42 (m, 3 H), 3.10-3.14 (m, 1 H), 2.30-2.35 (m, 1 H), 1.60-1.94 (m, 6 H), 0.96-0.98 (m, 3 H). | 489 | A11B02C02 |
| 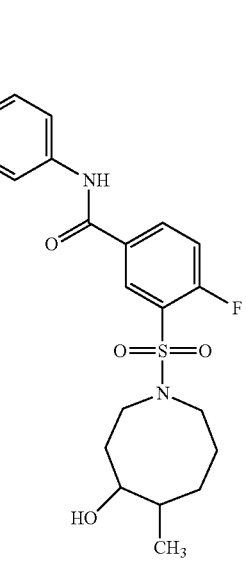 | 2317_D1 | | 473/475 | A07B01C01 |
| 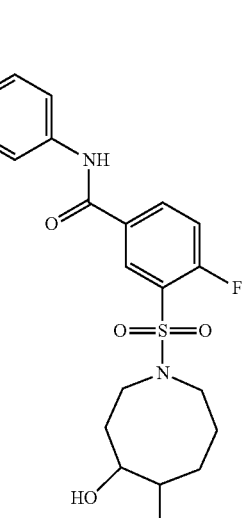 | 2317_D2 | | 473/475 | A07B01C01 |

TABLE 1-continued

| Structure | Compound ID | $^1$H NMR | MS (M + H)$^+$ | Synthetic method |
|---|---|---|---|---|
| 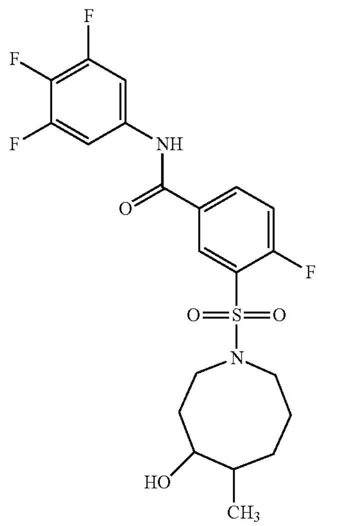 [SMILES: CC1CCCN(S(=O)(=O)c2cc(C(=O)Nc3cc(F)c(F)c(F)c3)ccc2F)CCC1O] | 2318_D1 | | 475 | A07B01C02 |
| 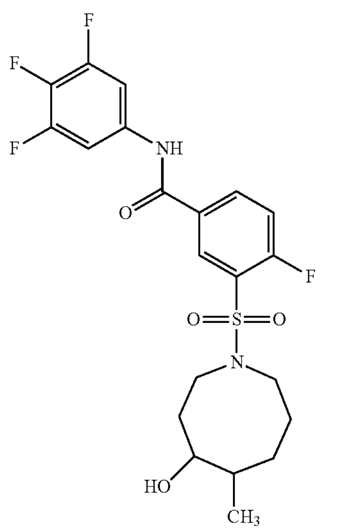 [SMILES: CC1CCCN(S(=O)(=O)c2cc(C(=O)Nc3cc(F)c(F)c(F)c3)ccc2F)CCC1O] | 2318_D2 | | 475 | A07B01C02 |
| 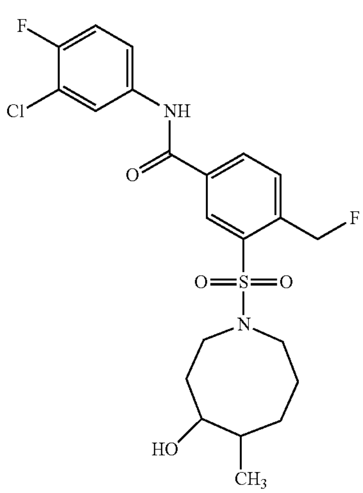 [SMILES: CC1CCCN(S(=O)(=O)c2cc(C(=O)Nc3ccc(F)c(Cl)c3)ccc2CF)CCC1O] | 2319_D1 | | 487/489 | A07B01C01 |

TABLE 1-continued

| Structure | Compound ID | ¹H NMR | MS (M + H)⁺ | Synthetic method |
|---|---|---|---|---|
| 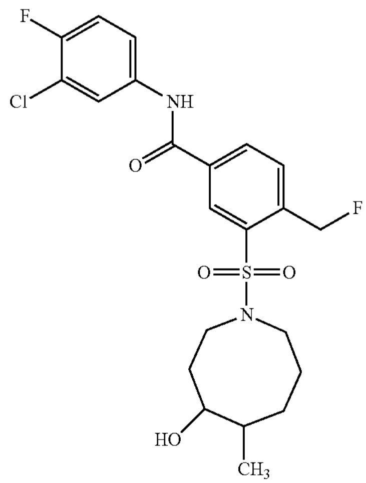 [SMILES: CC1CCCN(S(=O)(=O)c2cc(C(=O)Nc3ccc(F)c(Cl)c3)ccc2CF)CCC1O] | 2319_D2 |  | 487/489 | A07B02C01 |
| 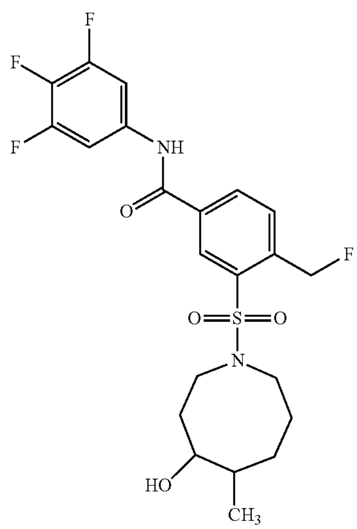 [SMILES: CC1CCCN(S(=O)(=O)c2cc(C(=O)Nc3cc(F)c(F)c(F)c3)ccc2CF)CCC1O] | 2320_D1 |  | 489 | A07B02C02 |
| 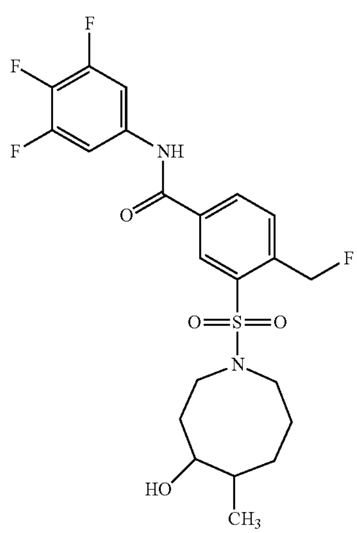 [SMILES: CC1CCCN(S(=O)(=O)c2cc(C(=O)Nc3cc(F)c(F)c(F)c3)ccc2CF)CCC1O] | 2320_D2 |  | 489 | A07B02C02 |

TABLE 1-continued

| Structure | Compound ID | ¹H NMR | MS (M + H)⁺ | Synthetic method |
|---|---|---|---|---|
| 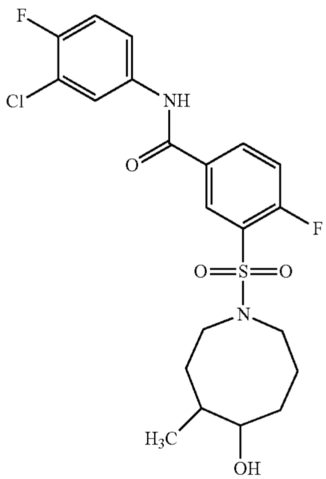 | 2321_D1 | ¹H NMR (400 MHz, MeOD) δ 8.44-8.46 (m, 1 H), 8.20-8.25 (m, 1 H), 7.97-7.99 (m, 1 H), 7.60-7.65 (m, 1 H), 7.48-7.52 (m, 1 H), 7.25-7.29 (m, 1 H), 3.72-3.78 (m, 2 H), 3.50-3.55 (m, 1 H), 3.00-3.05 (m, 1 H), 2.84-2.88 (m, 1 H), 1.63-2.02 (m, 7 H), 1.18-1.20 (m, 3 H). | 473/475 | A13B01C01 |
| 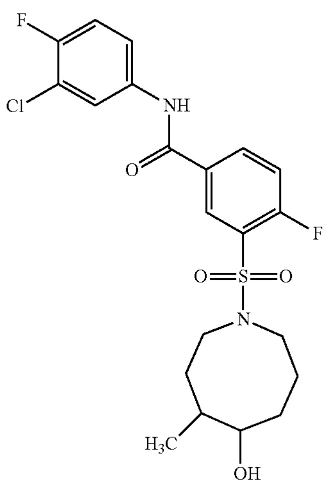 [SMILES: CC1CCN(S(=O)(=O)c2cc(C(=O)Nc3ccc(F)c(Cl)c3)ccc2F)CCCC1O] | 2321_D2 | ¹H NMR (400 MHz, MeOD) δ 8.44-8.46 (m, 1 H), 8.20-8.25 (m, 1 H), 7.97-7.99 (m, 1 H), 7.60-7.65 (m, 1 H), 7.48-7.52 (m, 1 H), 7.25-7.29 (m, 1 H), 3.90-3.92 (m, 1 H), 3.61-3.65 (m, 1 H), 3.48-3.50 (m, 1 H), 3.05-3.19 (m, 2 H), 1.52-2.08 (m, 7 H), 1.04-1.06 (m, 3 H). | 473/475 | A13B01C01 |
| 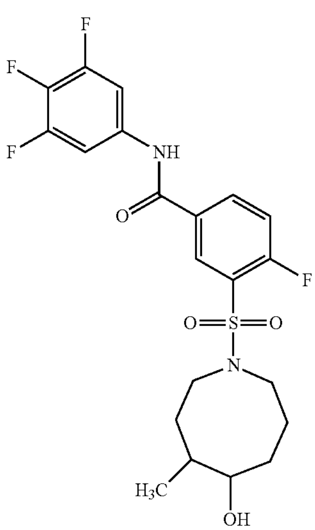 | 2322_D1 | | 475 | A13B01C02 |

TABLE 1-continued

| Structure | Compound ID | ¹H NMR | MS (M + H)⁺ | Synthetic method |
|---|---|---|---|---|
| 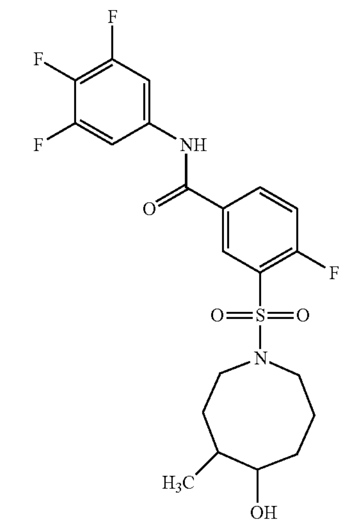 | 2322_D2 | | 475 | A13B01C02 |
| 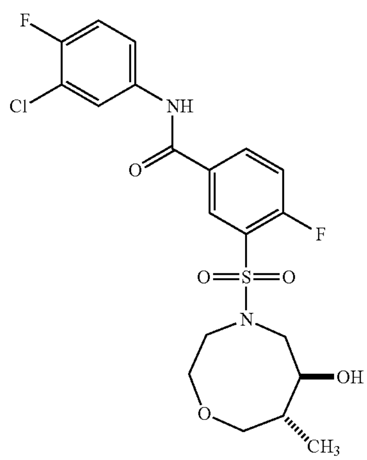 [SMILES: C[C@@H]1COCCN(S(=O)(=O)c2cc(C(=O)Nc3ccc(F)c(Cl)c3)ccc2F)C[C@H]1O] | 2325 | ¹H NMR (400 MHz, MeOD) δ 8.48 (dd, J = 2.3, 6.8 Hz, 1 H), 8.25 (m, 1 H), 7.96 (dd, J = 2.6, 6.7 Hz, 1 H), 7.58-7.66 (m, 1 H), 7.52 (dd, J = 9.0, 9.8 Hz, 1 H), 7.25 (t, J = 8.9 Hz, 1 H), 3.80-3.93 (m, 2 H), 3.67-3.76 (m, 1 H), 3.34-3.66 (m, 6 H), 1.87-2.00 (m, 1 H), 0.97 (d, J = 6.8 Hz, 3H). | 475/477 | A20B01C01 |
| 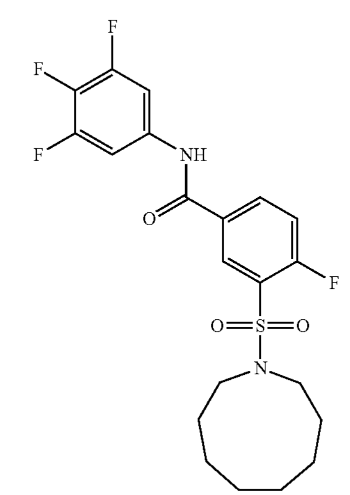 [SMILES: O=C(Nc1cc(F)c(F)c(F)c1)c1ccc(F)c(S(=O)(=O)N2CCCCCCCC2)c1] | 2435 | | 459 | A27B01C02 |

TABLE 1-continued

| Structure | Compound ID | ¹H NMR | MS (M + H)⁺ | Synthetic method |
|---|---|---|---|---|
| 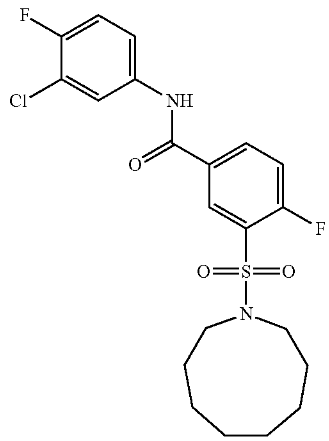 [SMILES: O=C(Nc1ccc(F)c(Cl)c1)c1ccc(F)c(S(=O)(=O)N2CCCCCCCC2)c1] | 2436 | | 457/459 | A27B01C01 |
| 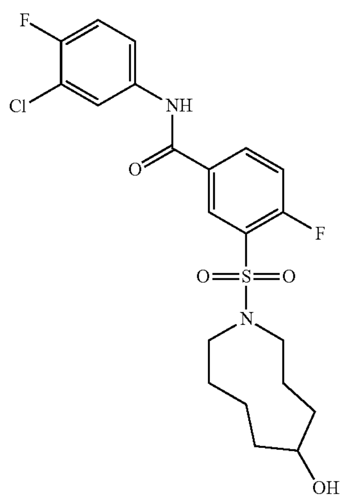 [SMILES: O=C(Nc1ccc(F)c(Cl)c1)c1ccc(F)c(S(=O)(=O)N2CCCCC(O)CCC2)c1] | 2448 | ¹H NMR (400 MHz, MeOD) δ 8.45-8.43 (dd, 1 H), 8.22-8.24 (m, 1 H), 7.95-7.97 (m, 1 H), 7.60-7.64 (m, 1 H), 7.47-7.52 (t, 1 H), 7.23-7.28 (t, 1 H), 4.02 (m, 1 H), 3.33-3.37 (m, 2 H), 3.13-3.17 (m, 2 H), 1.83-1.97 (m, 8 H), 1.67-1.70 (m, 2 H). | 473/475 | A28B01C01 |
| 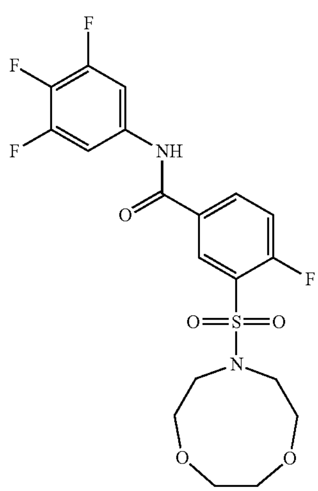 [SMILES: O=C(Nc1cc(F)c(F)c(F)c1)c1ccc(F)c(S(=O)(=O)N2CCOCCOCC2)c1] | 2483 | ¹H NMR (400 MHz, MeOD) δ 8.47 (dd, J = 6.52, 2.01 Hz, 1 H), 8.21-8.30 (m, 1 H), 7.47-7.67 (m, 3 H), 3.87-3.99 (m, 4 H), 3.76 (s, 4 H), 3.43-3.54 (m, 4 H). | 463 | A26B01C02 |

TABLE 1-continued
| Structure | Compound ID | ¹H NMR | MS (M + H)⁺ | Synthetic method |
|---|---|---|---|---|
| 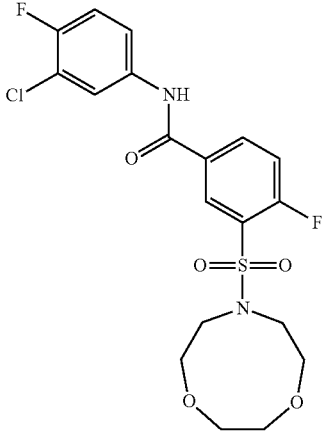 [SMILES: O=C(Nc1ccc(F)c(Cl)c1)c1ccc(F)c(S(=O)(=O)N2CCOCCOCC2)c1] | 2484 | | 461/463 | A26B01C01 |
| 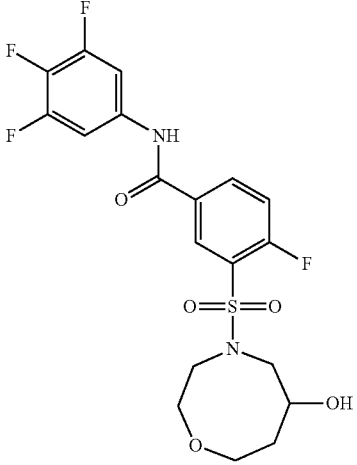 [SMILES: O=C(Nc1cc(F)c(F)c(F)c1)c1ccc(F)c(S(=O)(=O)N2CCOCCC(O)C2)c1] | 2518 | | 463/465 | A17B01C02 |
| 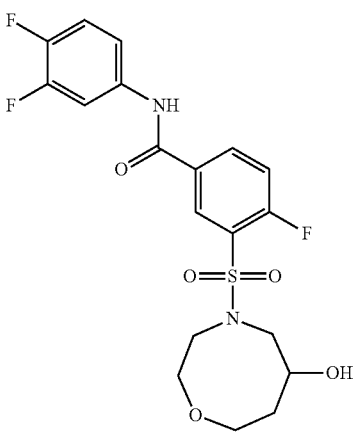 [SMILES: O=C(Nc1ccc(F)c(F)c1)c1ccc(F)c(S(=O)(=O)N2CCOCCC(O)C2)c1] | 2519 | | 445/447 | A17B01C03 |

TABLE 1-continued

| Structure | Compound ID | ¹H NMR | MS (M + H)⁺ | Synthetic method |
|---|---|---|---|---|
| 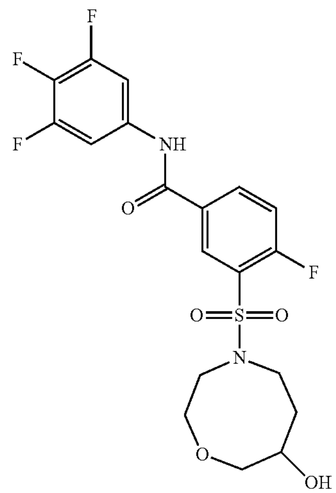 [SMILES: O=C(Nc1cc(F)c(F)c(F)c1)c1ccc(F)c(S(=O)(=O)N2CCOCC(O)CC2)c1] | 2520 | | 463/465 | A18B01C02 |
| 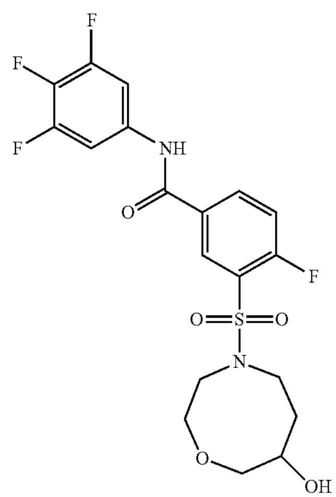 [SMILES: O=C(Nc1cc(F)c(F)c(F)c1)c1ccc(F)c(S(=O)(=O)N2CCOCC(O)CC2)c1] | 2520_E1 | | 463/465 | A18B01C02 Enantiomers were separated by SUPER- CRITICAL FLUID CHOMATO- GRAPHY |
| 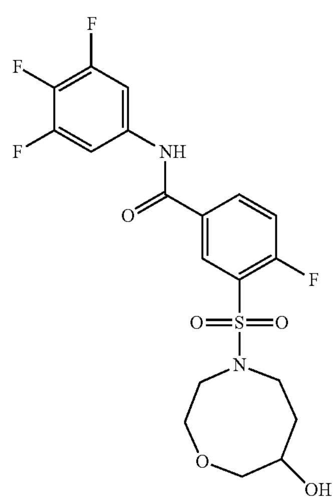 [SMILES: O=C(Nc1cc(F)c(F)c(F)c1)c1ccc(F)c(S(=O)(=O)N2CCOCC(O)CC2)c1] | 2520_E2 | | 463/465 | A18B01C02 Enantiomers were separated by SUPER- CRITICAL FLUID CHOMATO- GRAPHY |

TABLE 1-continued

| Structure | Compound ID | ¹H NMR | MS (M + H)⁺ | Synthetic method |
|---|---|---|---|---|
| 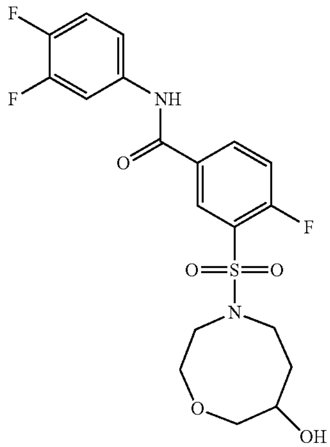 [SMILES: O=C(Nc1ccc(F)c(F)c1)c1ccc(F)c(S(=O)(=O)N2CCOCC(O)CC2)c1] | 2521 | | 445/447 | A18B01C03 |
| 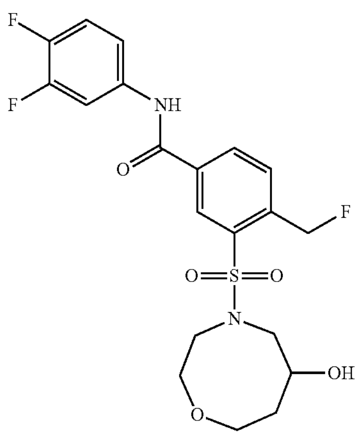 [SMILES: O=C(Nc1ccc(F)c(F)c1)c1ccc(CF)c(S(=O)(=O)N2CCOCCC(O)C2)c1] | 2527 | | 459 | A17B02C03 |
| 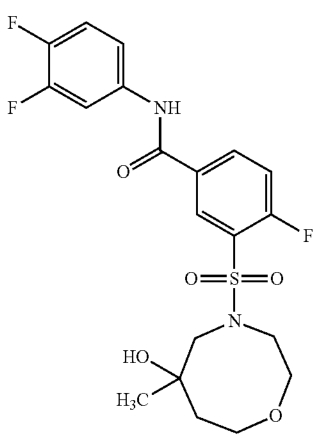 [SMILES: CC1(O)CCOCCN(S(=O)(=O)c2cc(C(=O)Nc3ccc(F)c(F)c3)ccc2F)C1] | 2533 | ¹H NMR (400 MHz, MeOD) δ 8.43-8.52 (m, 1 H), 8.22-8.32 (m, 1 H), 7.76-7.91 (m, 1 H), 7.39-7.56 (m, 2 H), 7.22-7.32 (m, 1 H), 3.67-3.87 (m, 4 H), 3.35-3.56 (m, 3 H), 3.12-3.24 (m, 1 H), 2.01-2.14 (m, 1 H), 1.68-1.79 (m, 1 H), 1.26 (s, 3 H). | 441 (M − 18)⁺ | A19B01C03 |

TABLE 1-continued
| Structure | Compound ID | $^1$H NMR | MS (M + H)$^+$ | Synthetic method |
|---|---|---|---|---|
| 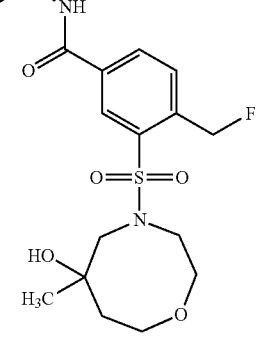 | 2534 | | 455/495 (M − 18)$^+$/ (M + 23)$^+$ | A19B02C02 |
| 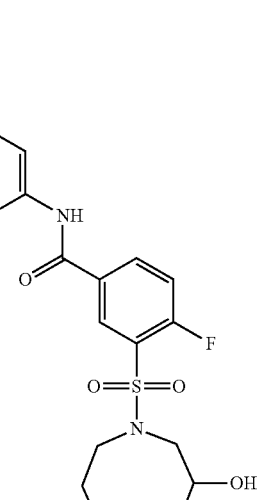 | 2584 | $^1$H NMR (400 MHz, MeOD) δ 8.46-8.48 (dd, 1 H), 8.22-8.26 (m, 1 H), 7.57-7.61 (dd, 2 H), 7.49-7.54 (dd., 1 H), 3.96-3.99 (m, 1 H), 3.87-3.91 (dd, 1 H), 3.69-3.84 (m, 4 H), 3.58-3.62 (dd, 1 H), 3.07-3.15 (m, 2 H), 2.05-2.14 (m, 1 H), 1.85-1.92 (m, 1 H). | 463 | A23B01C02 |
| 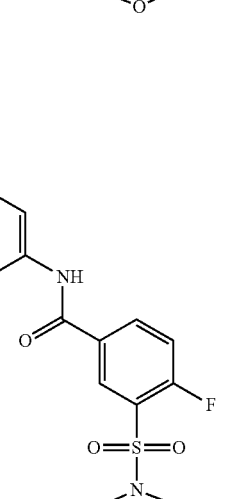 | 2580_Trans | $^1$H NMR (400 MHz, MeOD) δ 8.46-8.48 (dd, 1 H), 8.23-8.25 (m, 1 H), 7.51-7.61 (m, 3 H), 4.03 (m, 1 H), 3.86-3.87 (m, 2 H), 3.68-3.73 (m, 2 H), 3.54-3.57 (m, 3 H), 3.26-3.22 (m, 2 H). | 479 | A24B01C02 |

TABLE 1-continued

| Structure | Compound ID | ¹H NMR | MS (M + H)⁺ | Synthetic method |
|---|---|---|---|---|
| 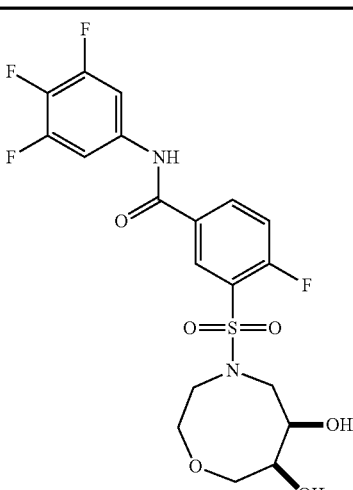 | 2580_Cis | ¹H NMR (400 MHz, MeOD) δ 8.45-8.47 (dd, 1 H), 8.23-8.27 (m, 1 H), 7.49-7.61 (m, 3H), 4.10= 4.18 (m, 2 H), 3.92-4.00 (m, 2 H), 3.59-3.71 (m, 4 H), 3.26-3.29 (m, 1 H), 3.06-3.12 (m, 1 H). | 479 | A25B01C02 |

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein.

Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

In one embodiment, the compounds of the invention may exist as tautomers. All tautomers are included within the scope of the compounds presented herein.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}$H, $^{3}$H, $^{11}$C, $^{13}$C, $^{14}$C, $^{36}$Cl, $^{18}$F, $^{123}$I, $^{125}$I, $^{13}$N, $^{15}$N, $^{15}$O, $^{17}$O, $^{18}$O, $^{32}$P, and $^{35}$S. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}$C, $^{18}$F, $^{15}$O and $^{13}$N, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4$^{th}$ Ed., (Wiley 1992); Carey and Sundberg, Advanced Organic Chemistry 4th Ed., Vols. A and B (Plenum 2000, 2001), and Green and Wuts, Protective Groups in Organic Synthesis 3rd Ed., (Wiley 1999) (all of which are incorporated herein in their entirety by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

Methods of the Invention

The invention provides a method of treating an HBV infection in an individual in need thereof, comprising administering to the individual a therapeutically effective amount of a compound of the invention.

The invention also provides a method of reducing the viral load associated with an HBV infection in an individual in need thereof, comprising administering to the individual a therapeutically effective amount of a compound of the invention.

The invention also provides a method of reducing reoccurrence of an HBV infection in an individual in need thereof, comprising administering to the individual a therapeutically effective amount of a compound of the invention.

The invention further provides a method of reducing an adverse physiological impact of an HBV infection in an individual in need thereof, comprising administering to the individual a therapeutically effective amount of a compound of the invention.

The invention further provides a method of inducing remission of hepatic injury from an HBV infection in an individual in need thereof, comprising administering to the individual a therapeutically effective amount of a compound of the invention.

The invention also provides a method of reducing the physiological impact of long-term antiviral therapy for HBV infection in an individual in need thereof, comprising administering to the individual a therapeutically effective amount of a compound of the invention.

The invention also provides a method of prophylactically treating an HBV infection in an individual in need thereof, wherein the individual is afflicted with a latent HBV infection, comprising administering to the individual a therapeutically effective amount of a compound of the invention.

In one embodiment, the methods described herein further comprise administering to the individual at least one additional therapeutic agent selected from the group consisting of a HBV polymerase inhibitor, immunomodulatory agents, pegylated interferon, viral entry inhibitor, viral maturation inhibitor, capsid assembly modulator, reverse transcriptase inhibitor, a cyclophilin/TNF inhibitor, a TLR-agonist, and an HBV vaccine, and a combination thereof. In another embodiment, the compound of the invention and the at least one additional therapeutic agent are co-formulated. In yet another embodiment, the compound of the invention and the at least one additional therapeutic agent are co-administered.

In one embodiment, the administering a compound of the invention allows for administering of the at least one additional therapeutic agent at a lower dose or frequency as compared to the administering of the at least one additional therapeutic agent alone that is required to achieve similar results in prophylactically treating an HBV infection in an individual in need thereof.

In one embodiment, the administering of a compound of the invention reduces the viral load in the individual to a greater extent or at a faster rate compared to the administering of a compound selected from the group consisting of a HBV polymerase inhibitor, interferon, viral entry inhibitor, viral maturation inhibitor, distinct capsid assembly modulator, antiviral compounds, and any combination thereof.

In one embodiment, the administering of a compound of the invention causes a lower incidence of viral mutation or viral resistance than the administering of a compound selected from the group consisting of a HBV polymerase inhibitor, an interferon, a viral entry inhibitor, a viral maturation inhibitor, a capsid assembly modulator, an antiviral compound, and combinations thereof.

The invention also provide a method of treating an HBV infection in an individual in need thereof, comprising reducing the HBV viral load by administering to the individual a therapeutically effective amount of a compound of the invention alone or in combination with a reverse transcriptase inhibitor; and further administering to the individual a therapeutically effective amount of HBV vaccine.

In one embodiment, the method of the invention further comprises monitoring the HBV viral load of the subject, and wherein the method is carried out for a period of time such that the HBV virus is undetectable.

Accordingly, in one embodiment, provided herein is a method of treating an HBV infection in an individual in need thereof, comprising administering to the individual a therapeutically effective amount of a compound of Formula I, or a pharmaceutically acceptable salt thereof.

In another embodiment, provided herein is a method of treating an HBV infection in an individual in need thereof, comprising administering to the individual a therapeutically effective amount of compound 2039, or a pharmaceutically acceptable salt thereof.

In another embodiment, provided herein is a method of treating an HBV infection in an individual in need thereof, comprising administering to the individual a therapeutically effective amount of compound 2039_E1, or a pharmaceutically acceptable salt thereof.

In another embodiment, provided herein is a method of treating an HBV infection in an individual in need thereof, comprising administering to the individual a therapeutically effective amount of compound 2039_E2, or a pharmaceutically acceptable salt thereof.

In another embodiment, provided herein is a method of treating an HBV infection in an individual in need thereof, comprising administering to the individual a therapeutically effective amount of compound 2040, or a pharmaceutically acceptable salt thereof.

In another embodiment, provided herein is a method of treating an HBV infection in an individual in need thereof, comprising administering to the individual a therapeutically effective amount of compound 2040_E1, or a pharmaceutically acceptable salt thereof.

In another embodiment, provided herein is a method of treating an HBV infection in an individual in need thereof, comprising administering to the individual a therapeutically effective amount of compound 2040_E2, or a pharmaceutically acceptable salt thereof.

In another embodiment, provided herein is a method of treating an HBV infection in an individual in need thereof, comprising administering to the individual a therapeutically effective amount of compound 2285_D1, or a pharmaceutically acceptable salt thereof.

In another embodiment, provided herein is a method of treating an HBV infection in an individual in need thereof, comprising administering to the individual a therapeutically effective amount of compound 2285 D2, or a pharmaceutically acceptable salt thereof.

In another embodiment, provided herein is a method of treating an HBV infection in an individual in need thereof, comprising administering to the individual a therapeutically effective amount of compound 2435, or a pharmaceutically acceptable salt thereof.

In another embodiment, provided herein is a method of treating an HBV infection in an individual in need thereof, comprising administering to the individual a therapeutically effective amount of compound 2436, or a pharmaceutically acceptable salt thereof.

In another embodiment, provided herein is a method of treating an HBV infection in an individual in need thereof, comprising administering to the individual a therapeutically effective amount of compound 2520, or a pharmaceutically acceptable salt thereof.

In another embodiment, provided herein is a method of treating an HBV infection in an individual in need thereof, comprising administering to the individual a therapeutically effective amount of compound 2520_E1, or a pharmaceutically acceptable salt thereof.

In another embodiment, provided herein is a method of treating an HBV infection in an individual in need thereof, comprising administering to the individual a therapeutically effective amount of compound 2520_E2, or a pharmaceutically acceptable salt thereof.

Combination Therapies

The compounds of the present invention are intended to be useful in combination with one or more additional compounds useful for treating HBV infection. These additional compounds may comprise compounds of the present invention or compounds known to treat, prevent, or reduce the symptoms or effects of HBV infection. Such compounds include but are not limited to HBV polymerase inhibitors, interferons, viral entry inhibitors, viral maturation inhibitors, literature-described capsid assembly modulators, reverse transcriptase inhibitor, a TLR-agonist, and other agents with distinct or unknown mechanisms that affect the HBV life cycle and/or affect the consequences of HBV infection.

In non-limiting examples, the compounds of the invention may be used in combination with one or more drugs (or a salt thereof) selected from the group consisting of:

HBV reverse transcriptase inhibitors, and DNA and RNA polymerase inhibitors, including but not limited to: lamivudine (3TC, Zeffix, Heptovir, Epivir, and Epivir-HBV), entecavir (Baraclude, Entavir), adefovir dipivoxil (Hepsara, Preveon, bis-POM PMEA), tenofovir disoproxil fumarate (Viread, TDF or PMPA);

interferons, including but not limited to interferon alpha (IFN-α), interferon lambda (IFN-λ), and interferon gamma (IFN-γ);

viral entry inhibitors;

viral maturation inhibitors;

literature-described capsid assembly modulators, such as, but not limited to BAY 41-4109;

reverse transcriptase inhibitor;

a TLR-agonist; and agents of distinct or unknown mechanism, such as but not limited to AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and similar analogs.

In one embodiment, the additional therapeutic agent is an interferon. The term "interferon" or "IFN" refers to any member the family of highly homologous species-specific proteins that inhibit viral replication and cellular proliferation, and modulate immune response. Human interferons are grouped into three classes; Type I, which include interferon-alpha (IFN-α), interferon-beta (IFN-β), and interferon-omega (IFN-ω), Type II, which includes interferon-gamma (IFN-γ), and Type III, which includes interferon-lambda (IFN-λ). Recombinant forms of interferons that have been developed and are commercially available are encompassed by the term "interferon" as used herein. Subtypes of interferons, such as chemically modified or mutated interferons, are also encompassed by the term "interferon" as used herein. Chemically modified interferons include pegylated interferons and glycosylated interferons. Examples of interferons include, but are not limited to, interferon-alpha-2a, interferon-alpha-2b, interferon-alpha-n1, interferon-beta-1a, interferon-beta-1b, interferon-lamda-1, interferon-lamda-2, and interferon-lamda-3. Examples of pegylated interferons include pegylated interferon-alpha-2a and pegylated interferon alpha-2b.

Accordingly, in one embodiment, the compounds of Formula I can be administered in combination with an interferon selected from the group consisting of interferon alpha (IFN-α), interferon beta (IFN-β), interferon lambda (IFN-λ), and interferon gamma (IFN-γ). In one specific embodiment, the interferon is interferon-alpha-2a, interferon-alpha-2b, or interferon-alpha-n1. In another specific embodiment, the interferon-alpha-2a or interferon-alpha-2b is pegylated. In a preferred embodiment, the interferon-alpha-2a is pegylated interferon-alpha-2a (PEGASYS).

In another embodiment, the additional therapeutic agent is a reverse transcriptase inhibitor, and is at least one of Zidovudine, Didanosine, Zalcitabine, 2',3'-dideoxyadenosine, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, and Etravirine.

In one embodiment, the additional therapeutic agent is a TLR modulator or a TLR agonist, such as a TLR-7 agonist or TLR-9 agonist. In a further embodiment of the combination therapy, the TLR agonist is selected from the group consisting of SM360320 (9-benzyl-8-hydroxy-2-(2-methoxy-ethoxy)adenine) and AZD 8848 (methyl [3-({[3-(6-amino-2-butoxy-8-oxo-7,8-dihydro-9H-purin-9-yl)propyl][3-(4-morpholinyl)propyl]amino}methyl)phenyl] acetate).

In any of the methods provided herein, the method may further comprise administering to the individual at least one HBV vaccine, a nucleoside HBV inhibitor, an interferon or any combination thereof. In an embodiment, the HBV vaccine is selected from the group consisting of RECOMBIVAX HB, ENGERIX-B, ELOVAC B, GENEVAC-B, and SHANVAC B.

In another aspect, provided herein is method of treating an HBV infection in an individual in need thereof, comprising reducing the HBV viral load by administering to the individual a therapeutically effective amount of a compound of the invention alone or in combination with a reverse transcriptase inhibitor; and further administering to the individual a therapeutically effective amount of HBV vaccine. The reverse transcriptase inhibitor may be one of Zidovudine, Didanosine, Zalcitabine, ddA, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, or Etravirine.

There can be three types of interactions between medications: additive, synergistic, and antagonistic. Additive interaction means the effect of two agents is equal to the sum of the effect of the two agents taken separately at the same doses. Synergistic interaction means that the effect of two agents taken together is greater than the sum of their separate effect at the same doses. Antagonistic interaction means that the effect of two agents is less than the sum of the effect of the two agents taken independently of each other at the same doses.

For any combination therapy described herein, synergistic effect may be calculated, for example, using suitable methods such as the Sigmoid-$E_{max}$ equation (Holford & Scheiner, 19981, Clin. Pharmacokinet. 6: 429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22: 27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

In another aspect, provided herein is pharmaceutical composition comprising a compound of the invention, or a pharmaceutically acceptable salt thereof, together with a pharmaceutically acceptable carrier.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level will depend upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is especially advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of HBV infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 g to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound (i.e., another drug for HBV treatment) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In one embodiment, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of HBV infection in a patient.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

For oral application, particularly suitable are tablets, dragées, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials:

Unless otherwise noted, all starting materials and resins were obtained from commercial suppliers and used without purification.

Library General Design

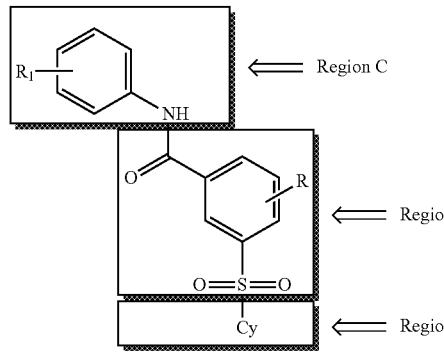

Region A:

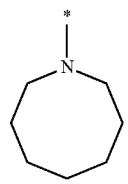

A01

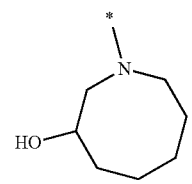

A02

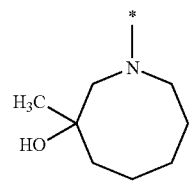

A03

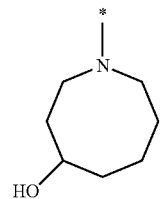

A04

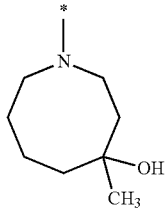

A05

| | |
|---|---|
| 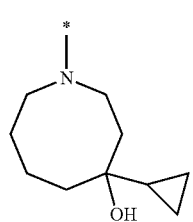 A06 | 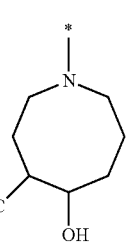 A13 |
| 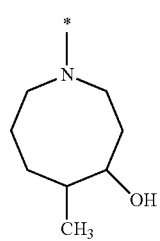 A07 | 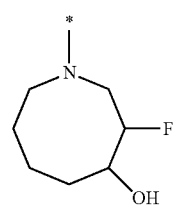 A14 |
| 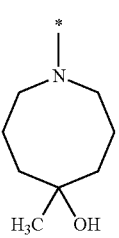 A08 | 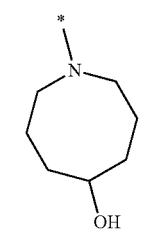 A15 |
| 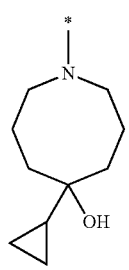 A09 | 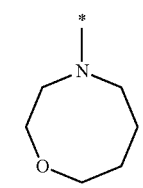 A16 |
| 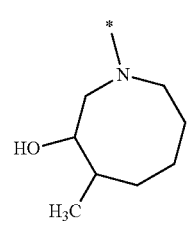 A10 | 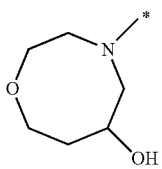 A17 |
| 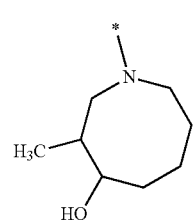 A11 | 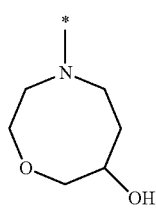 A18 |
| 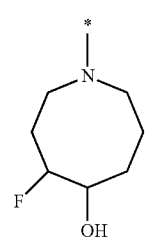 A12 | 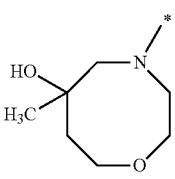 A19 |

-continued
A20 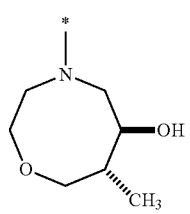
A21 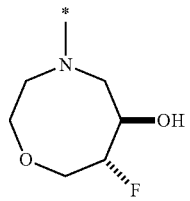
A22 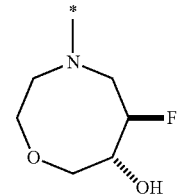
A23 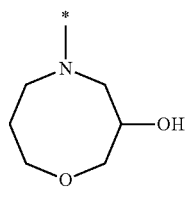
A24 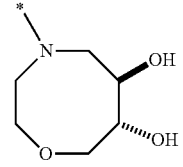
A25 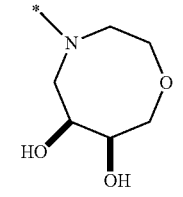
A26 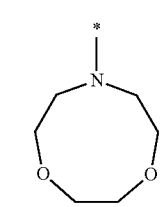
A27
-continued
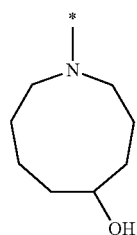 A28
Region B:
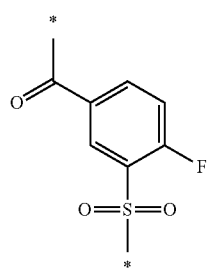 B01
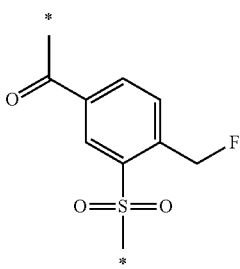 B02
Region C:
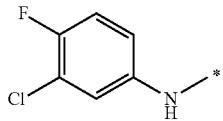 C01
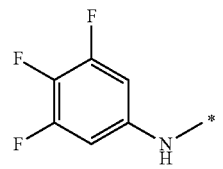 C02
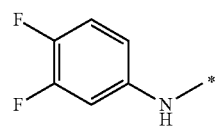 C03

Part I Intermediate Synthesis (Region A)

1.1 Preparation of Compound A02

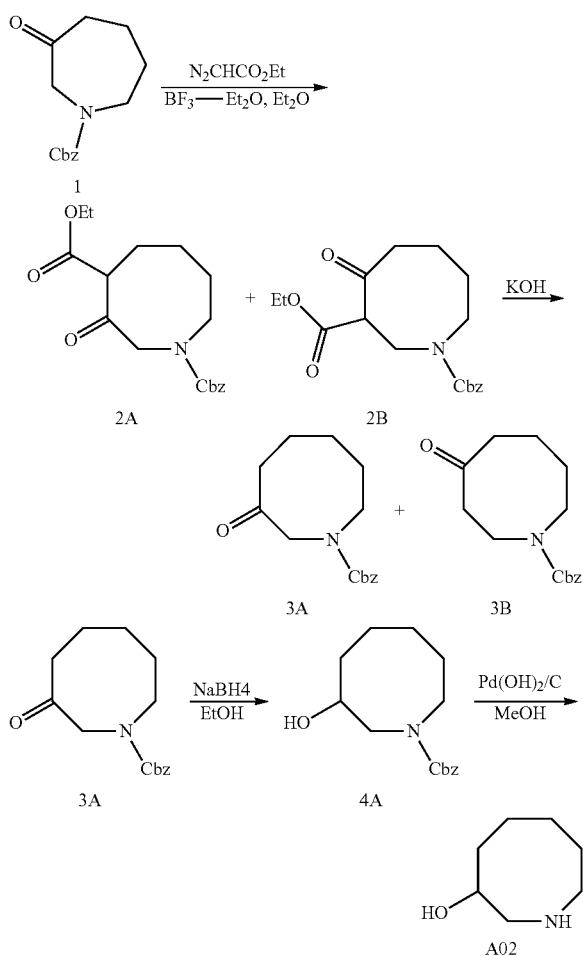

1.1.1 Preparation of Compound 2A/2B

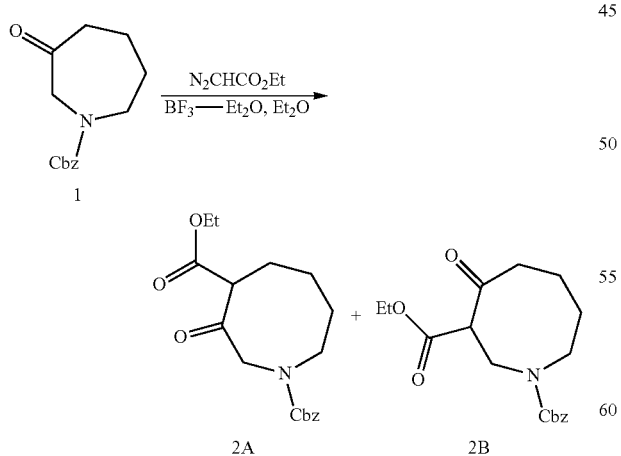

To a solution of compound 1 (14.0 g, 56.7 mmol) in THF (280 mL) was added $BF_3$-$Et_2O$ (24.8 mL, 198.4 mmol) and ethyl 2-diazoacetate (22.7 g, 199.1 mmol) at −78° C. under $N_2$. The reaction mixture was stirred at −78° C. for 1.5 h and then warmed to 25° C. stirred for 1.5 h. The resulting mixture was quenched with $NaHCO_3$ (Sat.) and extracted with EA (600 mL). The organic layer was dried over $Na_2SO_4$ and concentrated in vacuum to give the crude product, which was purified by flash column chromatography to give a mixture of compound 2A and 2B (19.0 g, crude). LCMS: 334.0 [M+1].

1.1.2 Preparation of Compound 3A/3B

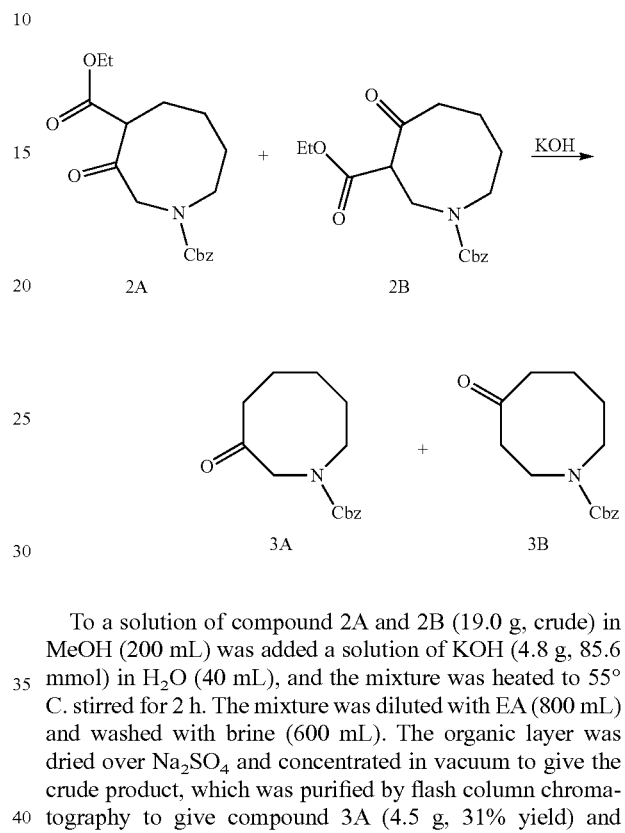

To a solution of compound 2A and 2B (19.0 g, crude) in MeOH (200 mL) was added a solution of KOH (4.8 g, 85.6 mmol) in $H_2O$ (40 mL), and the mixture was heated to 55° C. stirred for 2 h. The mixture was diluted with EA (800 mL) and washed with brine (600 mL). The organic layer was dried over $Na_2SO_4$ and concentrated in vacuum to give the crude product, which was purified by flash column chromatography to give compound 3A (4.5 g, 31% yield) and compound 3B (3.8 g, 26% yield). Compound 3A: $^1$H NMR (400 MHz, $CDCl_3$) δ 7.36-7.42 (m, 5 H), 5.21-5.24 (m, 2 H), 3.92-3.99 (m, 2 H), 3.54-3.57 (m, 2 H), 2.41-2.45 (m, 2 H), 1.58-1.73 (m, 6 H). Compound 3B: $^1$H NMR (400 MHz, $CDCl_3$) δ 7.28-7.41 (m, 5 H), 5.18 (s, 2 H), 3.68-3.75 (m, 2 H), 3.19-3.25 (m, 2 H), 2.62-2.68 (m, 2 H), 2.40-2.44 (m, 2 H), 1.62-1.92 (m, 4 H).

1.1.3 Preparation of Compound 4A

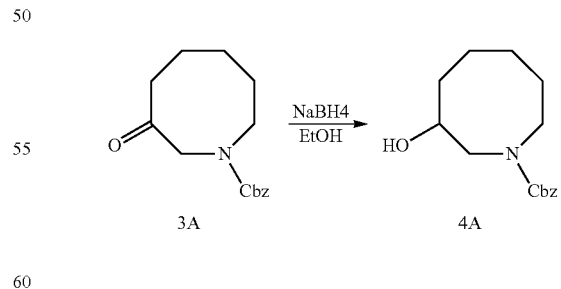

To a solution of compound 3A (1.0 g, 3.8 mmol) in EtOH (15 mL) was added $NaBH_4$ (0.22 g, 5.8 mmol) at 0° C., and the mixture was stirred at 18° C. for 1 h. The resulting mixture was quenched with $NH_4Cl$ and extracted with EA (100 mL). The organic layer was dried over $Na_2SO_4$ and concentrated in vacuum to give compound 4A (0.95 g, crude), which was used in the next step directly.

1.1.4 Preparation of Compound A02

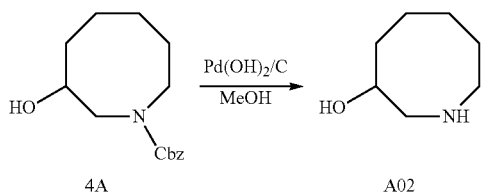 [SMILES: "MeOH" ; O=C(OCc1ccccc1)N1CCCCCC(O)C1 ; OC1CCCCCNC1 ; "A02"]

To a solution of compound 4A (0.95 g, 3.6 mmol) in MeOH (60 mL) was added Pd(OH)$_2$/C (200 mg). The suspension was degassed under vacuum and purged with H$_2$ several times. The mixture was stirred under H$_2$ (15 Psi) at 25° C. for 16 hr. The catalyst was filtered and the filtrate was concentrated in vacuum to give the crude product, which was used in the next step directly (0.45 g, 97%).

1.2 Preparation of Compound A03

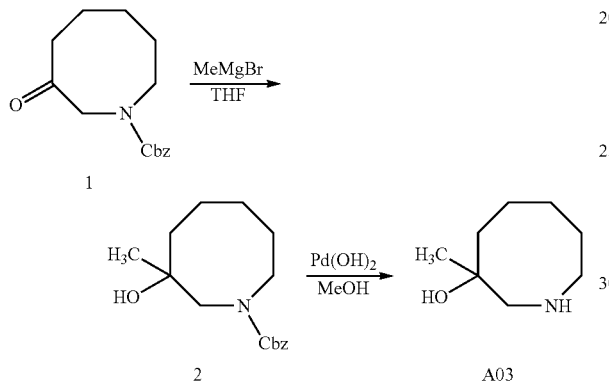

1.2.1 Preparation of Compound 2

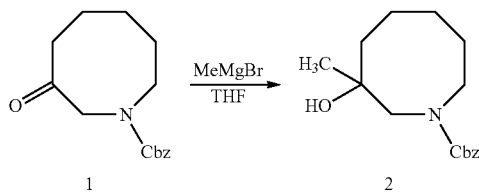 [SMILES: "MeMgBr" ; O=C1CCCCCN(C(=O)OCc2ccccc2)C1 ; CC1(O)CCCCCN(C(=O)OCc2ccccc2)C1 ; "THF"]

To a solution of CH$_3$M r (5.8 mL, 11.6 mmol) in THF (3 mL) was added a solution of compound 1 (1.0 g, 3.8 mmol) in THF (7 mL) at 0° C. under N$_2$. The reaction mixture was stirred at 20° C. for 2 h. The resulting mixture was quenched with NH$_4$Cl (sat.) and extracted with EtOAc (100 mL). The organic layer was dried and concentrated in vacuum to give the crude product, which was purified by flash column chromatography to give the desired product (0.52 g, 49%).

1.2.2 Preparation of Compound A03

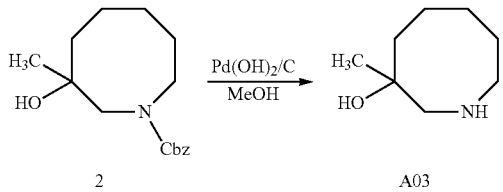

To a solution of compound 2 (0.52 g, 1.9 mmol) in MeOH (30 mL) was added Pd(OH)$_2$ (100 mg). The suspension was degassed under vacuum and purged with H$_2$ several times. The mixture was stirred under H$_2$ (15 Psi) at 25° C. for 16 hr. The catalyst was filtered and the filtrate was concentrated in vacuum to give the crude product, which was used in the next step directly (0.26 g, 97%).

1.3 Preparation of Compound A04

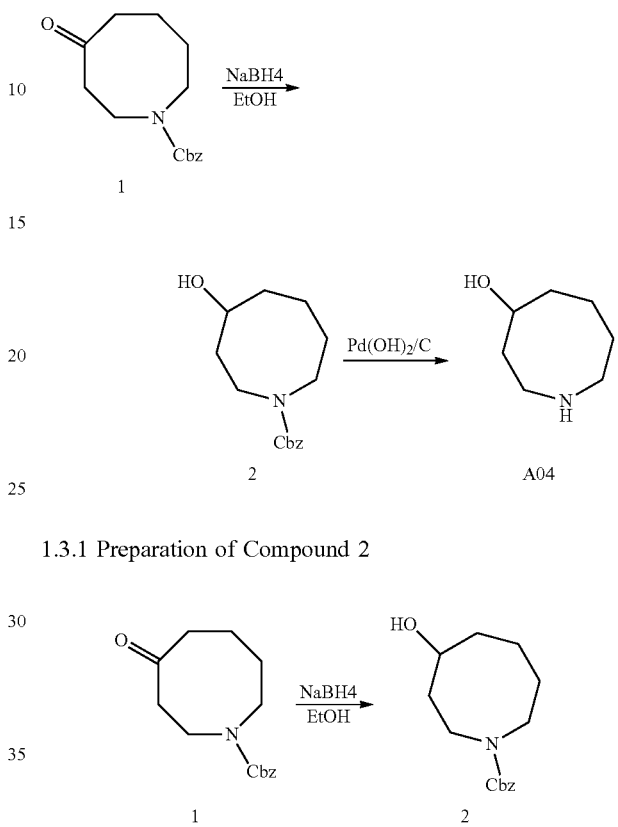

1.3.1 Preparation of Compound 2

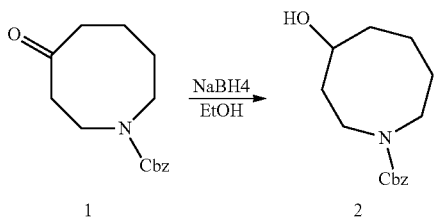 [SMILES: "EtOH" ; O=C1CCCCN(C(=O)OCc2ccccc2)CC1 ; "NaBH4" ; O=C(OCc1ccccc1)N1CCCCC(O)CC1]

To a solution of compound 1 (0.80 g, 3.1 mmol) in EtOH (15 mL) was added NaBH$_4$ (0.17 g, 4.5 mmol) at 0° C., and the mixture was stirred at 25° C. for 1 h. The resulting mixture was quenched with saturated NH$_4$Cl and extracted with EA (100 mL). The organic layer was dried over Na$_2$SO$_4$ and concentrated in vacuo to give compound 2 (0.76 g, crude), which was used in the next step directly.

1.3.2 Preparation of Compound A04

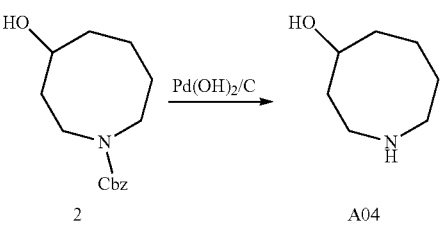 [SMILES: O=C(OCc1ccccc1)N1CCCCC(O)CC1 ; "Pd(OH)2/C" ; OC1CCCCNCC1 ; "A04"]

To a solution of compound 2 (0.76 g, 2.9 mmol) in MeOH (40 mL) was added Pd(OH)$_2$/C (150 mg). The suspension was degassed under vacuum and purged with H$_2$ several times. The mixture was stirred under H$_2$ (15 Psi) at 25° C. for 16 hr. The catalyst was filtered and the filtrate was concentrated in vacuum to give the crude product, which was used in the next step directly (0.37 g, 99%).

1.4 Preparation of Compound A05

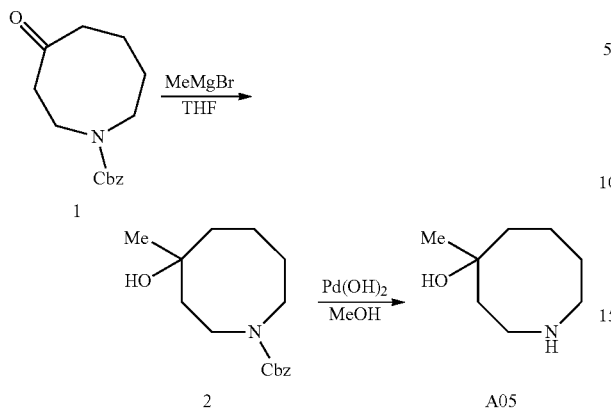

1.4.1 Preparation of Compound 2

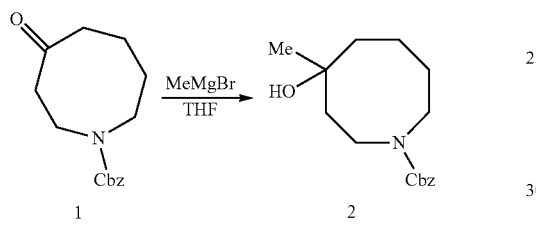

To a mixture of MeM r (3 M, 3.83 mL, 3.00 eq) in THF (30 mL) was added benzyl 4-oxoazocane-1-carboxylate (1.00 g, 3.83 mmol, 1.00 eq) in THF (30 mL) at 0° C. under $N_2$. The mixture was stirred at 0° C. for 10 min, then warmed to 15° C. and stirred for 2 hours. TLC showed the reaction was completed, the mixture was poured into saturated $NH_4Cl$ (50 mL) and stirred for 20 min. The aqueous phase was extracted with EA (40 mL*2). The combined organic phase was washed with saturated brine (20 mL), dried with anhydrous $Na_2SO_4$, filtered and concentrated in vacuum, the residue was purified by silica gel chromatography (PE/EA=10/1) to afford benzyl 4-hydroxy-4-methyl-azocane-1-carboxylate (950.00 mg, 3.43 mmol, 89.43% yield) as yellow oil.

1.4.2 Preparation of Compound A05

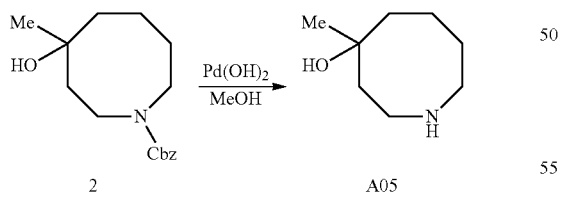

To a solution of benzyl 4-hydroxy-4-methyl-azocane-1-carboxylate (950.00 mg, 3.43 mmol, 1.00 eq) in MeOH (30 mL) was added $Pd(OH)_2$ (200.00 mg, 1.44 mmol, 0.42 eq) under $N_2$. The suspension was degassed under vacuum and purged with $H_2$ several times. The mixture was stirred under $H_2$ balloon at 15° C. for 6 hours. TLC showed the starting material was consumed completely. The reaction mixture was filtered and the filtrate was concentrated to give 4-methylazocan-4-ol (400.00 mg, 2.79 mmol, 81.42% yield) as yellow oil.

1.5 Preparation of Compound A06

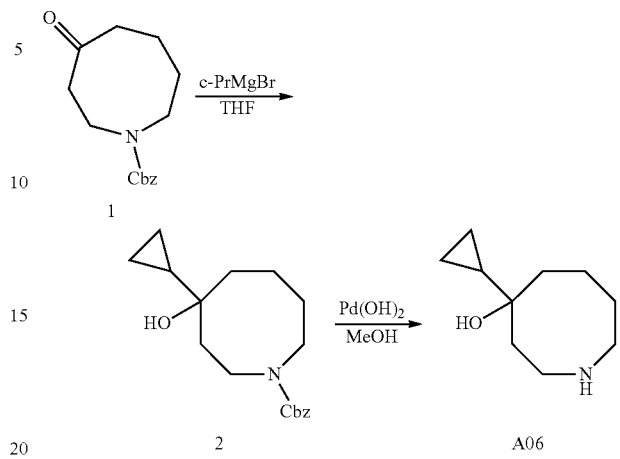

1.5.1 Preparation of Compound 2

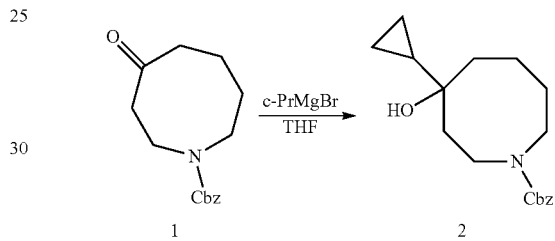

To a mixture of bromo(cyclopropyl)magnesium (0.5 M, 3.21 mL, 7.00 eq) in THF (30 mL) was added benzyl 4-oxoazocane-1-carboxylate (800.00 mg, 3.06 mmol, 1.00 eq) in THF (30 mL) at 0° C. under $N_2$. The mixture was stirred at 0° C. for 10 min, then warmed to 15° C. and stirred for 15 hours. LCMS showed the reaction was completed. The mixture was poured into saturated $NH_4Cl$ (50 mL) and stirred for 20 min, the aqueous phase was extracted with EA (40 mL*2), the combined organic phase was washed with saturated brine (20 mL), dried over anhydrous $Na_2SO_4$, filtered and concentrated in vacuum. The residue was purified by silica gel chromatography (PE/EA=10/1) to afford benzyl 4-cyclopropyl-4-hydroxy-azocane-1-carboxylate (650.00 mg, 2.14 mmol, 70.01% yield) as yellow oil. LCMS: 304.0 [M+1].

1.5.2 Preparation of Compound A06

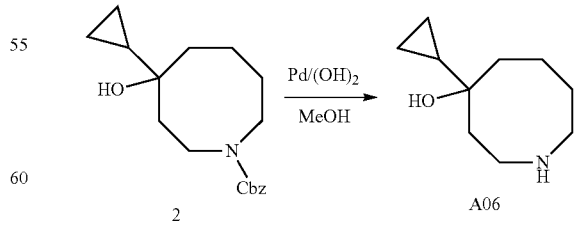

To a solution of benzyl 4-cyclopropyl-4-hydroxy-azocane-1-carboxylate (650.00 mg, 2.14 mmol, 1.00 eq) in MeOH (30 mL) was added Pd(OH)2 (100.00 mg, 722.44 umol, 0.34 eq) under $N_2$. The suspension was degassed under vacuum and purged with $H_2$ several times. The mixture was stirred under $H_2$ balloon at 15° C. for 6 hours. TLC showed the starting material was consumed completely. The reaction mixture was filtered and the filtrate was concentrated to give 4-cyclopropylazocan-4-ol (350.00 mg, 2.07 mmol, 96.63% yield) as yellow oil.

1.6 Preparation of Compound A07

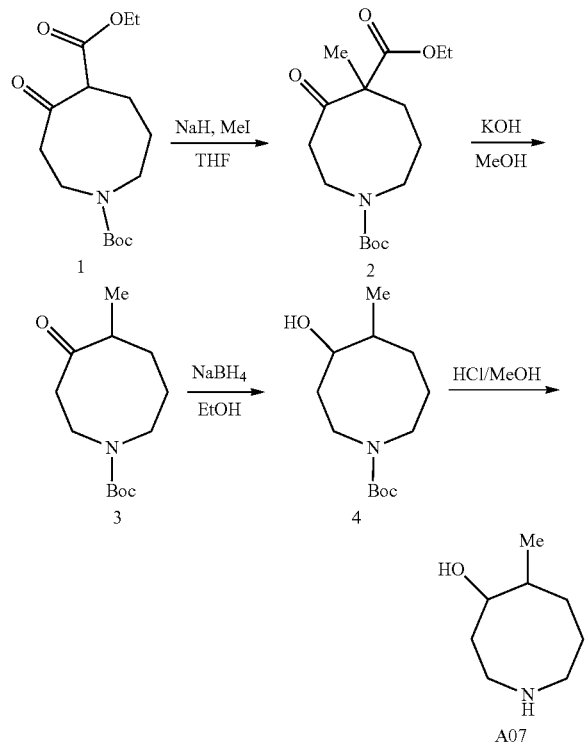

1.6.1 Preparation of Compound 2

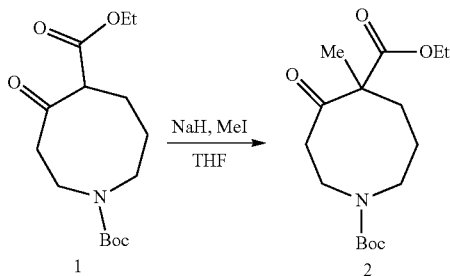 [SMILES: CCOC(=O)C1CCCN(C(=O)OC(C)(C)C)CCC1=O ; CCOC(=O)C1(C)CCCN(C(=O)OC(C)(C)C)CCC1=O ; "THF"]

To a mixture of NaH (240.48 mg, 10.02 mmol, 1.50 eq) in THF (30 mL), was added 1-tert-butyl 5-ethyl 4-oxoazocane-1,5-dicarboxylate (2.00 g, 6.68 mmol, 1.00 eq) in at 0° C. under $N_2$. The mixture was stirred at 0° C. for 0.5 h, then MeI (2.84 g, 20.04 mmol, 3.00 eq) was added to the mixture at 0° C., and the mixture was stirred at 18° C. for 6 hours. TLC showed the reaction was completed. The mixture was poured into saturated $NH_4Cl$ (150 mL) and stirred for 20 min. The aqueous phase was extracted with EA (40 mL*2). The combined organic phase was washed with saturated brine (20 mL*2), dried over anhydrous $Na_2SO_4$, filtered and concentrated in vacuum. The residue was purified by silica gel chromatography (PE/EA=10/1) to afford 1-tert-butyl 5-ethyl 5-methyl-4-oxo-azocane-1,5-dicarboxylate (2.00 g, 6.38 mmol, 95.54% yield) as yellow oil.

1.6.2 Preparation of Compound 3

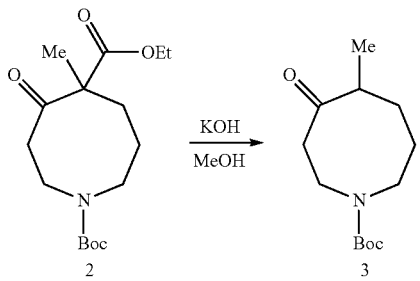

To a mixture of 1-tert-butyl 5-ethyl 5-methyl-4-oxo-azocane-1,5-dicarboxylate (2.28 g, 7.28 mmol, 1.00 eq) in MeOH (50 mL) and $H_2O$ (10 mL), was added KOH (816.96 mg, 14.56 mmol, 2.00 eq) in one portion at 18° C. under $N_2$. The mixture was heated to 60° C. for 3 hours. TLC showed the reaction was completed. The mixture was cooled to 18° C. and concentrated in reduced pressure. The aqueous phase was extracted with EA (40 mL*2). The combined organic phase was washed with saturated brine (20 mL*2), dried over anhydrous $Na_2SO_4$, filtered and concentrated in vacuum. The residue was purified by silica gel chromatography (PE/EA=10/1) to afford tert-butyl 5-methyl-4-oxo-azocane-1-carboxylate (1.53 g, 6.34 mmol, 87.09% yield) as yellow oil.

1.6.3 Preparation of Compound 4

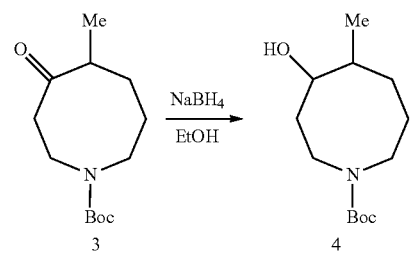

To a mixture of tert-butyl 5-methyl-4-oxo-azocane-1-carboxylate (1.53 g, 6.34 mmol, 1.00 Eq) in EtOH (50 mL), was added $NaBH_4$ (287.81 mg, 7.61 mmol, 1.20 Eq) in one portion at 18° C. under $N_2$. The mixture was stirred at 18° C. for 2 hr. TLC showed the reaction was completed. The mixture was poured into water (100 mL). The aqueous phase was extracted with EA (50 mL*3). The combined organic phase was washed with saturated brine (20 mL*2), dried over anhydrous $Na_2SO_4$, filtered and concentrated in vacuum. The residue was purified by silica gel chromatography (PE/EA=10/1, 5/1) to afford tert-butyl 4-hydroxy-5-methyl-azocane-1-carboxylate (1.34 g, 5.51 mmol, 86.86% yield) as yellow oil.

1.6.4 Preparation of Compound A07

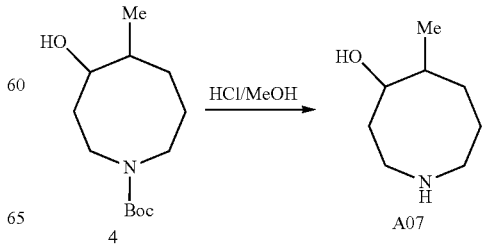

To a mixture of tert-butyl 4-hydroxy-5-methyl-azocane-1-carboxylate (300.00 mg, 1.23 mmol, 1.00 Eq) in MeOH (10 mL), was added HCl/MeOH (10 mL, 4M). The mixture was stirred at 18° C. for 2 hr. TLC showed the reaction was completed. The mixture was concentrated to afford 5-methylazocan-4-ol (200.00 mg, 1.11 mmol, 90.49% yield) as yellow oil.

1.7 Preparation of Compound A08

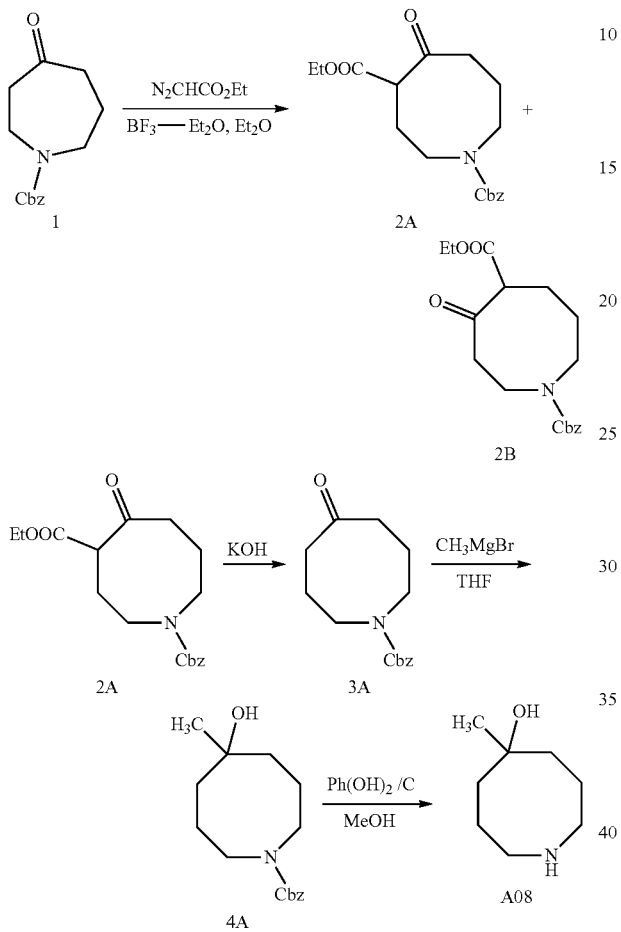

1.7.1 Preparation of Compound 2A/2B

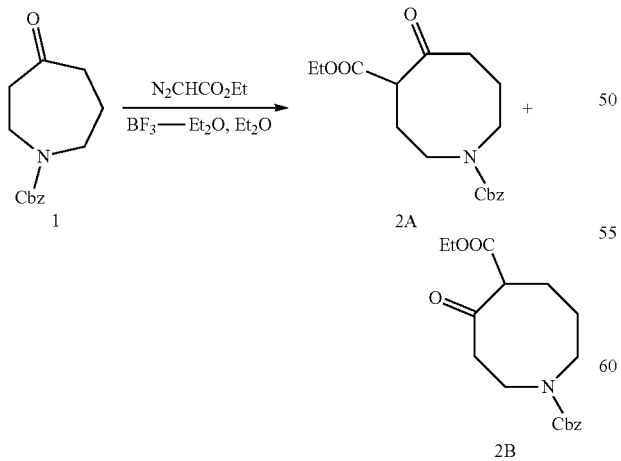

To a solution of compound 1 (9.3 g, 37.7 mmol) in Et₂O (200 mL) was added ethyl 2-diazoacetate (6.0 g, 52.7 mmol) and BF₃-Et₂O (5.4 mL, 43.3 mmol) at −78° C. under N₂. The reaction mixture was stirred at −78° C. for 1.5 h and then warmed to 25° C. for 16 h. The resulting mixture was quenched with NaHCO₃ (Sat.) and extracted with EA (300 mL). The organic layer was dried over Na₂SO₄ and concentrated in vacuum to give the crude product, which was purified by flash column chromatography to give compound 2A (4.3 g, 35%) and compound 2B (2.6 g, 21%).

1.7.2 Preparation of Compound 3A

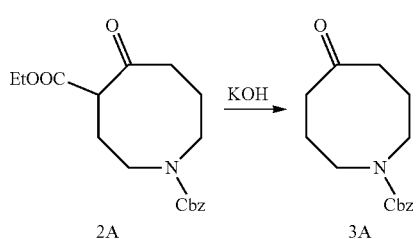

To a solution of compound 2A (4.3 g, crude) in MeOH (40 mL) was added a solution of KOH (1.1 g, 19.6 mmol) in H₂O (8 mL), the mixture was heated to 55° C. and stirred for 2 h. The mixture was diluted with EA (200 mL) and washed with brine (120 mL). The organic layer was dried over Na₂SO₄ and concentrated in vacuum to give the crude product, which was purified by flash column chromatography to give compound 3A (1.5 g, 45%). $^1$H NMR (400 MHz, CDCl₃) δ 7.33-7.44 (m, 5 H), 5.12 (s, 2 H), 3.34-3.46 (m, 4 H), 2.41-2.44 (m, 4 H), 2.11-2.18 (m, 4 H).

1.7.3 Preparation of Compound 4A

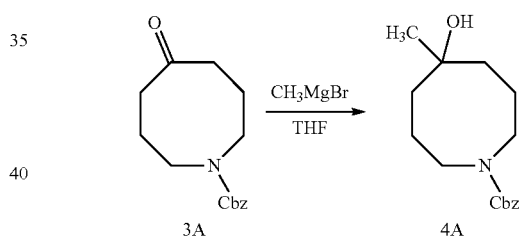

To a solution of CH₃M r (5.8 mL, 11.6 mmol) in THF (3 mL) was added a solution of compound 3B (1.0 g, 3.8 mmol) in THF (7 mL) at 0° C. under N₂. The reaction mixture was stirred at 20° C. for 2 h. The resulting mixture was quenched with NH₄Cl (sat.) and extracted with EtOAc (100 mL). The organic layer was dried and concentrated in vacuum to give the crude product, which was purified by flash column chromatography to give the desired product (0.55 g, 51%). $^1$H NMR (400 MHz, CDCl₃) δ 7.33-7.39 (m, 5 H), 5.16 (s, 2 H), 3.33-3.51 (m, 4 H), 1.58-2.07 (m, 8 H), 1.23 (s, 3 H).

1.7.4 Preparation of Compound A08

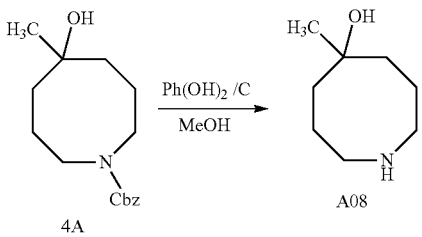

To a solution of compound 4B (0.55 g, 2.0 mmol) in MeOH (30 mL) was added Pd(OH)₂/C (100 mg). The suspension was degassed under vacuum and purged with H₂ several times. The mixture was stirred under H₂ balloon at 25° C. for 16 hours. The catalyst was filtered and the filtrate was concentrated in vacuum to give the crude product, which was used in the next step directly (0.26 g, 92%).

1.8 Preparation of Compound A09

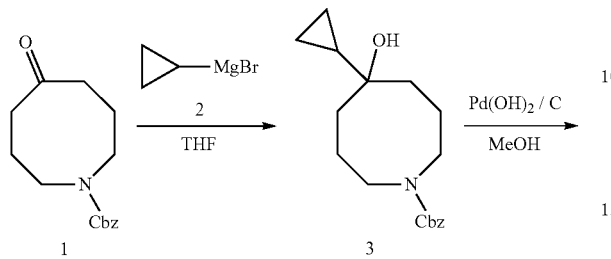

1.8.1 Preparation of Compound 3

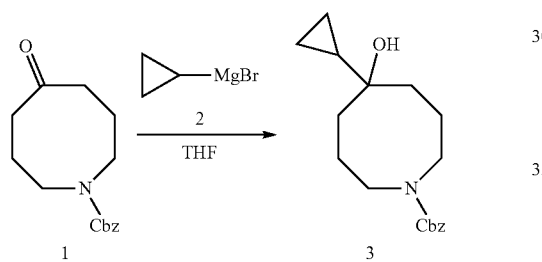

To a solution of Compound 2 (32 mL, 16.1 mmol) in THF (3 mL) was added a solution of compound 1 (0.60 g, 2.3 mmol) in THF (3 mL) at 0° C. under N₂. The reaction mixture was stirred at 20° C. for 16 h. The resulting mixture was quenched with saturated NH₄Cl and extracted with EtOAc (120 mL). The organic layer was dried and concentrated in vacuum to give the crude product, which was purified by flash column chromatography to give the desired product (0.24 g, 34%). $^1$H NMR (400 MHz, CDCl₃) δ 7.28-7.39 (m, 5 H), 5.16-5.17 (m, 2 H), 3.51-3.54 (m, 2 H), 3.33-3.36 (m, 2 H), 1.85-1.87 (m, 2 H), 1.60-1.71 (m, 4 H), 0.93-0.97 (m, 1 H), 0.34-0.37 (m, 4 H).

1.8.2 Preparation of Compound A09

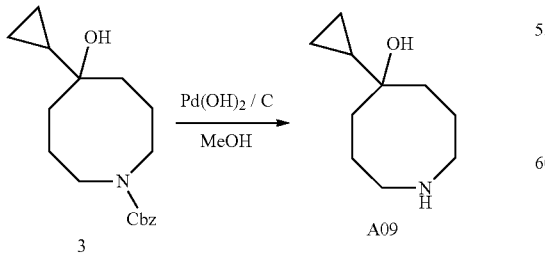

To a solution of compound 3 (0.24 g, 0.8 mmol) in MeOH (15 mL) was added Pd(OH)₂/C (48 mg). The suspension was degassed under vacuum and purged with H₂ several times. The mixture was stirred under H₂ balloon at 25° C. for 16 h. The catalyst was filtered and the filtrate was concentrated in vacuo to give the crude product, which was used in the next step directly (0.13 g, 97%).

1.9 Preparation of Compound A10/11

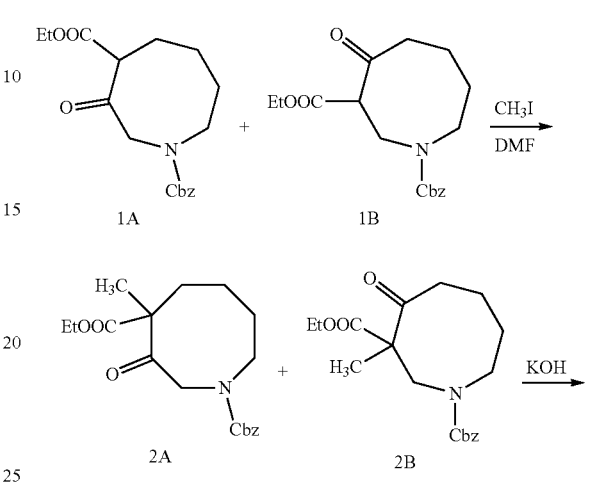

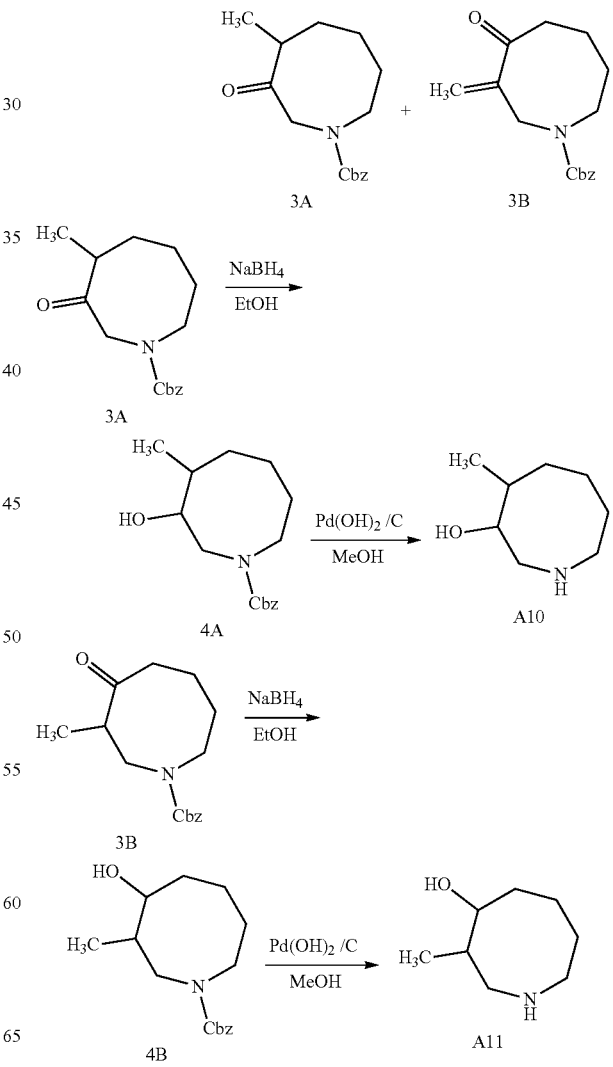

1.9.1 Preparation of Compound 2A/2B

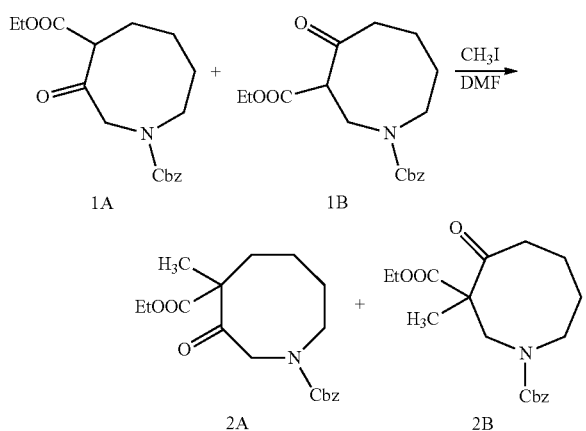

To a mixture of compound 1A and 1B (2.5 g, 7.5 mmol), K₂CO₃ (2.1 g, 15.0 mmol) in DMF (40 mL) was added CH₃I (1.6 g, 11.3 mmol) under N₂, and the reaction mixture was stirred at 16° C. for 16 h. The resulting mixture was diluted with brine and extracted with EA (150 mL). The organic layer was washed with brine, dried over Na₂SO₄ and concentrated in vacuum to give a mixture of compound 2A and 2B (2.5 g, crude), which was used in the next step directly. LCMS: 348.1 [M+1].

1.9.2 Preparation of Compound 3A/3B

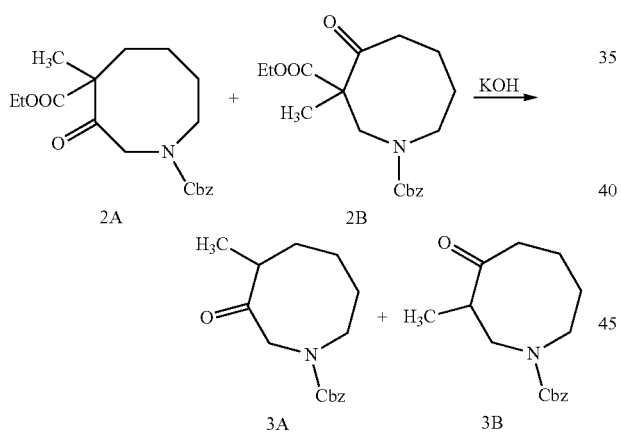

To a solution of compound 2A and 2B (2.5 g, crude) in MeOH (20 mL) was added a solution of KOH (0.73 g, 12.9 mmol) in H₂O (4 mL), the mixture was heated to 70° C. and stirred for 2 h. The mixture was diluted with EA (100 mL) and washed with brine (80 mL). The organic layer was dried over Na₂SO₄ and concentrated in vacuum to give the crude product, which was purified by flash column chromatography to give compound 3A (0.82 g, 39%) and compound 3B (0.68 g, 33%). Compound 3A: ¹H NMR (400 MHz, CDCl₃) δ 7.28-7.42 (m, 5 H), 5.10-5.32 (m, 2 H), 4.48-4.72 (m, 1 H), 4.10-4.40 (m, 1 H), 3.28-3.39 (m, 1 H), 2.81-2.88 (m, 2 H), 1.35-1.85 (m, 5 H), 0.93-1.05 (m, 3 H). Compound 3B: ¹H NMR (400 MHz, CDCl₃) δ 7.28-7.40 (m, 5 H), 5.14-5.32 (m, 2 H), 4.73 (s, 1 H), 3.76-4.15 (m, 2 H), 3.20-3.22 (m, 1 H), 2.32-2.76 (m, 3 H), 1.45-2.07 (m, 4 H), 0.99-1.04 (m, 3 H).

1.9.3 Preparation of Compound 4A

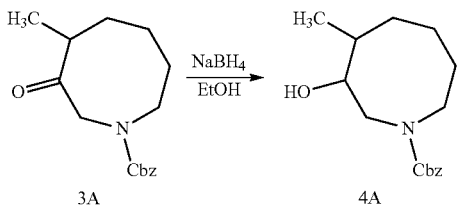

To a solution of compound 3A (0.82 g, 3.0 mmol) in EtOH (15 mL) was added NaBH₄ (0.17 g, 4.5 mmol) at 0° C., and the mixture was stirred at 16° C. for 1 h. The resulting mixture was quenched with NH₄Cl (Sat.) and extracted with EA (80 mL). The organic layer was dried over Na₂SO₄ and concentrated in vacuum to give compound 4A (0.79 g, crude), which was used in the next step directly.

1.9.4 Preparation of Compound A10

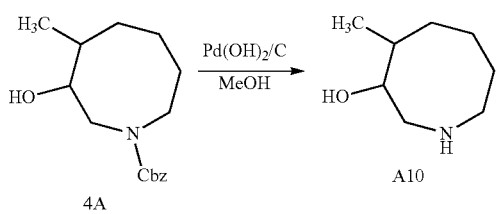

To a solution of compound 4A (0.79 g, 2.9 mmol) in MeOH (40 mL) was added Pd(OH)₂/C (160 mg). The suspension was degassed under vacuum and purged with H₂ several times. The mixture was stirred at 16° C. for 2 h under H₂ atmosphere (15 Psi). The catalyst was filtered and the filtrate was concentrated in vacuum to give the crude product, which was used in the next step directly (0.38 g, 94%).

1.9.5 Preparation of Compound 4B

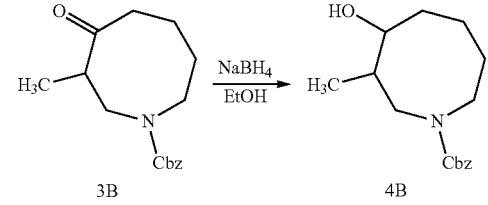

To a solution of compound 3B (0.68 g, 2.5 mmol) in EtOH (15 mL) was added NaBH₄ (0.14 g, 3.7 mmol) at 0° C., and the mixture was stirred at 16° C. for 1 h. The resulting mixture was quenched with NH₄Cl (Sat.) and extracted with EA (80 mL). The organic layer was dried over Na₂SO₄ and concentrated in vacuum to give compound 4B (0.64 g, crude), which was used in the next step directly.

1.9.6 Preparation of Compound A11

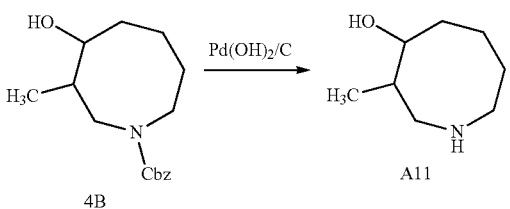

To a solution of compound 4B (0.64 g, 2.3 mmol) in MeOH (30 mL) was added Pd(OH)₂/C (130 mg). The suspension was degassed under vacuum and purged with H₂ several times. The mixture was stirred at 18° C. for 2 h under H₂ atmosphere (15 Psi). The catalyst was filtered and the filtrate was concentrated in vacuum to give the crude product, which was used in the next step directly (0.32 g, 95%).

1.10 Preparation of Compound A12

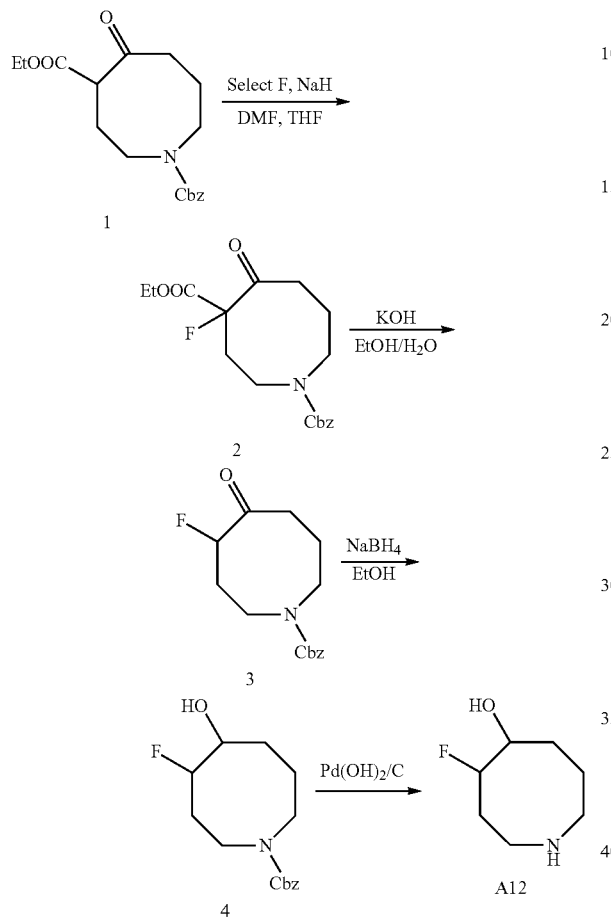

1.10.1 Preparation of Compound 2

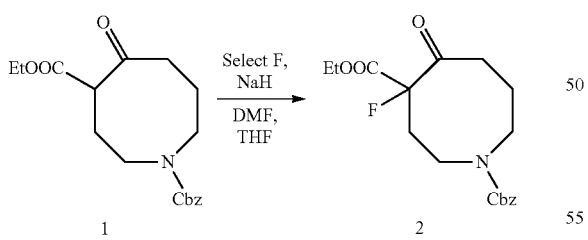

To a suspension of NaH (0.27 g, 6.8 mmol) in THF (10 mL) was added a solution of compound 1 (1.5 g, 4.5 mmol) in THF (10 mL) at 0° C. under N₂, followed by a solution of Select F (1.9 g, 5.4 mmol) in DMF (10 mL) after 0.5 h. The reaction mixture was stirred at 18° C. for 2 h. The resulting mixture was quenched with NH₄Cl (Sat.) and extracted with EA (150 mL). The organic layer was washed with brine, dried over Na₂SO₄ and concentrated in vacuum to give the crude product, which was used in the next step directly (1.8 g, crude).

1.10.2 Preparation of Compound 3

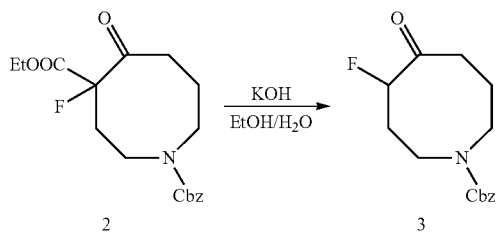

A mixture of compound 2 (1.8 g, crude) and KOH (0.52 g, 9.3 mmol) in MeOH/H₂O (48 mL, MeOH/H₂O=5:1) was heated to 70° C. stirred for 2 h. The mixture was diluted with EA (150 mL) and washed with brine (120 mL). The organic layer was dried over Na₂SO₄ and concentrated in vacuum to give the crude product, which was purified by flash column chromatography to give compound 3 (0.91 g, 72%). ¹H NMR (400 MHz, CDCl₃) δ 7.28-7.41 (m, 5 H), 5.13-5.14 (m, 2 H), 4.86-4.88 (m, 1 H), 3.67-3.99 (m, 2 H), 3.10-3.20 (m, 1 H), 2.60-3.03 (m, 3 H), 2.07-2.40 (m, 4 H).

1.10.3 Preparation of Compound 4

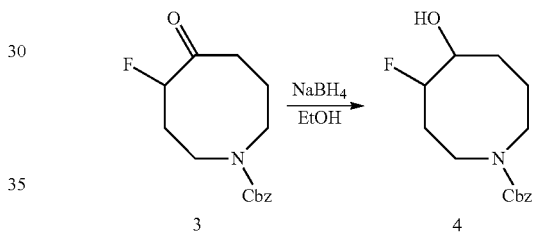

To a solution of compound 3 (0.91 g, 3.3 mmol) in EtOH (15 mL) was added NaBH₄ (0.18 g, 4.7 mmol) at 0° C., and the mixture was stirred at 18° C. for 1 h. The resulting mixture was quenched with NH₄Cl (Sat.) and extracted with EA (80 mL). The organic layer was dried over Na₂SO₄ and concentrated in vacuum to give Compound 4 (0.88 g, crude), which was used in the next step directly.

1.10.4 Preparation of A12

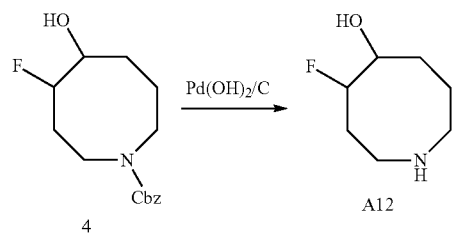

To a solution of compound 4 (0.44 g, 1.5 mmol) in MeOH (25 mL) was added Pd(OH)₂/C (100 mg). The suspension was degassed under vacuum and purged with H₂ several times. The mixture was stirred at 18° C. for 2 h under H₂ atmosphere (15 Psi). The catalyst was filtered and the filtrate was concentrated in vacuum to give the crude product, which was used in the next step directly (0.22 g, 95%).

1.11 Preparation of Compound A13

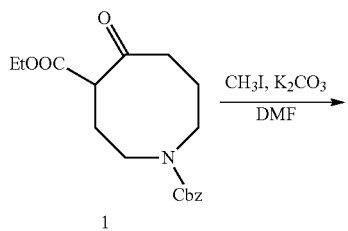

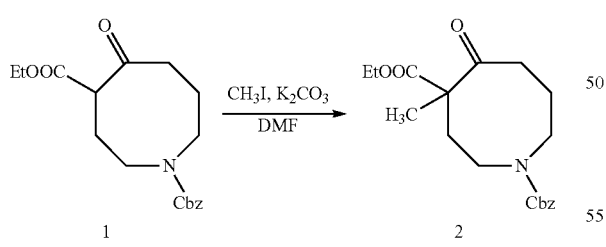

1.11.1 Preparation of Compound 2

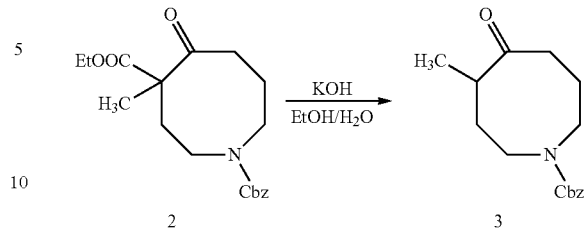

To a suspension of NaH (0.27 g, 6.8 mmol, 60%) in THF (15 mL) was added a solution of compound 1 (1.5 g, 4.5 mmol) in THF (15 mL) at 0° C. under $N_2$, followed by $CH_3I$ (0.96 g, 6.8 mmol) after 0.5 h. The reaction mixture was stirred at 25° C. for 2 h. The resulting mixture was quenched with $NH_4Cl$ (Sat.) and extracted with EA (150 mL). The organic layer was washed with brine, dried over $Na_2SO_4$ and concentrated in vacuum to give the crude product, which was used in the next step directly (1.7 g, crude).

1.11.2 Preparation of Compound 3

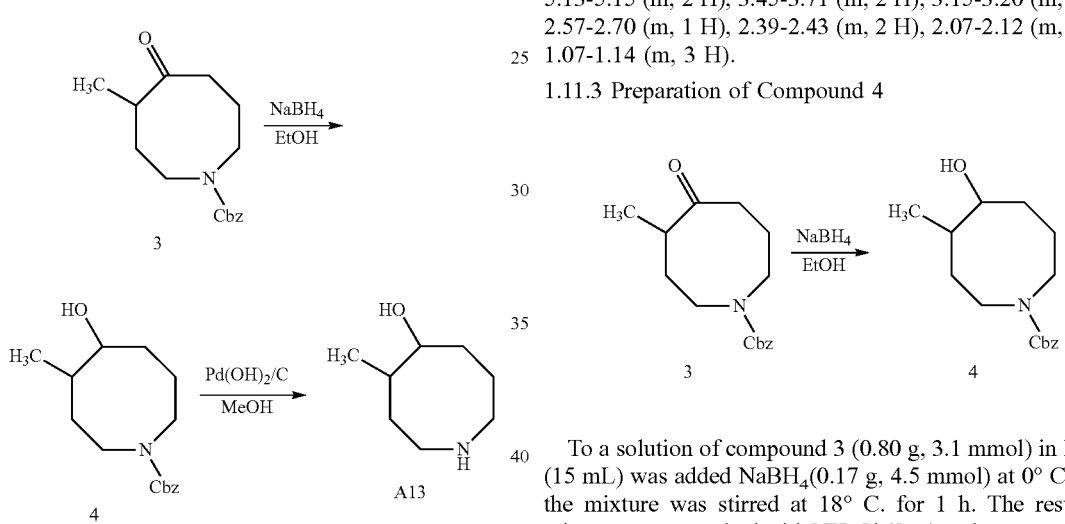

A mixture of compound 2 (1.7 g, crude) and KOH (0.17 g, 4.5 mmol) in $MeOH/H_2O$ (33 mL, $MeOH/H_2O$=10:1) was heated to 70° C. and stirred for 2 h. The mixture was diluted with EA (150 mL) and washed with brine (100 mL). The organic layer was dried over $Na_2SO_4$ and concentrated in vacuum to give the crude product, which was purified by flash column chromatography to give compound 3 (0.80 g, 65%). $^1$H NMR (400 MHz, $CDCl_3$) δ 7.28-7.40 (m, 5 H), 5.13-5.15 (m, 2 H), 3.45-3.71 (m, 2 H), 3.15-3.20 (m, 2 H), 2.57-2.70 (m, 1 H), 2.39-2.43 (m, 2 H), 2.07-2.12 (m, 4 H), 1.07-1.14 (m, 3 H).

1.11.3 Preparation of Compound 4

To a solution of compound 3 (0.80 g, 3.1 mmol) in EtOH (15 mL) was added $NaBH_4$ (0.17 g, 4.5 mmol) at 0° C., and the mixture was stirred at 18° C. for 1 h. The resulting mixture was quenched with $NH_4Cl$ (Sat.) and extracted with EA (80 mL). The organic layer was dried over $Na_2SO_4$ and concentrated in vacuum to give compound 4 (0.80 g, crude), which was used in the next step directly.

1.11.4 Preparation of Compound A13

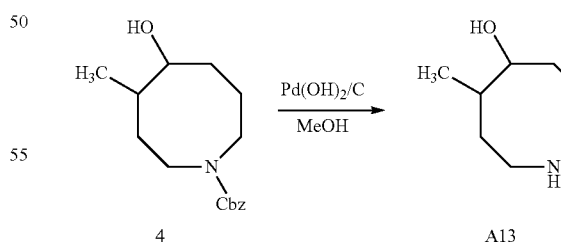

To a solution of compound 4 (0.40 g, 1.4 mmol) in MeOH (25 mL) was added $Pd(OH)_2$/C (100 mg). The suspension was degassed under vacuum and purged with $H_2$ several times. The mixture was stirred at 18° C. for 2 h under $H_2$ atmosphere (15 Psi). The catalyst was filtered and the filtrate was concentrated in vacuum to give the crude product, which was used in the next step directly (0.19 g, 94%).

1.12 Preparation of Compound A14

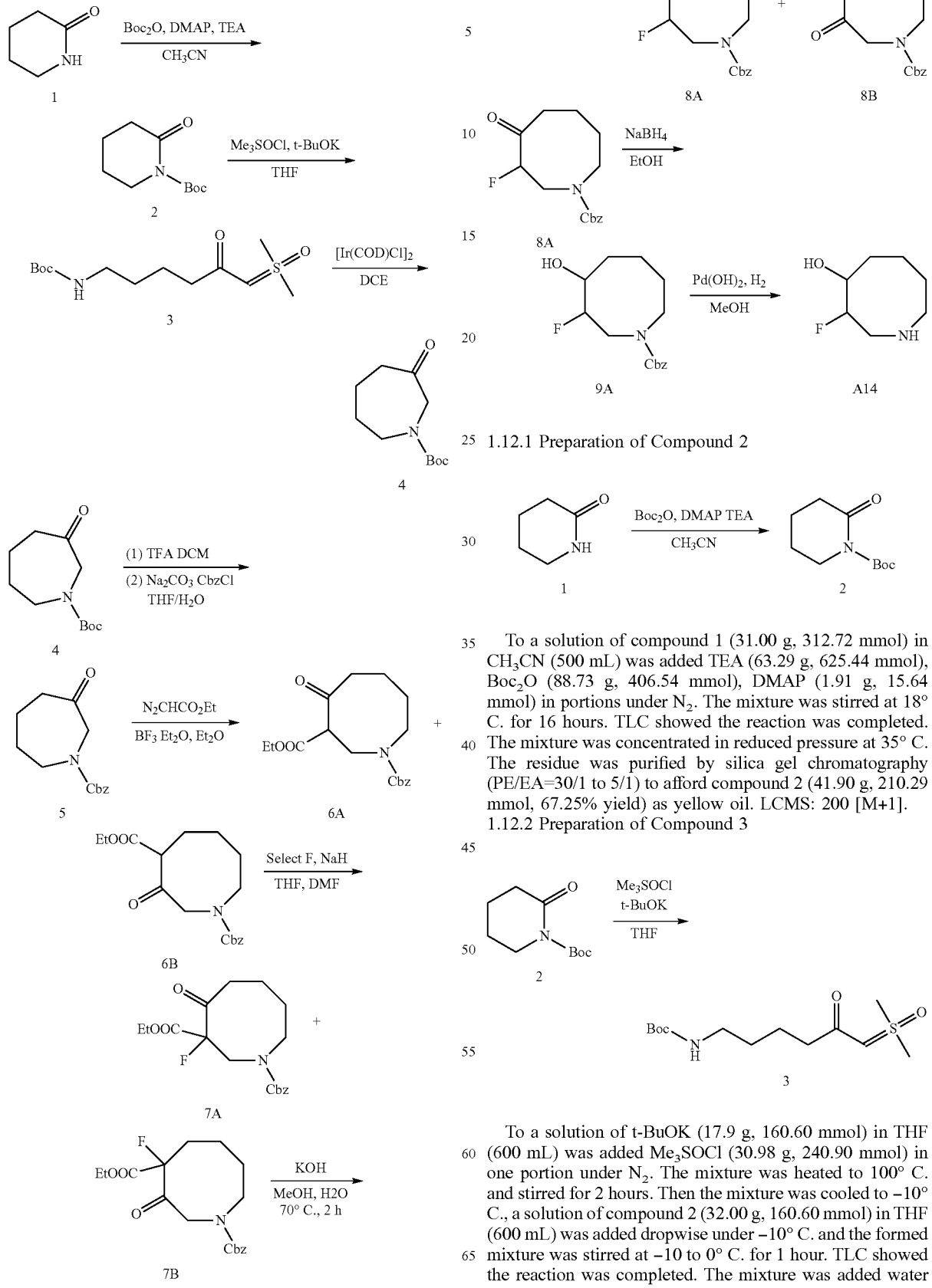

1.12.1 Preparation of Compound 2

To a solution of compound 1 (31.00 g, 312.72 mmol) in CH₃CN (500 mL) was added TEA (63.29 g, 625.44 mmol), Boc₂O (88.73 g, 406.54 mmol), DMAP (1.91 g, 15.64 mmol) in portions under N₂. The mixture was stirred at 18° C. for 16 hours. TLC showed the reaction was completed. The mixture was concentrated in reduced pressure at 35° C. The residue was purified by silica gel chromatography (PE/EA=30/1 to 5/1) to afford compound 2 (41.90 g, 210.29 mmol, 67.25% yield) as yellow oil. LCMS: 200 [M+1].

1.12.2 Preparation of Compound 3

To a solution of t-BuOK (17.9 g, 160.60 mmol) in THF (600 mL) was added Me₃SOCl (30.98 g, 240.90 mmol) in one portion under N₂. The mixture was heated to 100° C. and stirred for 2 hours. Then the mixture was cooled to −10° C., a solution of compound 2 (32.00 g, 160.60 mmol) in THF (600 mL) was added dropwise under −10° C. and the formed mixture was stirred at −10 to 0° C. for 1 hour. TLC showed the reaction was completed. The mixture was added water (100 mL) and extracted with EA (200 mL*3). The combined organic phase was dried over anhydrous Na$_2$SO$_4$, and concentrated in vacuum. The residue was washed with PE/EA (50 mL, PE/EA=10/1) and filtered to afford compound 3 (37.60 g, 80.34%) as white solid. LCMS: 292 [M+1].

1.12.3 Preparation of Compound 4

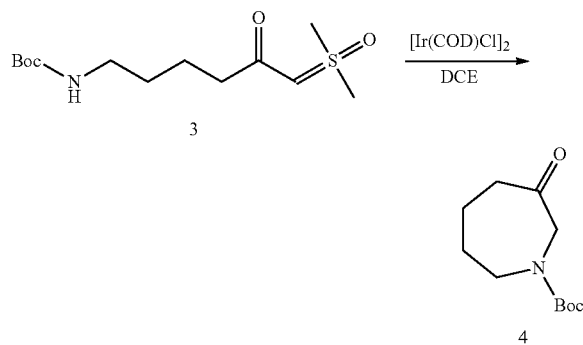

To a solution of compound 3 (10 g, 0.034 mol) in DCE (800 mL) was added [Ir(COD)Cl]$_2$ (229 mg, 0.34 umol) in one portion under N$_2$. The mixture was heated to 70° C. and stirred for 16 hours. TLC showed the reaction was completed. The mixture was cooled to 18° C., and concentrated in reduced pressure at 40° C. The residue was washed with water (50 mL) and extracted with EA (100 mL*2). The combined organic phase was dried with anhydrous Na$_2$SO$_4$, concentrated in vacuum to afford compound 4 (6.7 g, crude) as oil. LCMS: 214 [M+1].

1.12.4 Preparation of Compound 5

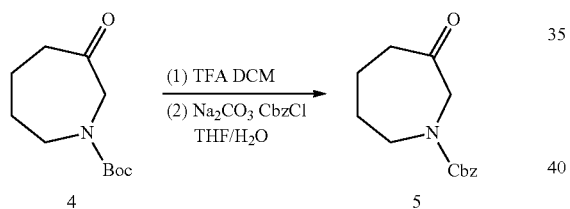

To a mixture of compound 4 (12.9 g, 0.060 mol) in MeOH (100 mL) was added HCl/MeOH (30 mL, 4M). The mixture was stirred at 18° C. for 0.5 h. TLC showed the reaction was completed. The solution was washed with MeOH (30 mL*3) and concentrated to remove the solvent. Then THF/H$_2$O (200 mL) was added, followed by Na$_2$CO$_3$ (12.72 g, 0.12 mol), CbzCl (15.3 g, 0.09 mol). The mixture was stirred at 18° C. for 2 hours. The mixture was extracted with EA (100 mL*2). The combined organic phase was dried with anhydrous Na$_2$SO$_4$, concentrated in vacuum. The residue was purified by silica gel chromatography (PE/EA=30/1 to 10/1) to afford compound 5 (14.3 g, 96%) as yellow oil. LCMS: 248 [M+1].

1.12.5 Preparation of Compound 6A/6B

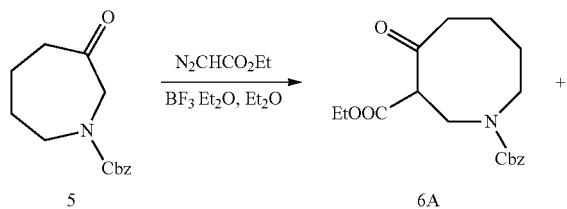

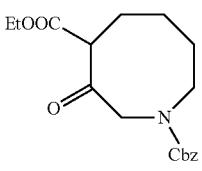

To a solution of compound 5 (13.10 g, 52.97 mmol) in Et$_2$O (1000 mL) was added BF$_3$.Et$_2$O (26.31 g, 185.40 mmol), N$_2$CHCO$_2$Et (21.15 g, 185.40 mmol) slowly at −30° C. under N$_2$. The mixture was stirred at −30° C. for 1 hour. Then it was stirred at 18° for 16 hours. LCMS showed the reaction was completed. The mixture was quenched with saturated NaHCO$_3$ (200 mL) and extracted with Et$_2$O (300 mL*2). The combined organic phase was dried over anhydrous Na$_2$SO$_4$, concentrated in vacuum. The residue was purified by silica gel chromatography (PE/EA=30/1 to 5/1) to afford compound 6 (19.80 g, crude) as mixture. LCMS: 334 [M+1].

1.12.6 Preparation of Compound 7A/7B

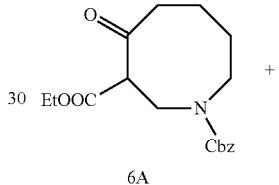

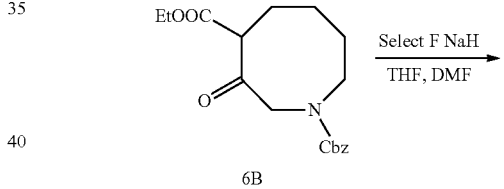

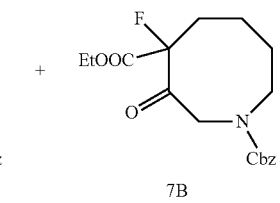

To a solution of compound 6 (19.80 g, 59.39 mmol) as mixture in THF (400 mL) was added NaH (2.85 g, 71.27 mmol, 60%) in portions under N$_2$ under −10° C., and it was stirred at −10° C. for 1 hour. Then a solution of Select F (25.25 g, 71.27 mmol) in DMF (50 mL) was added to the mixture in portions at −10° C. under N$_2$. The mixture was stirred at −10° C. for 30 min. Then the mixture was warmed to 18° C. and stirred for 2.5 hours. LCMS showed the reaction was completed. The mixture was poured into saturated NH$_4$Cl (50 mL) and extracted with EA (100 mL*2). The combined organic phase was dried over anhydrous Na$_2$SO$_4$, concentrated in vacuum. The residue was purified by silica gel chromatography (PE/EA=30/1 to 10/1) to afford compound 7 (13.40 g, crude) as a mixture of 7A and 7B as yellow oil. LCMS: 352 [M+1].

1.12.7 Preparation of Compound 8A/8B

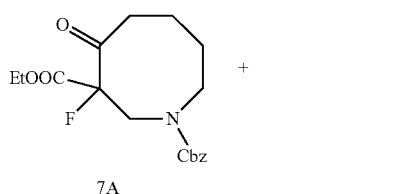

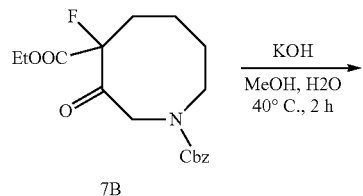

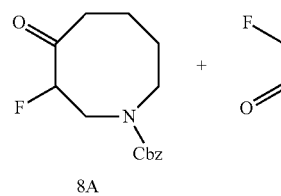

To a mixture of compound 7 (13.40 g, 38.14 mmol) in MeOH/H$_2$O (200 mL) was added KOH (4.28 g, 76.28 mmol) in one portion under N$_2$. The mixture was stirred at 40° C. for 2 hours. LCMS showed the reaction was completed. The mixture was cooled to 18° C. and adjusted to pH=7 by HCl (4N) under 0° C. The mixture was extracted with EA (200 mL*2), the organic layer was dried over anhydrous Na$_2$SO$_4$, concentrated in vacuum. The residue was purified by flash column chromatography to afford compound 8A (430.00 mg, 4.22%) as yellow oil and a mixture of compound 8A and 8B (4.5 g, mixture). LCMS: 280 [M+1].

1.12.8 Preparation of Compound 9A

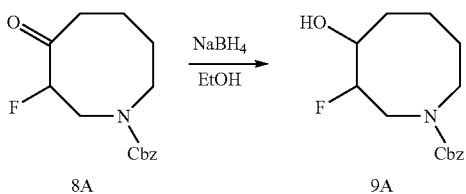

To a solution of compound 8A (430.00 mg, 1.54 mmol) in EtOH (10 mL) was added NaBH$_4$ (87.39 mg, 2.31 mmol) in one portion at 18° C. under N$_2$. The mixture was stirred at 18° C. for 2 hours. LCMS showed the reaction was completed. The mixture was concentrated in reduced pressure at 35° C. The residue was poured into water (10 mL) and extracted with EA (50 mL*2). The combined organic phase was dried over anhydrous Na$_2$SO$_4$, concentrated in vacuum. The residue was purified by silica gel chromatography (PE/EA=20/1 to 3/1) to afford compound 9A (370.00 mg, 85.40%) as yellow oil. LCMS: 282 [M+1].

1.12.9 Preparation of Compound A14

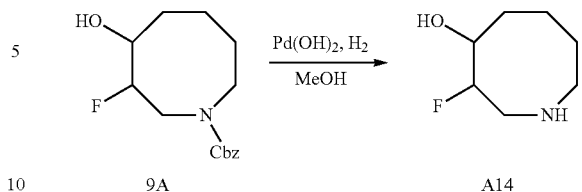

To a solution of compound 9A (370.00 mg, 1.32 mmol) in MeOH (10 mL) was added Pd(OH)$_2$ (100.00 mg, 722.44 umol) in one portion at 18° C. under N$_2$. The suspension was degassed under vacuum and purged with H$_2$ several times. The mixture was stirred under H$_2$ at 18° C. for 16 hours. TLC showed the reaction was completed. The mixture was filtered and concentrated in vacuum to compound A14 (180.00 mg, crude) as yellow oil.

1.13 Preparation of Compound A15

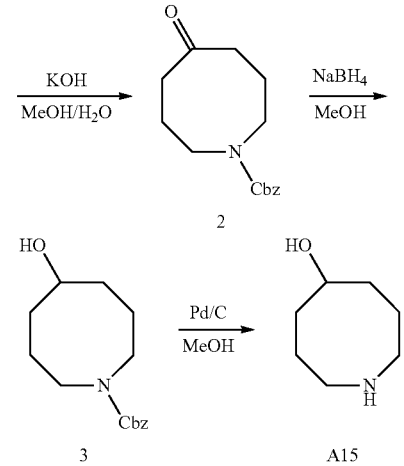

1.13.1 Preparation of Compound 2

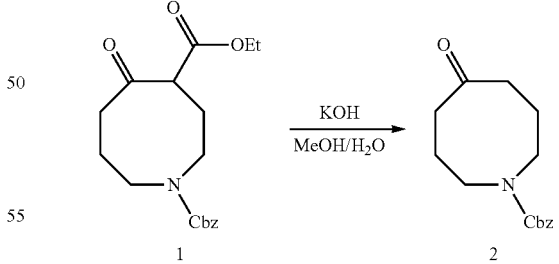

To a solution of compound 1 (1.2 g, 3.6 mmol) in EtOH (15 mL) was added aq KOH (11.6 mL, 1 M). The resulting mixture was stirred at 80° C. for 3 hours. The mixture was concentrated to remove solvents. The residue was dissolved in H$_2$O (10 mL), extracted with EA (20 mL×3). The organic layer was dried over Na$_2$SO$_4$, filtered and the filtrates were concentrated to dryness. The residue was purified by silica gel chromatography (PE:EA=10:1 to 5:1) to afford desired compound 2 (0.6 g, yield: 63.8%) as colorless oil.

1.13.2 Preparation of Compound 3

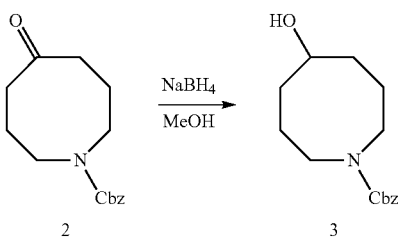

To a solution of compound 2 (0.6 g, 2.3 mmol) in EtOH (10 mL) was added NaBH$_4$ (87 mg, 2.3 mmol). The mixture was stirred at 25 to 30° C. for 2 hours. The mixture was concentrated to remove solvents and the residue was dissolved in H$_2$O (10 mL), then the aqueous layer was extracted with EA (25 mL×3), the organic layer was dried over Na$_2$SO$_4$, filtered, the filtrate was concentrated to give desired compound 3 (0.51 g, 85%) as yellow oil.

1.13.3 Preparation of Compound A15

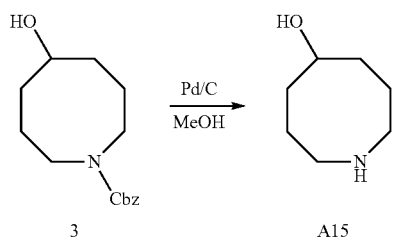 [SMILES: "MeOH" ; O=C(OCc1ccccc1)N1CCCC(O)CCC1 ; "Pd/C" ; OC1CCCNCCC1 ; "A15"]

To a solution of compound 3 (0.51 g, 1.9 mmol) in MeOH (10 mL) was added Pd/C (0.1 g) under N$_2$. The suspension was degassed under vacuum and purged with H$_2$ several times. The mixture was stirred under H$_2$ (15 Psi) at 25° C. for 16 hours. The mixture was concentrated under vacuum to give compound A15 (200 mg, 83.3%).

1.14 Preparation of Compound A16

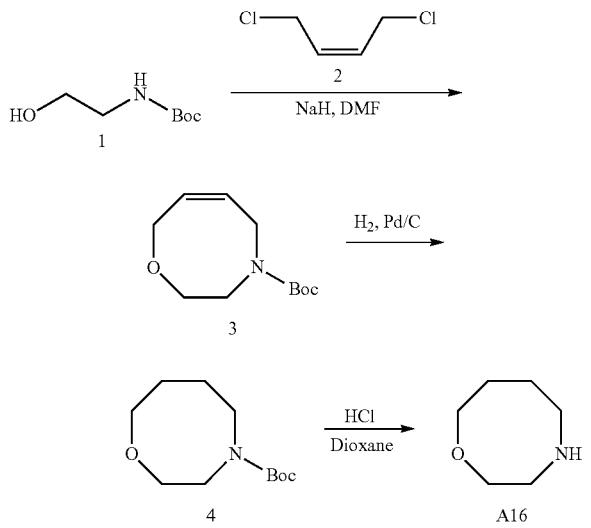

1.14.1 Preparation of Compound 3

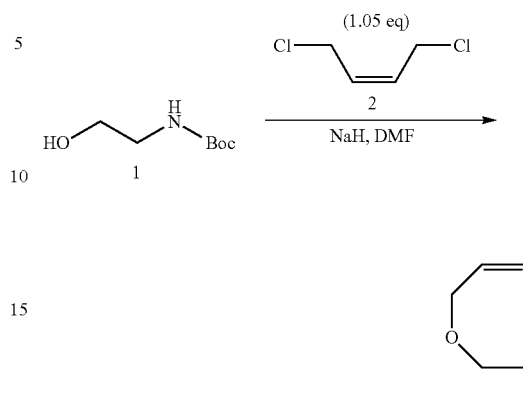

To a mixture of compound 1 (20 g, 0.124 mol) in DMF (300 mL) was added NaH (12.0 g, 0.3 mol, 60%) at 0° C., then followed by compound 2 (16 g, 0.124 mol). The reaction mixture was stirred at 25° C. for 16 hours. The mixture was quenched by NH$_4$Cl (600 mL), extracted with EA (150 mL×3). The organic layer was washed with brine (150 mL×3), dried over Na$_2$SO$_4$, filtered and concentrated to dryness. The residue was purified by silica gel chromatography (PE:EA=10:1 to 5:1) to afford desired compound 3 (1.2 g, 4.6%) as brown solid. $^1$H NMR (400 MHz, CDCl$_3$) δ 5.91-5.74 (m, 1H), 5.65-5.41 (m, 1 H), 4.28-4.17 (m, 2 H), 4.05-3.89 (m, 2 H), 3.79-3.66 (m, 2 H), 3.54-3.38 (m, 2 H), 1.44 (s, 9 H).

1.14.2 Preparation of Compound 4

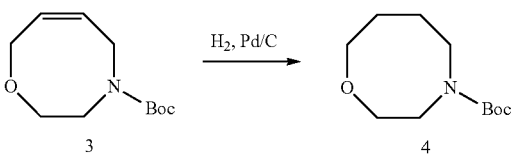

To a solution of compound 3 (0.2 g, 0.93 mmol) in MeOH (10 mL) was added Pd/C (0.05 g) under N$_2$. The suspension was degassed under vacuum and purged with H$_2$ several times. The mixture was stirred under H$_2$ (15 Psi) at 20° C. for 16 hours. The mixture was concentrated under vacuum to give compound 4 (200 mg, 93.3%).

1.14.3 Preparation of Compound A16

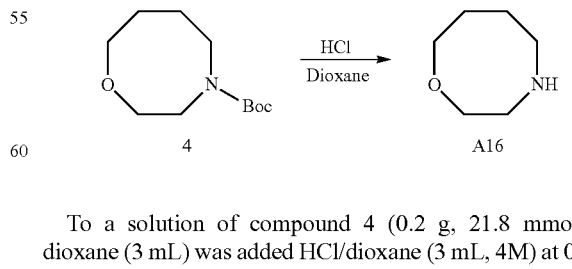

To a solution of compound 4 (0.2 g, 21.8 mmol) in dioxane (3 mL) was added HCl/dioxane (3 mL, 4M) at 0° C., the mixture was stirred at 0° C. for 1 hours. Then the mixture was concentrated to give compound A16 (0.1 g, crude) as white solid.

1.15 Preparation of Compound A17/A18

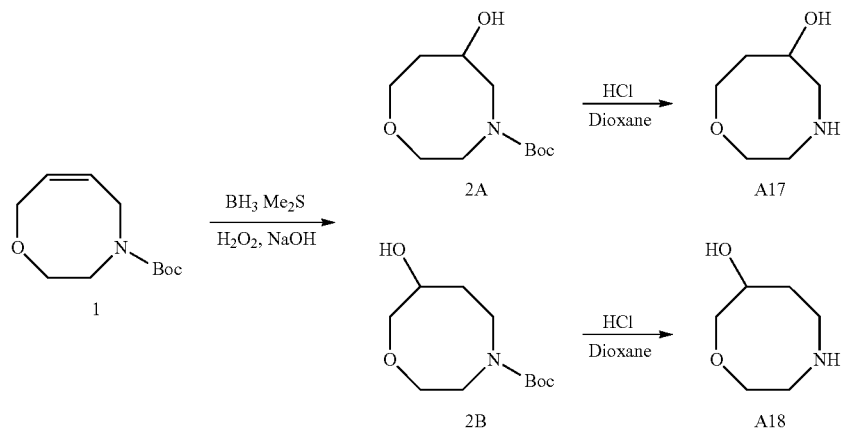

1.15.1 Preparation of Compound 2A/2B

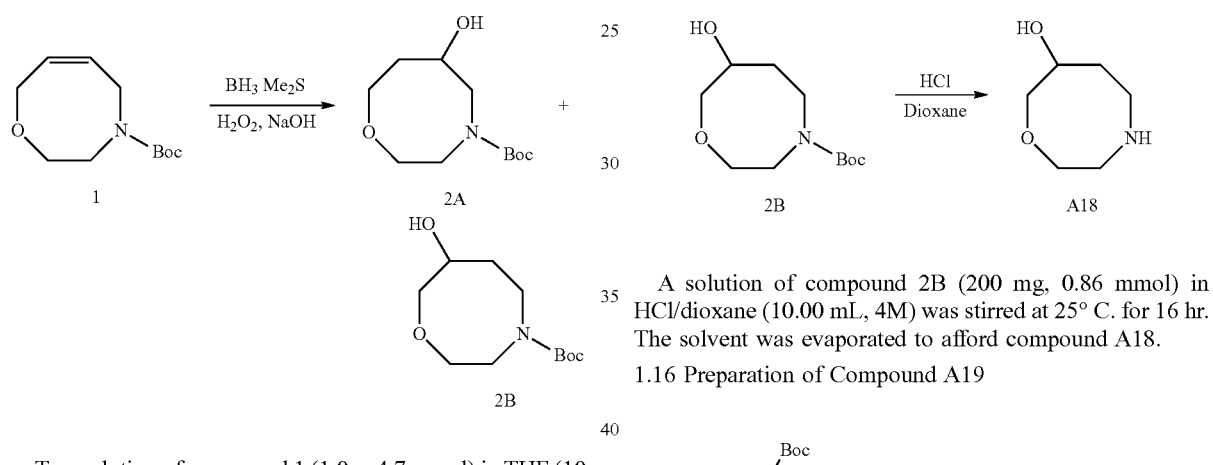

To a solution of compound 1 (1.0 g, 4.7 mmol) in THF (10 mL) was added BH$_3$ (0.9 mL, 9 mmol). The mixture was stirred at 25 to 30° C. for 16 hours. Then aqueous NaOH (0.30 g, 2 mL), H$_2$O$_2$ (0.8 g, 18 mmol) was added dropwise. And the mixture was extracted with EA (25 mL×3), the organic layer was dried over Na$_2$SO$_4$, filtered, the filtrate was concentrated to dryness. The residue was purified with column chromatography on silica gel (PE:EA=1:1 to 1:2) to give compound 2A (400 mg) and compound 2B (150 mg) as yellow oil.

1.15.2 Preparation of A11

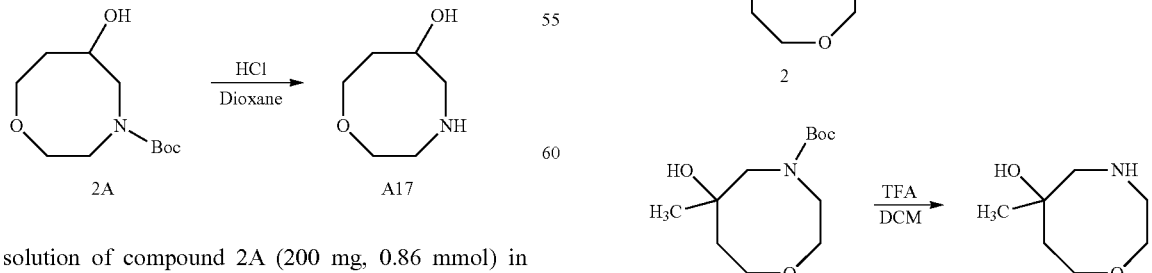

A solution of compound 2A (200 mg, 0.86 mmol) in HCl/dioxane (10.00 mL, 4M) was stirred at 25° C. for 16 hr. TLC detected the reaction was completed. The solvent was evaporated to afford compound A17.

1.15.3 Preparation of Compound A18

A solution of compound 2B (200 mg, 0.86 mmol) in HCl/dioxane (10.00 mL, 4M) was stirred at 25° C. for 16 hr. The solvent was evaporated to afford compound A18.

1.16 Preparation of Compound A19

1.16.1 Preparation of Compound 2

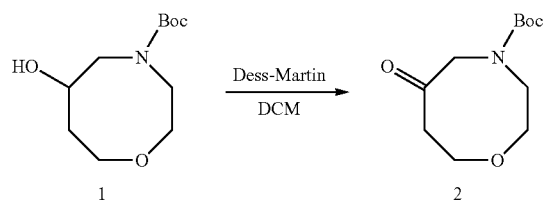 [SMILES: CC(C)(C)OC(=O)N1CCOCCC(O)C1 ; CC(C)(C)OC(=O)N1CCOCCC(=O)C1]

To a mixture of tert-butyl 6-hydroxy-1,4-oxazocane-4-carboxylate (1.40 g, 6.05 mmol, 1.00 Eq) in DCM (100 mL), was added Dess-Martin (3.85 g, 9.08 mmol, 1.50 Eq) in one portion at 20° C. under $N_2$. The mixture was stirred at 20° C. for 12 hr. TLC showed the reaction was completed. The mixture was poured into saturated $NH_4Cl$ (30 mL) and stirred for 20 min. The aqueous phase was extracted with DCM (20 mL*2). The combined organic phase was washed with saturated brine (20 mL*2), dried over anhydrous $Na_2SO_4$, filtered and concentrated in vacuum. The residue was purified by silica gel chromatography (PE/EA=10/1) to afford tert-butyl 6-oxo-1,4-oxazocane-4-carboxylate (1.10 g, 4.80 mmol, 79.30% yield) as yellow oil.

1.16.2 Preparation of Compound 3

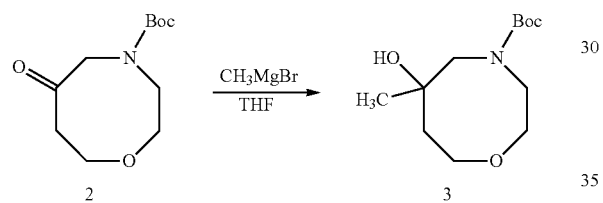

To a mixture of MeM r (1.40 g, 11.78 mmol, 3.00 Eq) in THF (50 mL), was added tert-butyl 6-oxo-1,4-oxazocane-4-carboxylate (900.00 mg, 3.93 mmol, 1.00 Eq) at 0° C. under $N_2$. The mixture was stirred at 0° C. for 1 hr. Then heated to 20° C. and stirred for 2 hours. TLC showed the reaction was completed. The mixture was poured into $NH_4Cl$ (50 mL) and stirred for 20 min. The aqueous phase was extracted with EA (40 mL*3). The combined organic phase was washed with saturated brine (20 mL*2), dried over anhydrous $Na_2SO_4$, filtered and concentrated in vacuum. The residue was purified by silica gel chromatography (PE/EA=15/1) to afford tert-butyl 6-hydroxy-6-methyl-1,4-oxazocane-4-carboxylate (750.00 mg, 3.06 mmol, 77.80% yield) as yellow oil.

1.16.3 Preparation of Compound A19

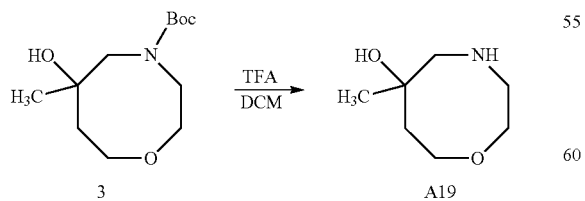

To a mixture of tert-butyl 6-hydroxy-6-methyl-1,4-oxazocane-4-carboxylate (1.00 g, 4.08 mmol, 1.00 Eq) in DCM (8 mL), was added TFA (4 mL) at 20° C. under $N_2$. The mixture was stirred at 20° C. for 2 hr. TLC showed the reaction was completed. The mixture was concentrated to afford 6-methyl-1,4-oxazocan-6-ol (1.50 g, crude) as crude product.

1.17 Preparation of Compound A20

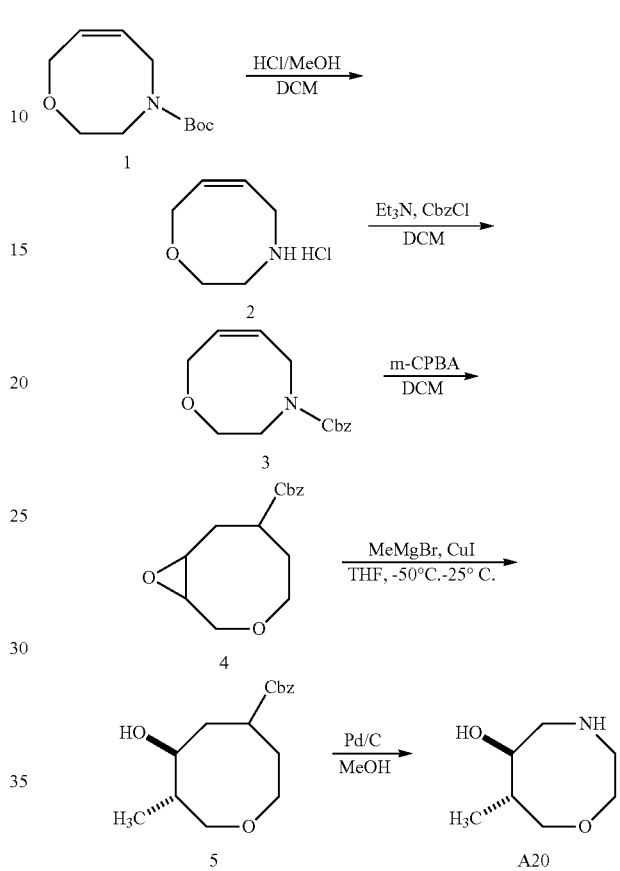

1.17.1 Preparation of Compound 2

To a solution of compound 1 (10.00 g, 46.89 mmol, 1.00 Eq) in DCM (20 mL) was added HCl/MeOH (20 mL, 4 M). The mixture was stirred at 0° C. for 1 h. The mixture was concentrated to compound 2 (6.50 g, 43.44 mmol, 92.65% yield) as white solid.

1.17.2 Preparation of Compound 3

To a mixture of compound 2 (3.50 g, 23.39 mmol, 1.00 Eq) in DCM (20 mL) was added TEA (5.92 g, 58.48 mmol, 2.50 Eq) and CbzCl (5.99 g, 35.09 mmol) in one portion. The mixture was stirred at 25° C. for 16 h. The mixture was concentrated and the residue was purified by column chromatography on silica gel (PE/EA=5/1 to 3/1) to afford compound 3 (4.10 g, 16.58 mmol, 70.88% yield) as yellow soil.

1.17.3 Preparation of Compound 4

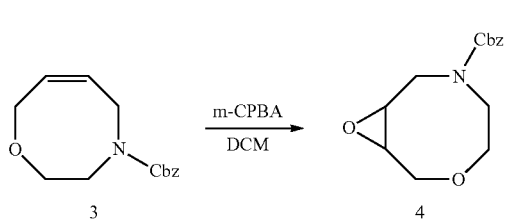 [SMILES: O=C(OCc1ccccc1)N1C/C=C\COCC1 ; O=C(OCc1ccccc1)N1CCOCC2OC2C1]

To a mixture of compound 3 (4.00 g, 16.12 mmol, 1.00 Eq) in DCM (40 mL) was added m-CPBA (6.96 g, 40.4 mmol, 2.50 Eq). The mixture was stirred at 25° C. for 2 h. The mixture was washed with NaHCO$_3$ (30 mL) and Na$_2$SO$_3$ (30 mL), brine (30 mL), dried over Na$_2$SO$_4$ and concentrated to dryness. The residue was purified by column chromatography on silica gel (PE:EA=5:1 to 3:1) to give compound 4 (1.9 g, 45.2%).

1.17.4 Preparation of Compound 5

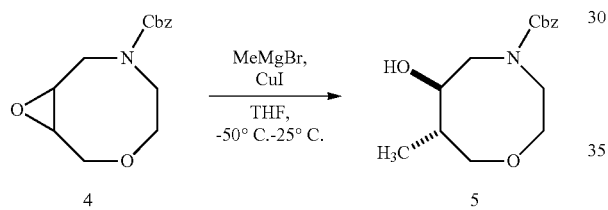

To a suspension of CuI (1.92 g, 10.06 mmol) in THF (15 mL) was added MeM r (1.2 g, 10.06 mmol) at −50° C., then it was stirred at −50° C. for 0.5 h. Compound 4 (0.53 g, 2 mmol) was added into the mixture at −50° C., the reaction was allowed to warm to 25° C. and stirred for 2 h, TLC showed the material was consumed complete. The reaction was quenched with NH$_4$Cl (40 mL), extracted with EA (100 mL), the organic layer was dried over anhydrous Na$_2$SO$_4$ and concentrated to dryness, the residue was purified by column chromatography on silica gel (PE:EA=5:1 to 3:1) to give compound 5B (0.2 g).

1.17.5 Preparation of Compound A20

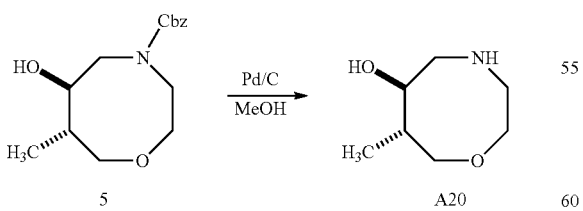

To a solution of compound 5 (100.00 mg, 374.11 umol, 1.00 Eq) in MeOH (5 mL) was added Pd/C (0.02 g) under N$_2$. The suspension was degassed under vacuum and purged with H$_2$ several times. The mixture was stirred under H$_2$ (50 psi) at 25° C. for 16 hours. TLC (PE:EA=1:1) showed the starting material was consumed completely. The reaction mixture was filtered and the filter was concentrated to give compound A20 (50.00 mg, 300.39 umol, 85.29% yield) as colorless oil.

1.18 Preparation of Compound A21/A22

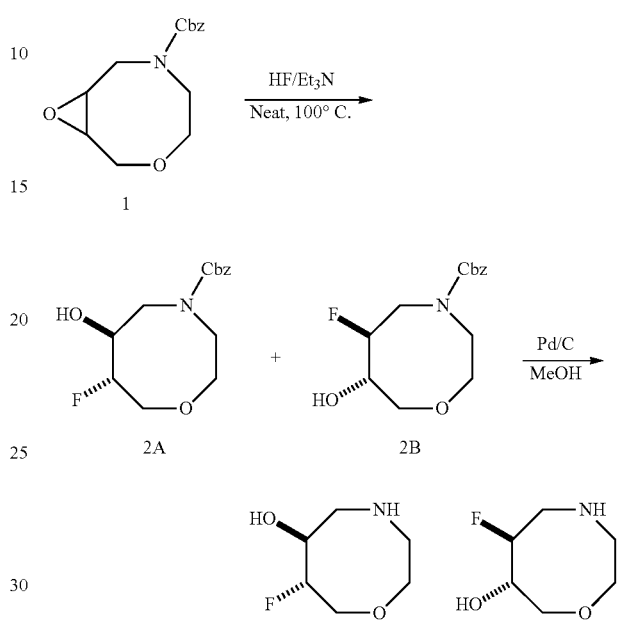

1.18.1 Preparation of Compound 2A/2B

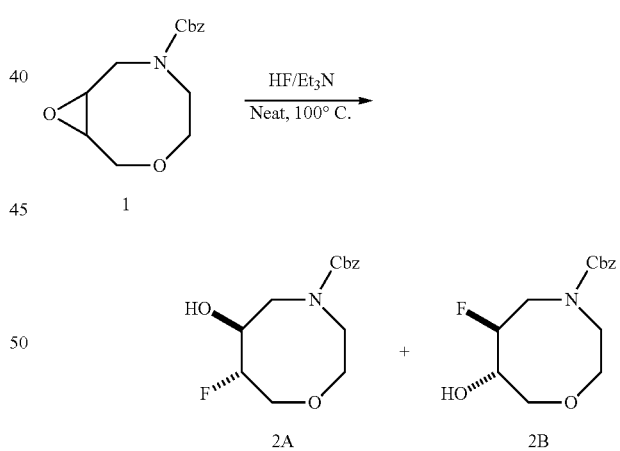

Compound 1 (1.10 g, 4.18 mmol) and HF/Et$_3$N (5.38 g, 33.4 mmol) were charged in a 100 mL single-necked round bottom flask. The mixture was stirred at 100° C. for 16 h under N$_2$. TLC showed the reaction was complete. Then the mixture was diluted in DCM (20 mL), washed with water (30 mL), dried over anhydrous Na$_2$SO$_4$ and concentrated to dryness. The residue was purified by column chromatography on silica gel (PE:EA=1:1) to give an inseparable mixture of compound 2A and 2B (300 mg, 25.33%) as colorless oil.

1.18.2 Preparation of A21/A22

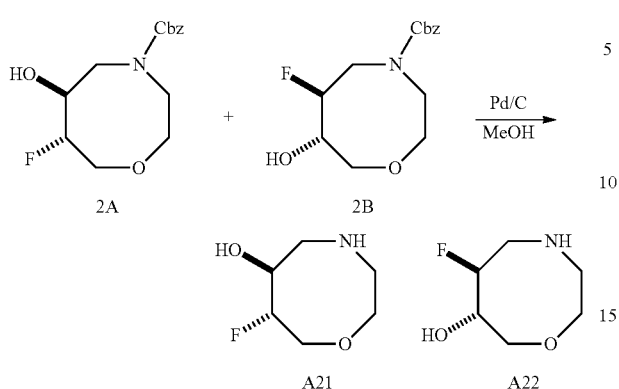

To a solution of compound 2A and 2B (250.00 mg, 882.49 umol, 1.00 Eq) in MeOH (10 mL) was added Pd/C under N₂. The suspension was degassed under vacuum and purged with H₂ several times. The mixture was stirred under H₂ (15 psi) at 25° C. for 16 rs. TLC (PE:EA=1:1) showed the starting material was consumed completely. The reaction mixture was filtered and the filter was concentrated to give an inseparable mixture of A21 and A22 (100.00 mg, 670.42 umol, 75.97% yield) as yellow oil. The mixture was used to prepare a final target directly and separated regiomers with supercritical fluid chromatography.

1.19 Preparation of Compound A23

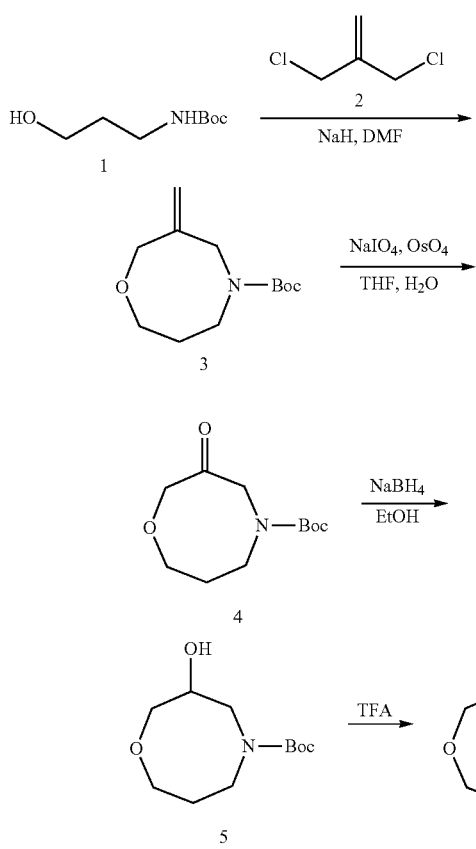

1.19.1 Preparation of Compound 3

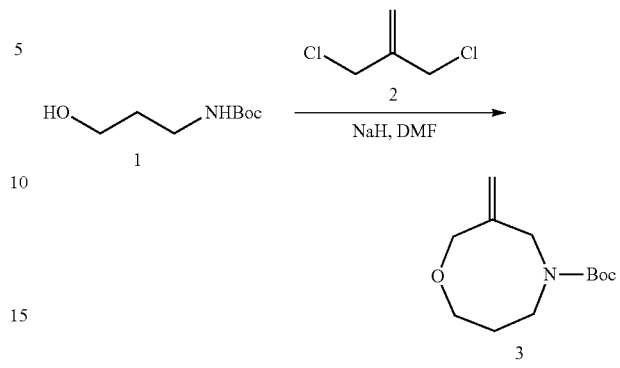

To a solution of compound 1 (1.00 g, 5.71 mmol, 1.00 Eq) in DMF (20 mL) was added NaH (525.32 mg, 13.13 mmol, 60%, 2.30 Eq) at −10° C. and stirred at −10~0° C. for 30 min, compound 2 (713.39 mg, 5.71 mmol, 1.00 Eq) was added drop-wise at 0° C. over a period of 15 min under N₂. The reaction mixture was stirred at 25° C. for 2 hours. TLC (PE/EA=3:1) showed the starting material was consumed completely. The reaction was quenched by ice water slowly and then extracted with EA. The combined organic phase was washed with saturated brine, dried over anhydrous Na₂SO₄, filtered and concentrated in vacuum. The residue was purified by silica gel chromatography (PE:EA=5:1) to give the pure compound 3 (250.00 mg, 1.10 mmol, 19.26% yield) as colorless oil.

1.19.2 Preparation of Compound 4

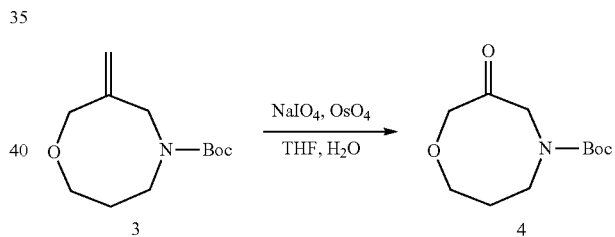

A solution of compound 3 (250.00 mg, 1.10 mmol, 1.00 Eq) in THF (6 mL) and H₂O (3 mL) was stirred at 25° C. for 1 hr, TLC showed the reaction was completed, the mixture was diluted with EA, washed with Na₂SO₃ and brine, the organic phase was dried over anhydrous Na₂SO₄, filtered and concentrated to give compound 4 (180.00 mg, 785.10 umol, 71.37% yield) as light yellow oil.

1.19.3 Preparation of Compound 5

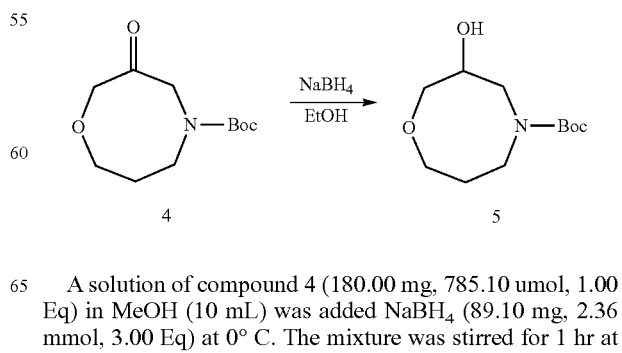

A solution of compound 4 (180.00 mg, 785.10 umol, 1.00 Eq) in MeOH (10 mL) was added NaBH₄ (89.10 mg, 2.36 mmol, 3.00 Eq) at 0° C. The mixture was stirred for 1 hr at 27° C., TLC showed the reaction was completed, the mixture was poured into sat.NH₄Cl, extracted with EA, the organic phase was dried over anhydrous Na₂SO₄, filtered and concentrated to give compound 5 (140.00 mg, 605.30 umol, 77.10% yield) as colorless oil.

1.19.4 Preparation of Compound A23

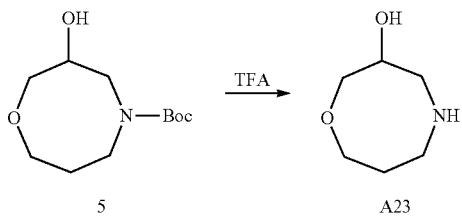

To a solution of compound 5 (140.00 mg, 605.30 umol, 1.00 Eq) in dioxane (5 mL) was added HCl/dioxane (5 mL, 4M), the mixture was stirred at 27° C. for 1 hr, TLC showed the reaction was completed, the reaction solution was concentrated to give compound A23 (80.00 mg, crude) as white solid.

1.20 Preparation of Compound A24

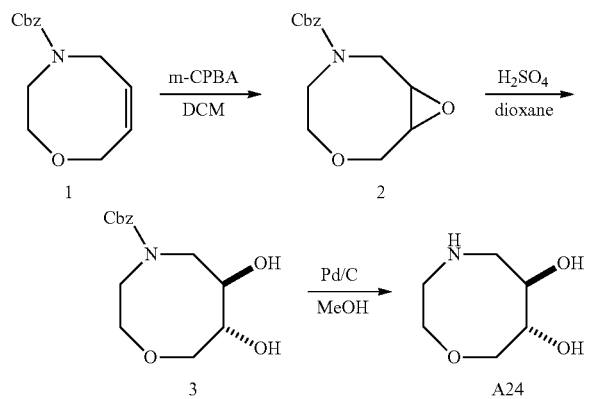

1.20.1 Preparation of Compound 2

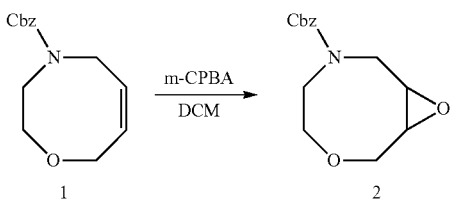 [SMILES: O=C(OCc1ccccc1)N1C/C=C\COCC1 ; O=C(OCc1ccccc1)N1CCOCC2OC2C1]

To a solution of compound 1 (1.00 g, 4.04 mmol, 1.00 Eq) in DCM (15 mL) was added m-CPBA (2.05 g, 10.10 mmol, 2.50 Eq) at 27° C. and stirred for 3 hr, TLC showed the reaction was completed, the mixture was diluted with EA and washed with sat.Na₂SO₃ and brine, the organic phase was dried over anhydrous Na₂SO₄, filtered and concentrated, the residue was purified by silica gel chromatography (PE:EA=5:1) to give compound 2 (750.00 mg, 2.85 mmol, 70.51% yield) as yellow oil. ¹H NMR (400 MHz, CDCl₃) δ 7.35-7.39 (m, 5 H), 5.15-5.19 (m, 2 H), 4.19-4.33 (m, 1 H), 4.15-4.16 (m, 1 H), 3.94 (m, 3 H), 3.47-3.50 (m, 1 H), 3.32-3.35 (m, 3 H), 3.00-3.04 (m, 1 H).

1.20.2 Preparation of Compound 3

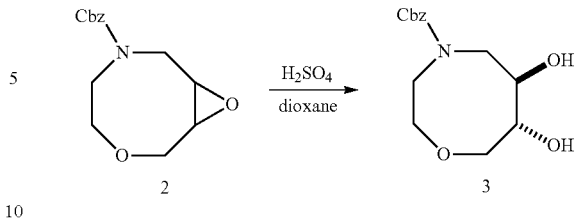

To a solution of compound 2 (270.00 mg, 1.03 mmol, 1.00 Eq) in dioxane (4.1 mL) was added H₂SO₄ (1.4 mL), the mixture was stirred at 50° C. for 4 hr, TLC showed the reaction was completed, the reaction solution was diluted with DCM and washed with sat.NaHCO₃ and brine, the organic phase was dried over anhydrous Na₂SO₄, filtered and concentrated, the residue was purified by silica gel chromatography (PE:EA=1:1) to give compound 3 (120.00 mg, 426.59 umol, 41.42% yield) as colorless oil.

1.20.3 Preparation of Compound A24

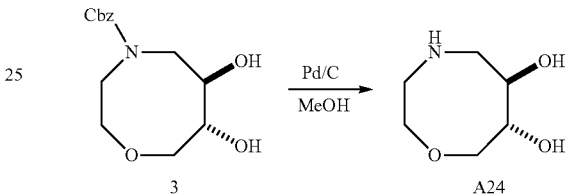

To a solution of compound 3 (120.00 mg, 426.59 umol, 1.00 Eq) in MeOH (20 mL) was added Pd/C (20.00 mg, 426.59 umol, 1.00 Eq) under N₂. The suspension was degassed under vacuum and purged with H₂ several times. The mixture was stirred under H₂ (15 psi) at 28° C. for 3 hr. TLC showed the starting material was consumed completely. The reaction mixture was filtered and the filter was concentrated to give A24 (50.00 mg, 339.74 umol, 79.64% yield) as colorless oil.

1.21 Preparation of Compound A25

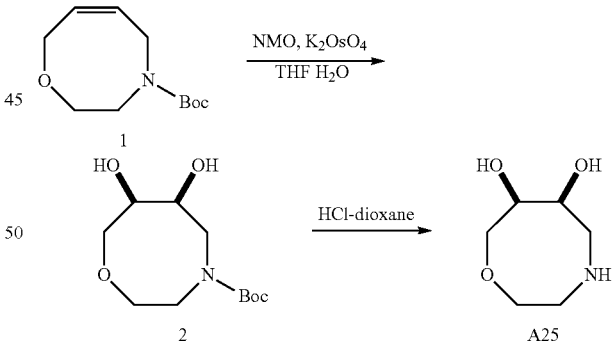

1.21.1 Preparation of Compound 2

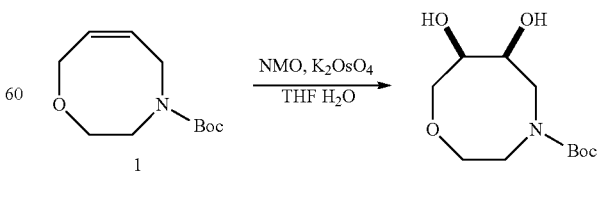

To a solution of compound 1 (499.05 mg, 2.34 mmol, 1.00 Eq) in THF (6 mL) and H₂O (3 mL) was added NMO (630.50 mg, 5.38 mmol, 2.30 Eq) and K$_2$OsO$_4$ (86.22 mg, 234.00 umol, 0.10 Eq). The mixture was stirred at 25° C. for 2 hr, TLC showed the reaction was completed, the reaction solution was diluted with EA, washed with sat.Na$_2$SO$_3$ and brine, the organic phase was dried over anhydrous Na$_2$SO$_4$, filtered and concentrated, the residue was purified by silica gel chromatography (PE:EA:DCM=1:1:1) to give compound 2 (300.00 mg, 1.21 mmol, 51.84% yield) as colorless oil.

1.21.2 Preparation of Compound A25

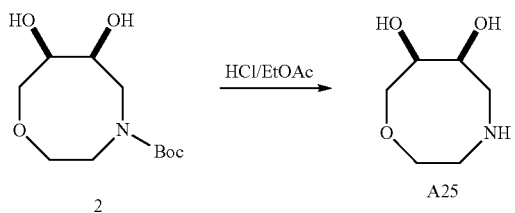

To a solution of compound 2 (300.00 mg, 1.21 mmol, 1.00 Eq) in EA (2 mL) was added HCl/EA (4 mL, 4M). The mixture was stirred at 25° C. for 1 hr, TLC showed the reaction was completed, the mixture was concentrated to give compound A25 (200.00 mg, crude) as white solid.

1.22 Preparation of A26

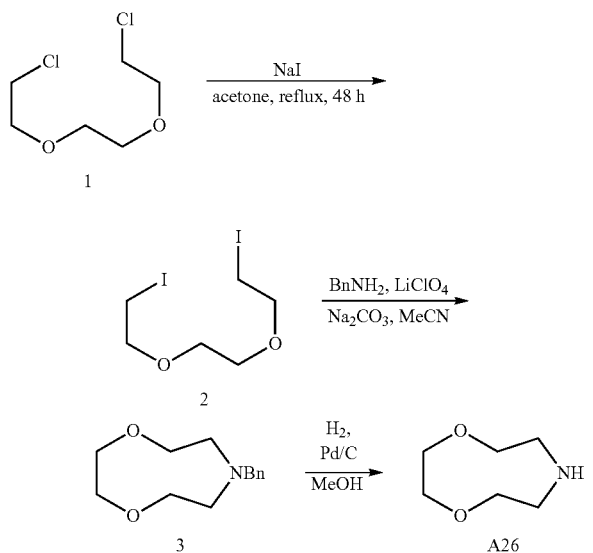

1.22.1 Preparation of Compound 2

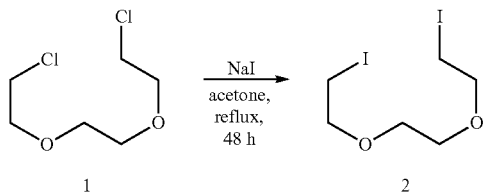

A mixture of 1,2-bis(2-chloroethoxy)ethane (5.00 g, 26.73 mmol, 1.00 Eq) and NaI (12.02 g, 80.19 mmol, 3.00 Eq) in acetone (50 mL) was stirred at 56° C. for 72 hr under N$_2$ atmosphere. Most solid sodium chloride was formed. After filtration of the resulting sodium chloride, the solution was concentrated in vacuum. The residue was diluted with CH$_2$Cl$_2$ (200 mL) and the solution was washed with water (100 mL), dried over Na$_2$SO$_4$ and evaporated in vacuum. The residue was purified by chromatography on silica gel (eluting with PE:EA=100:1 to 10:1) to afford the pure product 1,2-bis(2-iodoethoxy)ethane (9.10 g, 24.60 mmol, 92.02% yield) as a colorless oil. $^1$H NMR (400 MHz, CDCl$_3$) δ 3.80 (t, J=6.90 Hz, 4 H), 3.70 (s, 4 H), 3.29 (t, J=6.78 Hz, 4 H).

1.22.2 Preparation of Compound 3

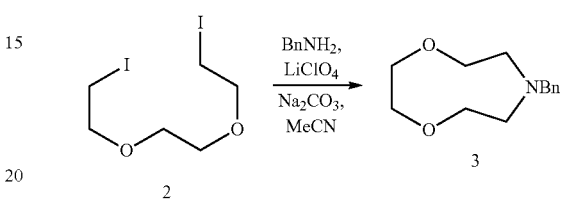

To a mixture of 1,2-bis(2-iodoethoxy)ethane (2.00 g, 5.41 mmol, 1.00 Eq), Na$_2$CO$_3$ (2.29 g, 21.64 mmol, 4.00 Eq) and LiClO$_4$ (2.30 g, 21.64 mmol, 4.00 Eq) in MeCN (200 mL) was added phenylmethanamine (579.24 mg, 5.41 mmol, 1.00 Eq). The mixture was stirred at 80° C. for 24 hr under N$_2$ protection. TLC showed the material was consumed, the mixture was concentrated, the residue was washed with water (60 mL), extracted with EA (50 mL*3), the combined organic layer was dried over anhydrous Na$_2$SO$_4$, filtered and concentrated, the residue was purified by chromatography (silica gel, eluting with PE:EA=10:1 to 3:1) to afford product 7-benzyl-1,4,7-dioxazonane (370.00 mg, 1.67 mmol, 30.91% yield) as colorless oil. $^1$H NMR (400 MHz, CDCl$_3$) δ 7.23-7.43 (m, 5 H), 3.69-3.84 (m, 10 H), 2.86-3.00 (m, 4 H).

1.22.3 Preparation of Compound A26

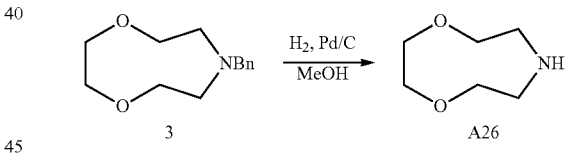

To a solution of 7-benzyl-1,4,7-dioxazonane (370.00 mg, 1.67 mmol, 1.00 Eq) in MeOH (20 mL) was added Pd/C (50.00 mg) under N$_2$. The suspension was degassed under vacuum and purged with H$_2$ several times. The mixture was stirred under H$_2$ (50 psi) at 28° C. for 24 hours. TLC (Petroleum ether/Ethyl acetate=3:1) showed the starting material was consumed completely. The reaction mixture was filtered and the filter was concentrated to give crude product 1,4,7-dioxazonane (170.00 mg, 1.30 mmol, 77.61% yield) as light yellow oil.

1.23 Preparation of A27

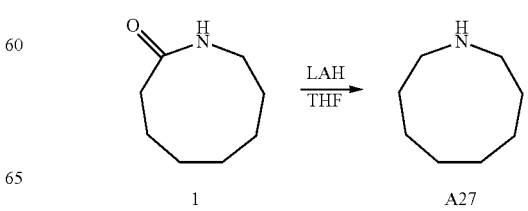

1.23.1 Preparation of Compound A27

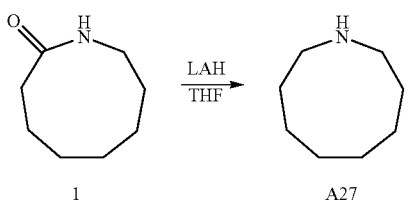

To a solution of compound 1 (2.00 g, 14.16 mmol) in THF (30 mL) was added LAH (1.61 g, 42.48 mmol) in portions at −10° C. under $N_2$. The mixture was stirred at 10° C. for 16 h. Then mixture was quenched by $H_2O$ (1.6 mL), 15% NaOH (1.6 mL) and $H_2O$ (3.2 mL). The mixture was diluted with THF (10 mL), filtrated, the filtrate was washed with aq.$NH_4Cl$ (50 mL), the aqueous layer was extracted with EA (50 mL*3). The organic layer was added into HCl/Dioxane (10 mL, 4M). The mixture was concentrated in vacuum to afford compound A27 as brown solid (2.20 g, HCl salt, 94.92%).

1.24 Preparation of Compound A28

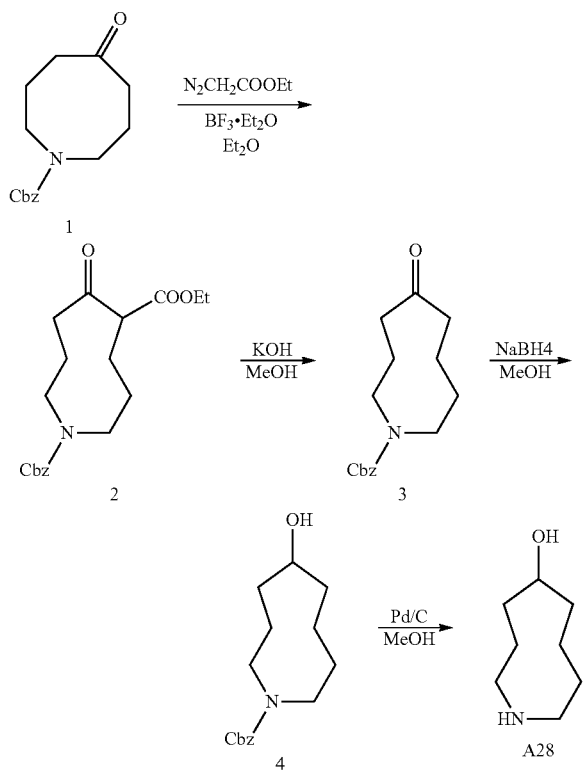

1.24.1 Preparation of Compound 2

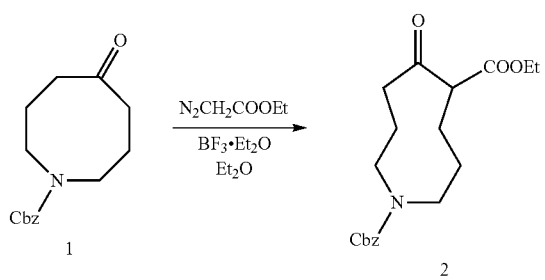 [SMILES: O=C1CCCN(C(=O)OCc2ccccc2)CCC1 ; CCOC(=O)C1CCCN(C(=O)OCc2ccccc2)CCCC1=O]

A solution of compound 1 (1.00 g, 3.83 mmol, 1.00 Eq) in $Et_2O$ (20 mL) was cooled to −35° C., $BF_3.Et_2O$ (2.17 g, 15.31 mmol, 4.00 Eq) and ethyl 2-diazoacetate (1.75 g, 15.31 mmol, 4.00 Eq) was added, the mixture was stirred at −35~25° C. for 1 hr, then warmed to 25° C. and stirred for 1 hr. TLC showed SM couldn't consumed completely, the mixture was diluted with EA and washed with $NaHCO_3$, the organic phase was dried and concentrated, the residue was purified by silica gel chromatography (PE:EA=10:1) to give crude product compound 2 (180.00 mg, crude) as yellow oil.

1.24.2 Preparation of Compound 3

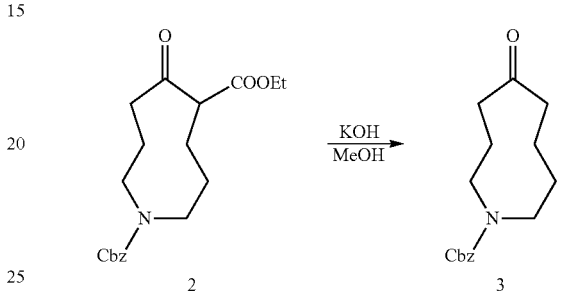

To a solution of compound 2 (180.00 mg, 518.13 umol, 1.00 Eq) in MeOH (2 mL) and $H_2O$ (4 mL) was added KOH (58.14 mg, 1.04 mmol, 2.00 Eq), the mixture was stirred to reflux at 80° C. for 3 hr. LCMS showed the reaction was completed, the mixture was diluted with EA and washed with water, the organic phase was dried over anhydrous $Na_2SO_4$, filtered and concentrated, the residue was purified by flash column to give compound 3 (60.00 mg, 217.91 umol, 42.06% yield) as colorless oil. $^1H$ NMR (400 MHz, $CDCl_3$): δ 7.31-7.45 (m, 5 H), 5.15 (S, 2 H), 3.23-3.34 (m, 4 H), 2.43-2.45 (m, 4 H), 2.10-2.17 (m, 2 H), 1.82-1.92 (m, 4 H). LCMS: 276.1 [M+1], 298.1 [M+23].

1.24.3 Preparation of Compound 4

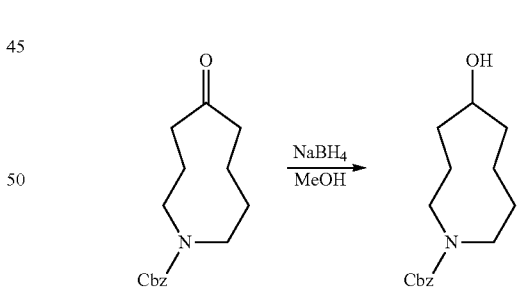

To a solution of compound 3 (60.00 mg, 217.91 umol, 1.00 Eq) in MeOH (5 mL) was added $NaBH_4$ (24.73 mg, 653.73 umol, 3.00 Eq) at 0° C., the mixture was stirred at 25° C. for 30 min, TLC showed the reaction was completed, the mixture was poured into sat.$NH_4Cl$ (20 mL), extracted with EA (20 mL*3), washed with brine, the organic phase was dried over anhydrous $Na_2SO_4$, filtered and concentrated to give product compound 4 (56.00 mg, 201.90 umol, 92.65% yield) as colorless oil.

1.24.4 Preparation of Compound A28

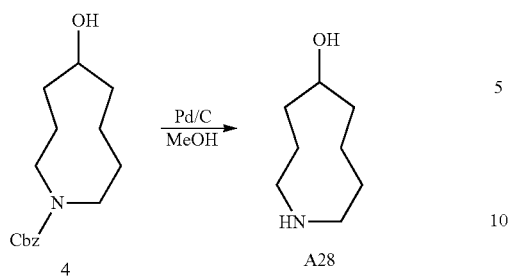

To a solution of compound 4 (56.00 mg, 201.90 umol, 1.00 Eq) in MeOH (10 mL) was added Pd/C (10.00 mg, 201.90 umol, 1.00 Eq) under $N_2$. The suspension was degassed under vacuum and purged with $H_2$ several times. The mixture was stirred under $H_2$ (15 Psi) at 25° C. for 1 hr. TLC showed the starting material was consumed completely. The reaction mixture was filtered and the filter was concentrated to give compound A28 (35.00 mg, crude) as white solid.

Part II General Procedure for Targets

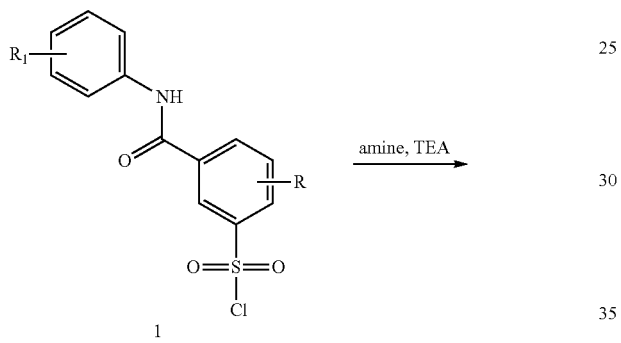

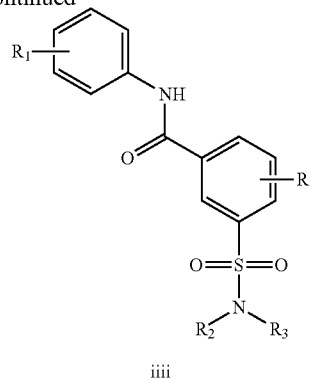

To a solution of Compound 1 (0.3 mmol) in MeCN (3 mL) was added amine (0.3 mmol) and $Et_3N$ (30 mg, 0.33 mmol) at rt, and the mixture was stirred at rt for 2 h. The mixture was diluted with $CH_2Cl_2$ (20 mL) and washed with water. The organic phase was concentrated in vacuo to give the crude product, which was purified by prep-HPLC to give the desired product.

Resolution of Chiral Compounds

Chiral resolution of selected compounds of the invention was performed according to the conditions listed in Table 2.

TABLE 2

| Structure | Compound ID | Supercritical Fluid Chromatography Resolution condition |
|---|---|---|
|  | 2039<br>(2039_E1)<br>(2039_E2) | Instrument: SFC 80<br>Column: AD-5 μm.<br>Mobile phase: A for $CO_2$ and B for MeOH (0.1% $NH_3H_2O$)<br>Gradient: B 40%<br>Flow rate: 45 mL/min<br>Back pressure: 100 bar<br>Column temperature: 35° C.<br>Wavelength: 220 nm |

TABLE 2-continued

| Structure | Compound ID | Supercritical Fluid Chromatography Resolution condition |
|---|---|---|
| 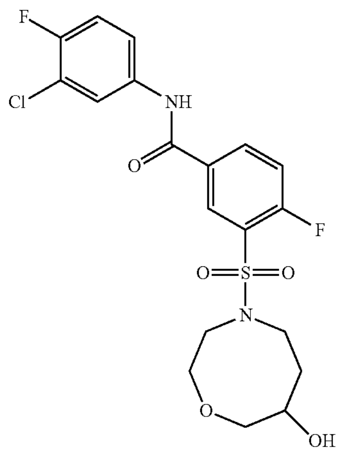 [SMILES: O=C(Nc1ccc(F)c(Cl)c1)c1ccc(F)c(S(=O)(=O)N2CCOCC(O)CC2)c1] | 2040 (2040_E1) (2040_E2) | Instrument: SFC 80<br>Column: AD-5 μm.<br>Mobile phase: A for $CO_2$ and B for EtOH (0.1% $NH_3H_2O$)<br>Gradient: B 40%<br>Flow rate: 50 mL/min<br>Back pressure: 100 bar<br>Column temperature: 35° C.<br>Wavelength: 220 nm |
| 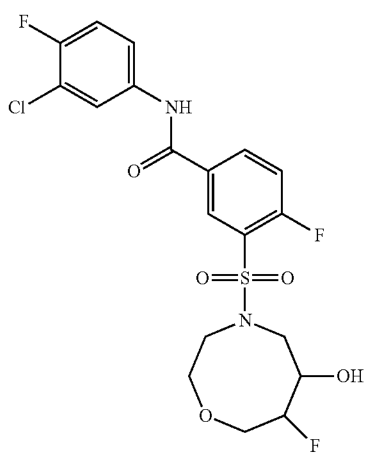 [SMILES: O=C(Nc1ccc(F)c(Cl)c1)c1ccc(F)c(S(=O)(=O)N2CCOCC(F)C(O)C2)c1] | 2297 | Instrument: SFC 80<br>Column: AD-5 μm.<br>Mobile phase: A for $CO_2$ and B for EtOH (0.1% $NH_3H_2O$)<br>Gradient: B 40%<br>Flow rate: 45 mL/min<br>Back pressure: 100 bar<br>Column temperature: 35° C.<br>Wavelength: 220 nm |
| 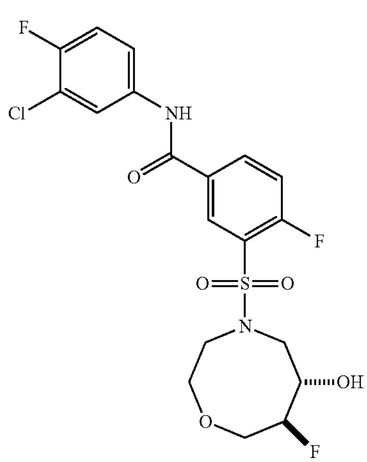 [SMILES: O=C(Nc1ccc(F)c(Cl)c1)c1ccc(F)c(S(=O)(=O)N2CCOC[C@H](F)[C@@H](O)C2)c1] | 2297_Trans1 | |

TABLE 2-continued

| Structure | Compound ID | Supercritical Fluid Chromatography Resolution condition |
|---|---|---|
| (structure) | 2297_Trans2 | |
| (structure) | 2301 | Instrument: SFC 80<br>Column: AD-5 μm.<br>Mobile phase: A for $CO_2$ and B for EtOH (0.1% $NH_3H_2O$)<br>Gradient: B 40%<br>Flow rate: 45 mL/min<br>Back pressure: 100 bar<br>Column temperature: 35° C.<br>Wavelength: 220 nm |
| (structure) | 2301_Trans1 | |

TABLE 2-continued

| Structure | Compound ID | Supercritical Fluid Chromatography Resolution condition |
|---|---|---|
| [Structure: 4-fluoro-3-chlorophenyl amide of 4-fluoro-3-(sulfonyl-linked (7-fluoro-8-hydroxy-1,5-oxazocan-5-yl))benzoic acid] | 2301_Trans2 | |
| [Structure: 3,4,5-trifluorophenyl amide of 4-fluoro-3-(sulfonyl-linked (7-hydroxy-1,5-oxazocan-5-yl))benzoic acid] | 2520 (2520_E1) (2520_E2) | Instrument: SFC 80 Column: AD-10 μm. Mobile phase: A for $CO_2$ and B for MeOH (0.1% $NH_3H_2O$) Gradient: B 50% Flow rate: 70 mL/min Back pressure: 100 bar Column temperature: 35° C. Wavelength: 220 nm |

Example:

HBV Assembly Assay

The fluorescence quenching in vitro assembly HBV assay was developed according to a method described by Zlotnick and coworkers (Nature Biotechnology 2006, 24:358). The assay is based on the observation that the C-termini of the HBV core protein cluster together during capsid formation. This assay utilizes a mutant C150 HBV capsid protein where all wild-type cysteines are mutated to alanines, but a C-terminal cysteine residue is preserved and is labeled with fluorescent BoDIPY-FL dye. HBV C150Bo protein is highly fluorescent, however the fluorescence is drastically reduced during the capsid assembly process. Thus, the assay measures the ability and potency of test compounds to modulate capsid assembly by monitoring the fluorescence of the labeled capsid C150Bo protein.

In a typical assay, the mutant HBV C150 protein (amino acids 1-150, C49A, C61A, C107A, 150C) is cloned into a T7 RNA-polymerase based expression vector, expressed in *E. coli* and purified to homogeneity as a dimer. The purified HBV core protein is desalted and labeled with BODIPY-FL Dye.

In a non-limiting embodiment, the assembly assay is conducted in 96-well plate format. The assembly reactions are carried out in 50 mM Hepes buffer, pH 7.5 and 150 mM NaCl. The compounds are pre-incubated with the HBV CA protein for 15 min, and the assembly reactions are initiated by addition of NaCl. The reaction is allowed to continue for 1 hour at room temperature.

To determine the effect on capsid assembly, each test compound is initially screened at least 4 different concentrations in duplicates. Primary hits are compounds that show activity in the assembly assay at 10 uM. Identified primary hits are confirmed in follow-up studies as described elsewhere herein. Known modulators of HBV CA assembly, such as HAP-1 and BAY 41-4109, are used as control compounds in these experiments and exhibited $EC_{50}$ values consistent with the literature. $EC_{50}$ values for test compounds are determined via analysis of the dose-response curve.

Selected compounds of the invention were assayed in the HBV assembly assay, as described above. The assembly assay was conducted in 96-well plate format. The assembly reactions were carried out in 50 mM Hepes buffer, pH 7.5 and 150 mM NaCl. The compounds were pre-incubated with the HBV CA protein for 15 min, and the assembly reactions were initiated by addition of NaCl. The reaction was allowed to continue for 1 hour at room temperature. The 96-well plate assembly assay consistently had Z' factors greater than 0.7 and were robust and reproducible both from plate-to-plate and day-to-day.

To determine the effect on capsid assembly, each test compound was initially screened at 5 different concentrations: about 30 µM, 10 µM, 3 µM, 1 µM, and 0.3 µM in duplicates. Primary hits were compounds that show >50% activity in the assembly assay at about 10 µM and a representative group of these active compounds is shown in Table 3.

TABLE 3

HBV assembly assay ('+' indicates >50% activity at about 10 µM)

| Compound | Activity |
|---|---|
| 2039 | + |
| 2039_E1 | + |
| 2039_E2 | + |
| 2040 | + |
| 2040_E1 | + |
| 2040_E2 | + |
| 2285_D1 | + |
| 2285_D2 | + |
| 2435 | + |
| 2436 | + |
| 2520 | + |
| 2520_E1 | + |
| 2520_E2 | + |

Example:

Inhibition of HBV Replication Dot-Blot Assay

Compounds active in the HBV assembly assay are tested for their activity and toxicity in cellular assay. In the first anti-viral assay, the ability of compounds to inhibit HBV replication in an HBV-producing hepatoma cell line using the dot-blot method is evaluated.

Briefly, confluent monolayers of HepG2-2.2.15 cells are incubated with complete medium containing various concentrations of a test compound. Three days later, the culture medium is replaced with fresh medium containing the appropriately diluted test compound. Six days following the initial administration of the test compound, the cell culture supernatant is collected, and cell lysis is performed. The samples are applied onto Nylos membranes and DNA is immobilized to the membrane by UV cross-linking. After pre-hybridization, the HBV probe is added and the hybridization is performed overnight. The membranes are exposed to the Kodak films; antiviral activity is calculated from the reduction in HBV DNA levels ($EC_{50}$). The $EC_{50}$ for antiviral activity is calculated from the dose response curves of active compounds. Assay performance over time is monitored by the use of the standard positive control compounds ETV, BAY 41-4109, and HAP-1.

Compound cytotoxicity ($TC_{50}$) is measured in this same HepG2-2.2.15 cell line using a CellTiter Blue-based cytotoxicity assay employed as recommended by manufacturer (Promega). To confirm and expand these results, a second antiviral assay is carried out on active compounds using the stable HBV cell line HepG2.2.15 and measuring anti-HBV potency by real-time PCR and cytotoxicity by CellTiter Blue. In this assay, 24 hours after cell seeding, HepG2-2.2.15 cells are incubated with complete medium containing various concentrations of a test compound with BAY 41-4109 and HAP-1 used as positive controls. After three days, the culture medium is replaced with fresh medium containing the appropriately diluted test compound. The cell culture is collected six days following the initial administration of the test compound, followed by HBV DNA extraction using QIAamp 96 DNA Blood Kit (Qiagen). The extracted HBV DNA is diluted and analyzed by Real-Time PCR. A standard curve is generated by plotting Ct value vs the amount of HBV plasmid standard. Cytotoxicity is determined similarly to the above described method by applying a dye uptake method (CellTiter Blue kit, Promega).

Selected compounds were tested for their activity and toxicity in cellular assay. In the first anti-viral assay, the ability of compounds to inhibit HBV replication in an HBV-producing hepatoma cell line using the dot-blot method was evaluated.

Confluent monolayers of HepG2-2.2.15 cells were incubated with complete medium containing various concentrations of a test compound. Three days later, the culture medium was replaced with fresh medium containing the appropriately diluted test compound. Six days following the initial administration of the test compound, the cell culture supernatant was collected, and cell lysis was performed. The samples were applied onto Nylos membranes and DNA was immobilized to the membrane by UV cross-linking. After pre-hybridization, the HBV probe was added and the hybridization was performed overnight. The membranes were exposed to the Kodak films; antiviral activity was calculated from the reduction in HBV DNA levels ($EC_{50}$). The $EC_{50}$ for antiviral activity was calculated from the dose response curves of active compounds. Assay performance over time was monitored by the use of the standard positive control compounds ETV, BAY 41-4109, and HAP-1. Results for selected compounds of the invention are illustrated in Table 4.

Cytotoxicity ($CC_{50}$) was measured in this same HepG2-2.2.15 cell line using a CellTiter Blue-based cytotoxicity assay employed as recommended by manufacturer (Promega).

TABLE 4

"Activity" represents activity in dot-blot-assay ('+' indicates >50% activity at 10 µM)

| Compound | Activity |
|---|---|
| 2039 | + |
| 2039_E1 | + |
| 2039_E2 | + |
| 2040 | + |
| 2040_E1 | + |
| 2040_E2 | + |
| 2285_D1 | + |
| 2285_D2 | + |
| 2435 | + |
| 2436 | + |
| 2520 | + |
| 2520_E1 | + |
| 2520_E2 | + |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

The invention claimed is:

1. A compound of Formula I:

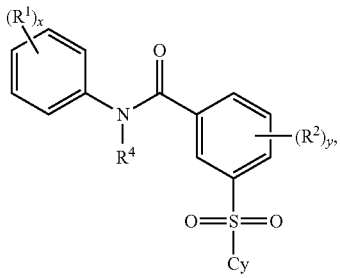

or a pharmaceutically acceptable salt thereof;
wherein
$R^4$ is —H or —$C_1$-$C_3$ alkyl;
$R^1$ is, independently at each occurrence, —OH, halo, —CN, —$NO_2$, —$H_2PO_4$, —$C_1$-$C_6$ alkyl, —O—$C_1$-$C_6$ alkyl, —$C_1$-$C_6$ heteroalkyl, —O—$C_1$-$C_6$ heteroalkyl, —$C_3$-$C_{10}$ cycloalkyl, —$C_3$-$C_{10}$ heterocycloalkyl, $C_6$-$C_{10}$ aryl, $C_5$-$C_9$ heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-($C_6$-$C_{10}$ aryl), or —$C_1$-$C_4$ alkyl-($C_5$-$C_9$ heteroaryl), wherein the alkyl, heteroalkyl, cycloalkyl, heterocycloalkyl, aryl and heteroaryl groups are optionally substituted 1-5 times with halo, —OH, —CN, or —$NO_2$;
$R^2$ is, independently at each occurrence, —OH, halo, —CN, —$NO_2$, $R^6$, or $OR^6$, wherein $R^6$ is, independently at each occurrence, —$C_1$-$C_6$ alkyl, —$C_1$-$C_6$ heteroalkyl, —$C_3$-$C_{10}$ cycloalkyl, —$C_3$-$C_{10}$ heterocycloalkyl, $C_6$-$C_{10}$ aryl, $C_5$-$C_{10}$ heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-($C_6$-$C_{10}$ aryl), or —$C_1$-$C_4$ alkyl-($C_5$-$C_{10}$ heteroaryl), wherein the alkyl, heteroalkyl, cycloalkyl, heterocycloalkyl, aryl and heteroaryl groups are optionally substituted 1-5 times with halo, —OH, —CN, or —$NO_2$;
Cy is

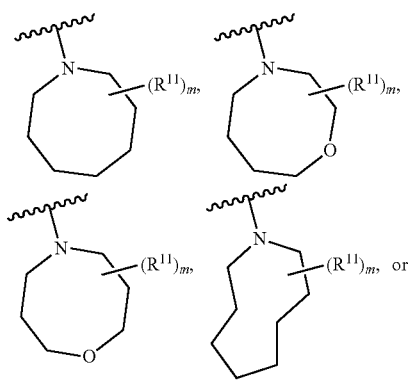

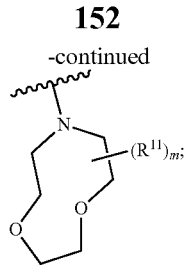

wherein
$R^{11}$ is, independently at each occurrence, —OH, halo, —CN, —$NO_2$, —$C_1$-$C_6$ alkyl, —O—$C_1$-$C_6$ alkyl, —$C_1$-$C_6$ heteroalkyl, —O—$C_1$-$C_6$ heteroalkyl, —$C_3$-$C_{10}$ cycloalkyl, —$C_3$-$C_{10}$ heterocycloalkyl, $C_6$-$C_{10}$ aryl, $C_5$-$C_9$ heteroaryl, —$C_1$-$C_4$ alkyl-($C_3$-$C_{10}$ cycloalkyl), —$C_1$-$C_4$ alkyl-($C_3$-$C_{10}$ heterocycloalkyl), —$C_1$-$C_4$ alkyl-($C_6$-$C_{10}$ aryl), or —$C_1$-$C_4$ alkyl-($C_5$-$C_9$ heteroaryl), wherein the alkyl, heteroalkyl, cycloalkyl, heterocycloalkyl, aryl and heteroaryl groups are optionally substituted 1-5 times with halo, —OH, —CN, or —$NO_2$, or two $R^{11}$ groups, together with the carbons to which they are attached, join to form a cyclic phosphate ring;
m is 0, 1, 2, 3, or 4;
x is 0, 1, 2, 3, 4, or 5; and
y is 0, 1, 2, 3, or 4.

2. The compound of claim 1, or a pharmaceutically acceptable salt thereof;
wherein
$R^4$ is H;
m is 0, 1, 2, or 3;
x is 0, 1, 2, or 3; and
y is 0, 1, 2, or 3.

3. The compound of claim 1, or a pharmaceutically acceptable salt thereof;
wherein
$R^1$ is, independently at each occurrence, —OH, halo, —CN, —$NO_2$, —$C_1$-$C_6$ alkyl, —O—$C_1$-$C_6$ alkyl, —$C_1$-$C_6$ heteroalkyl, —O—$C_1$-$C_6$ heteroalkyl, —$C_3$-$C_{10}$ cycloalkyl, —$C_3$-$C_{10}$ heterocycloalkyl, —$C_1$-$C_4$ alkyl-($C_3$-$C_{10}$ cycloalkyl), or —$C_1$-$C_4$ alkyl-($C_3$-$C_{10}$ heterocycloalkyl), wherein the alkyl group is optionally substituted 1-5 times with halo or —OH.

4. The compound of claim 1, or a pharmaceutically acceptable salt thereof;
wherein
$R^2$ is, independently at each occurrence, —OH, halo, —CN, —$NO_2$, $R^6$, or $OR^6$, wherein $R^6$ is, independently at each occurrence, —$C_1$-$C_6$ alkyl, —$C_1$-$C_6$ heteroalkyl, —$C_3$-$C_{10}$ cycloalkyl, —$C_3$-$C_{10}$ heterocycloalkyl, —$C_1$-$C_4$ alkyl-($C_3$-$C_{10}$ cycloalkyl), or —$C_1$-$C_4$ alkyl-($C_3$-$C_{10}$ heterocycloalkyl), wherein the alkyl group is optionally substituted 1-5 times with halo or —OH.

5. The compound of claim 1, or a pharmaceutically acceptable salt thereof;
wherein
$R^{11}$ is, independently at each occurrence, —OH, halo, —CN, —$NO_2$, —$C_1$-$C_6$ alkyl, —O—$C_1$-$C_6$ alkyl, —$C_1$-$C_6$ hetero alkyl, —O—$C_1$-$C_6$ hetero alkyl, —$C_3$-$C_{10}$ cycloalkyl, —$C_3$-$C_{10}$ heterocycloalkyl, —$C_1$-$C_4$ alkyl-($C_3$-$C_{10}$ cycloalkyl), or —$C_1$-$C_4$ alkyl-($C_3$-$C_{10}$ heterocycloalkyl), wherein the alkyl group is optionally substituted 1-5 times with halo or —OH.

6. The compound of claim 1, or a pharmaceutically acceptable salt thereof;
wherein
$R^{11}$ is, independently at each occurrence, —OH, halo, —$C_1$-$C_6$ alkyl, —$C_1$-$C_6$ heteroalkyl, —$C_3$-$C_{10}$ cycloalkyl, or —$C_3$-$C_{10}$ heterocycloalkyl.

7. The compound of claim 1, or a pharmaceutically acceptable salt thereof;
wherein
$R^4$ is H;
each $R^1$ is, independently at each occurrence, —OH, halo, —CN, —$NO_2$, or —$C_1$-$C_6$ alkyl;
$R^2$ is selected from —OH, halo, —$C_1$-$C_6$ alkyl, —$C_1$-$C_6$ heteroalkyl, —$C_3$-$C_{10}$ cycloalkyl, and —$C_3$-$C_{10}$ heterocycloalkyl, wherein the alkyl and cycloalkyl groups are optionally substituted 1-5 times with halo;
Cy is

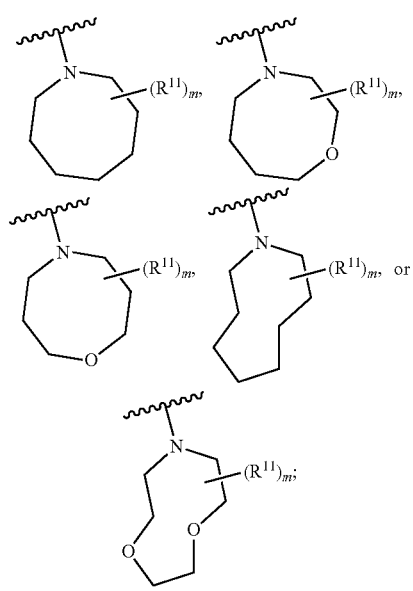

wherein
$R^{11}$ is, independently at each occurrence, —OH or halo;
m is 0, 1 or 2; and
x is 0, 1, 2, or 3.

8. The compound of claim 1, or a pharmaceutically acceptable salt thereof;
wherein
$R^4$ is H;
each $R^1$ is, independently at each occurrence, —OH or halo;
$R^2$ is selected from —OH, halo, and —$C_1$-$C_6$ alkyl, wherein the alkyl group is optionally substituted 1-5 times with halo;
Cy is

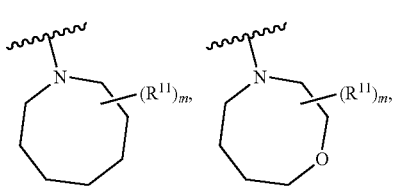

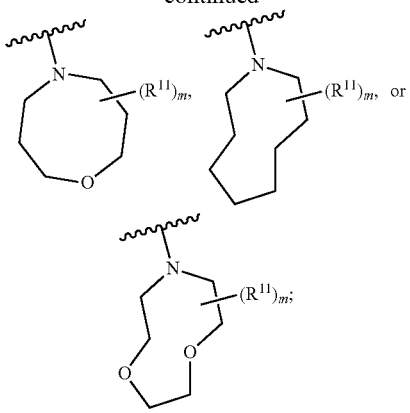

wherein
$R^{11}$ is, independently at each occurrence, —OH, halo, —$C_1$-$C_6$ alkyl, —$C_1$-$C_6$ heteroalkyl, —$C_3$-$C_{10}$ cycloalkyl, or —$C_3$-$C_{10}$ heterocycloalkyl;
m is 0, 1 or 2; and
x is 0, 1, 2, or 3.

9. The compound of claim 1, or a pharmaceutically acceptable salt thereof;
wherein
$R^4$ is H;
each $R^1$ is, independently at each occurrence, —OH or halo;
$R^2$ is selected from halo and —$C_1$-$C_3$ alkyl, wherein the alkyl group is optionally substituted 1-3 times with halo;
Cy is

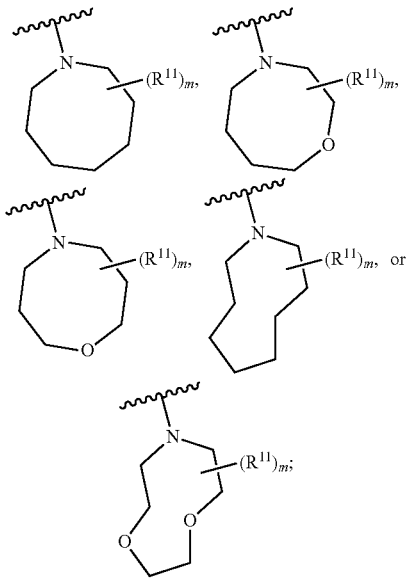

wherein
$R^{11}$ is, independently at each occurrence, —OH, halo, —$C_1$-$C_3$ alkyl, —$C_1$-$C_4$ heteroalkyl, —$C_3$-$C_7$ cycloalkyl, or —$C_3$-$C_7$ heterocycloalkyl;
m is 0, 1 or 2; and
x is 0, 1, 2, or 3.

10. The compound of claim 1, or a pharmaceutically acceptable salt thereof;

wherein
R⁴ is H;
each R¹ is, independently at each occurrence, halo;
R² is selected from halo and —C₁ alkyl, wherein the alkyl group is optionally substituted 1-3 times with halo;
Cy is

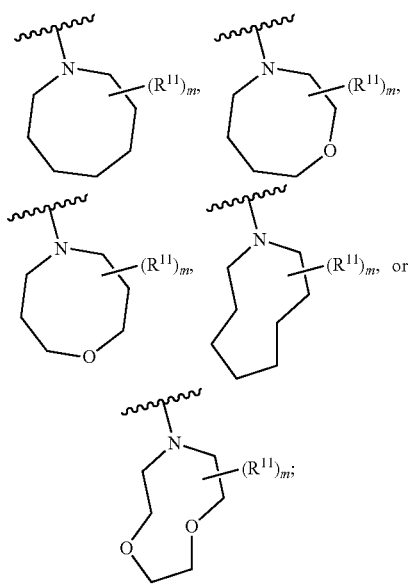

wherein
R¹¹ is, independently at each occurrence, —OH, halo, —C₁-C₃ alkyl, or —C₃-C₇ cycloalkyl;
m is 0, 1 or 2; and
x is 2 or 3.

11. The compound of claim 1, or a pharmaceutically acceptable salt thereof;
wherein
R⁴ is H;
each R¹ is, independently at each occurrence, halo;
R² is selected from halo and —C₁ alkyl, wherein the alkyl group is optionally substituted 1-3 times with halo;
Cy is

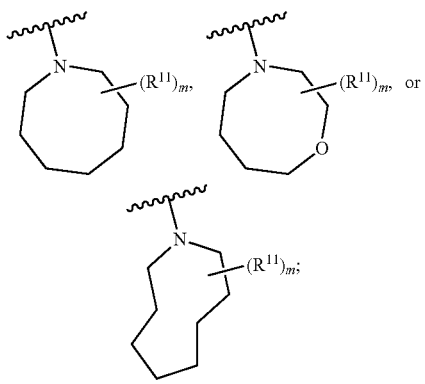

wherein
R¹¹ is, independently at each occurrence, —OH, halo, —C₁-C₃ alkyl, or —C₃-C₇ cycloalkyl;
m is 0, 1 or 2; and
x is 2 or 3.

12. The compound of claim 11, or a pharmaceutically acceptable salt thereof, wherein the compound is selected from:

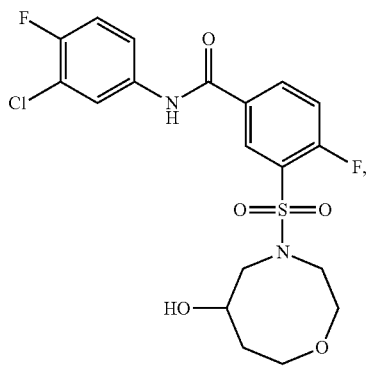

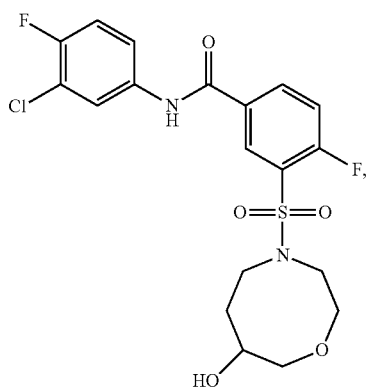

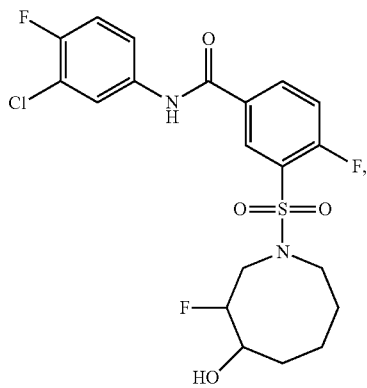

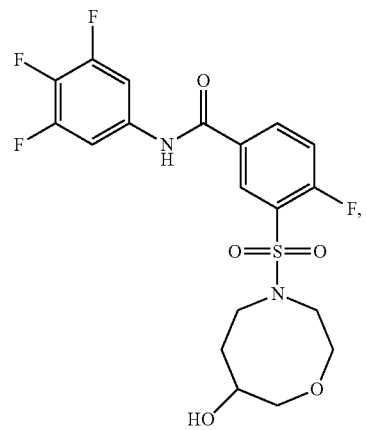

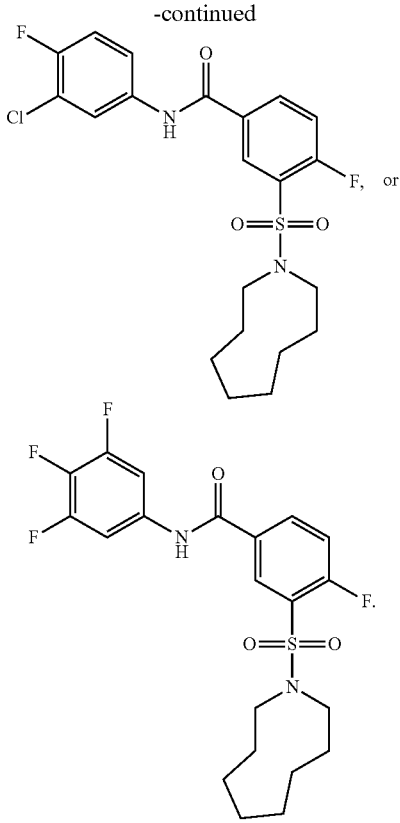

13. A composition comprising a compound according to claim 1, or a pharmaceutically acceptable salt thereof.

14. The composition of claim 13, wherein the composition is a pharmaceutical composition and further comprises at least one pharmaceutically acceptable carrier.

15. A method of treating an HBV infection in an individual in need thereof, comprising administering to the individual a therapeutically effective amount of a compound according to claim 1.

16. The method of claim 15, further comprising administering to the individual at least one additional therapeutic agent selected from the group consisting of a HBV polymerase inhibitor, immunomodulatory agents, pegylated interferon, viral entry inhibitor, viral maturation inhibitor, capsid assembly modulator, reverse transcriptase inhibitor, a cyclophilin/TNF inhibitor, a TLR-agonist, and an HBV vaccine, and a combination thereof.

17. The method of claim 16, wherein the therapeutic agent is a reverse transcriptase inhibitor, and is at least one of Zidovudine, Didanosine, Zalcitabine, 2',3'-dideoxyadenosine, Stavudine, Lamivudine, Abacavir, Emtricitabine, Entecavir, Apricitabine, Atevirapine, ribavirin, acyclovir, famciclovir, valacyclovir, ganciclovir, valganciclovir, Tenofovir, Adefovir, cidofovir, Efavirenz, Nevirapine, Delavirdine, and Etravirine.

18. The method of claim 16, wherein the therapeutic agent is an interferon selected from the group consisting of interferon alpha (IFN-α), interferon beta (IFN-β), interferon lambda (IFN-λ) and interferon gamma (IFN-γ).

19. The method of claim 18, wherein the interferon is interferon-alpha-2a, interferon-alpha-2b, or interferon-alpha-n1.

20. The method of claim 19, wherein the interferon-alpha-2a or interferon-alpha-2b is pegylated.

21. The method of claim 19, wherein the interferon-alpha-2a is pegylated interferon-alpha-2a.

22. The method of claim 15, further comprising administering to the individual at least one HBV vaccine, a nucleoside HBV inhibitor, an interferon or any combination thereof.

23. A method of treating an HBV infection in an individual in need thereof, comprising reducing the HBV viral load by administering to the individual a therapeutically effective amount of a compound according to claim 1 alone or in combination with a reverse transcriptase inhibitor; and further administering to the individual a therapeutically effective amount of an HBV vaccine.

24. The compound of claim 11, or a pharmaceutically acceptable salt thereof, wherein the compound is selected from:

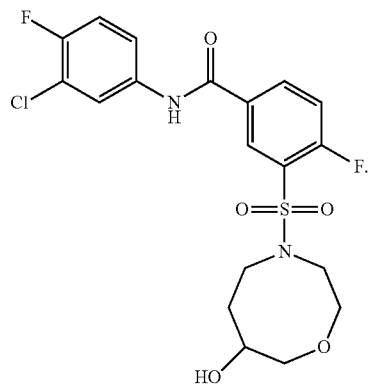 [SMILES: O=C(Nc1ccc(F)c(Cl)c1)c1ccc(F)c(S(=O)(=O)N2CCOCC(O)CC2)c1]

* * * * *